(12) United States Patent
Stennicke et al.

(10) Patent No.: US 10,906,965 B2
(45) Date of Patent: Feb. 2, 2021

(54) METHODS OF TREATING AUTOIMMUNE DISEASE OR CHRONIC INFLAMMATION WTIH ANTIBODIES THAT BIND PEPTIDOGLYCAN RECOGNITION PROTEIN 1

(71) Applicant: Novo Nordisk A/S, Bagsvaerd (DK)

(72) Inventors: Vibeke Westphal Stennicke, Kokkedal (DK); Christine Brender Read, Solborg (DK); Joseph Leon Kuijper, Kenmore, WA (US); Xiaoting Tang, Seattle, WA (US); Mark Heipel, Seattle, WA (US); Siv Annegrethe Hjorth, Virum (DK)

(73) Assignee: NOVO NORDISK A/S, Bagsvaerd (DK)

( * ) Notice: Subject to any disclaimer, the term of this patent is extended or adjusted under 35 U.S.C. 154(b) by 0 days.

(21) Appl. No.: 16/171,131

(22) Filed: Oct. 25, 2018

(65) Prior Publication Data

US 2019/0119367 A1 Apr. 25, 2019

Related U.S. Application Data

(63) Continuation of application No. 15/483,390, filed on Apr. 10, 2017, now Pat. No. 10,150,809, which is a continuation of application No. 14/376,968, filed as application No. PCT/EP2012/074093 on Nov. 30, 2012, now Pat. No. 9,663,568.

(60) Provisional application No. 61/598,968, filed on Feb. 15, 2012, provisional application No. 61/672,799, filed on Jul. 18, 2012.

(30) Foreign Application Priority Data

Mar. 12, 2012 (EP) .................................. 12158974

(51) Int. Cl.
*A61K 39/395* (2006.01)
*C07K 16/18* (2006.01)

(52) U.S. Cl.
CPC ........ *C07K 16/18* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,676,980 A | 6/1987 | Segal et al. |
| 4,683,195 A | 7/1987 | Mullis et al. |
| 4,683,202 A | 7/1987 | Mullis |
| 4,716,111 A | 12/1987 | Osband et al. |
| 4,736,866 A | 4/1988 | Leder et al. |
| 4,741,900 A | 5/1988 | Alvarez et al. |
| 4,816,397 A | 3/1989 | Boss et al. |
| 4,816,567 A | 3/1989 | Cabilly et al. |
| 4,870,009 A | 9/1989 | Evans et al. |
| 4,873,191 A | 10/1989 | Wagner et al. |
| 4,873,316 A | 10/1989 | Meade et al. |
| 4,946,778 A | 8/1990 | Ladner et al. |
| 4,980,286 A | 12/1990 | Morgan et al. |
| 4,987,071 A | 1/1991 | Cech et al. |
| 5,116,742 A | 5/1992 | Cech et al. |
| 5,223,409 A | 6/1993 | Ladner et al. |
| 5,225,539 A | 7/1993 | Winter |
| 5,258,498 A | 11/1993 | Huston et al. |
| 5,272,057 A | 12/1993 | Smulson et al. |
| 5,272,071 A | 12/1993 | Chappel |
| 5,283,317 A | 2/1994 | Saifer et al. |
| 5,328,470 A | 7/1994 | Nabel et al. |
| 5,403,484 A | 4/1995 | Ladner et al. |
| 5,413,923 A | 5/1995 | Kucherlapati et al. |
| 5,420,526 A | 5/1995 | Fensch |
| 5,424,286 A | 6/1995 | Eng |
| 5,427,908 A | 6/1995 | Dower et al. |
| 5,436,146 A | 7/1995 | Shenk et al. |
| 5,459,039 A | 10/1995 | Modrich et al. |
| 5,474,981 A | 12/1995 | Leder et al. |
| 5,498,531 A | 3/1996 | Jarrell |
| 5,516,637 A | 5/1996 | Huang et al. |
| 5,530,101 A | 6/1996 | Queen et al. |

(Continued)

FOREIGN PATENT DOCUMENTS

| | | |
|---|---|---|
| CA | 2342376 A1 | 9/2002 |
| CN | 101139599 A | 3/2008 |

(Continued)

OTHER PUBLICATIONS

Ramanthan, B., et al., "Cloning of porcine triggering receptor expressed on myeloid cells-1 (TREM-1) and its induction by lipopolysaccharide, peptidoglycan, and *Salmonella enterica* serovar Typhimurium infection," Developmental & Comparative Immunology 29:1-7, Elsevier, Netherlands (2005).

(Continued)

*Primary Examiner* — Christine J Saoud
*Assistant Examiner* — Jon M Lockard
(74) *Attorney, Agent, or Firm* — Morgan, Lewis & Bockius LLP

(57) ABSTRACT

Disclosed herein is a method for identifying TREM-1's ligand and antibodies, or fragments thereof, which are capable of modifying the function of TREM-1's ligand. Antibodies that reduce or block TREM-1 activation may be identified and selected using this method. Antibodies that bind to TREM-1's ligand and reduce TREM-1 activity may be suitable for use as medicaments.

6 Claims, 21 Drawing Sheets

Specification includes a Sequence Listing.

(56) References Cited

U.S. PATENT DOCUMENTS

| | | |
|---|---|---|
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,420,526 B1 | 7/2002 | Ruben et al. |
| 6,504,010 B1 | 1/2003 | Wang et al. |
| 6,509,448 B2 | 1/2003 | Wang et al. |
| 6,528,313 B1 | 3/2003 | Mouellic et al. |
| 6,858,204 B2 | 2/2005 | Henderson et al. |
| 6,878,687 B1 | 4/2005 | Ruben et al. |
| 8,013,116 B2 | 9/2011 | Faure et al. |
| 9,663,568 B2 | 5/2017 | Stennicke et al. |
| 2002/0128444 A1 | 9/2002 | Gingras et al. |
| 2002/0161201 A1 | 10/2002 | Filpula et al. |
| 2002/0172952 A1 | 11/2002 | Henderson et al. |
| 2002/0197669 A1 | 12/2002 | Bangur et al. |
| 2003/0049618 A1 | 3/2003 | Ruben et al. |
| 2003/0054363 A1 | 3/2003 | Henderson et al. |
| 2003/0077282 A1 | 4/2003 | Bigler et al. |
| 2003/0134283 A1 | 7/2003 | Peterson et al. |
| 2003/0165875 A1 | 9/2003 | Colonna et al. |
| 2003/0166068 A1 | 9/2003 | Ashida et al. |
| 2003/0170255 A1 | 9/2003 | Watanabe et al. |
| 2003/0175858 A1 | 9/2003 | Ruben et al. |
| 2003/0211510 A1 | 11/2003 | Henderson et al. |
| 2004/0236092 A1 | 11/2004 | Dziarski et al. |
| 2005/0238646 A1 | 10/2005 | Ledbetter et al. |
| 2005/0255114 A1 | 11/2005 | Labat et al. |
| 2006/0183125 A1 | 8/2006 | Mariani et al. |
| 2009/0092582 A1 | 4/2009 | Bogin et al. |
| 2010/0310560 A1 | 12/2010 | Colonna et al. |
| 2018/0016326 A1 | 1/2018 | Stennicke et al. |

FOREIGN PATENT DOCUMENTS

| | | |
|---|---|---|
| CN | 101619102 A | 1/2010 |
| EP | 0239400 A2 | 9/1987 |
| EP | 0264166 A1 | 4/1988 |
| EP | 0439098 A2 | 7/1991 |
| EP | 0519596 A1 | 12/1992 |
| EP | 0592106 A1 | 4/1994 |
| EP | 0239400 B1 | 8/1994 |
| EP | 1022286 A1 | 7/2000 |
| EP | 0592106 B1 | 11/2004 |
| EP | 1498424 A2 | 1/2005 |
| WO | WO-8809810 A1 | 12/1988 |
| WO | WO-8910134 A1 | 11/1989 |
| WO | WO-9002809 A1 | 3/1990 |
| WO | WO-9011354 A1 | 10/1990 |
| WO | WO-9101140 A1 | 2/1991 |
| WO | WO-9106667 A1 | 5/1991 |
| WO | WO-9109967 A1 | 7/1991 |
| WO | WO-9110737 A1 | 7/1991 |
| WO | WO-9110741 A1 | 7/1991 |
| WO | WO-9200968 A1 | 1/1992 |
| WO | WO-9201047 A1 | 1/1992 |
| WO | WO-9206180 A1 | 4/1992 |
| WO | WO-9218619 A1 | 10/1992 |
| WO | WO-9220316 A2 | 11/1992 |
| WO | WO-9222324 A1 | 12/1992 |
| WO | WO-9222635 A1 | 12/1992 |
| WO | WO-9304169 A1 | 3/1993 |
| WO | WO-9311236 A1 | 6/1993 |
| WO | WO-9314188 A1 | 7/1993 |
| WO | WO-9320221 A1 | 10/1993 |
| WO | WO-9321232 A1 | 10/1993 |
| WO | WO-9408598 A1 | 4/1994 |
| WO | WO-9410300 A1 | 5/1994 |
| WO | WO-9412649 A2 | 6/1994 |
| WO | WO-9416101 A2 | 7/1994 |
| WO | WO-9515982 A2 | 6/1995 |
| WO | WO-9520401 A1 | 8/1995 |
| WO | WO-9633735 A1 | 10/1996 |
| WO | WO-9634096 A1 | 10/1996 |
| WO | WO-9707668 A1 | 3/1997 |
| WO | WO-9707669 A1 | 3/1997 |
| WO | WO-9808871 A1 | 3/1998 |
| WO | WO-9816654 A1 | 4/1998 |
| WO | WO-9824893 A2 | 6/1998 |
| WO | WO-9839446 A2 | 9/1998 |
| WO | WO-9839448 A2 | 9/1998 |
| WO | WO-9846645 A2 | 10/1998 |
| WO | WO-9850433 A2 | 11/1998 |
| WO | WO-9902686 A1 | 1/1999 |
| WO | WO-0000610 A2 | 1/2000 |
| WO | WO-0153312 A1 | 7/2001 |
| WO | WO-0190304 A2 | 11/2001 |
| WO | WO-02058721 A1 | 8/2002 |
| WO | WO-03011213 A2 | 2/2003 |
| WO | WO-03025138 A2 | 3/2003 |
| WO | WO-03029401 A2 | 4/2003 |
| WO | WO-03030835 A2 | 4/2003 |
| WO | WO-03037267 A2 | 5/2003 |
| WO | WO-03060071 A2 | 7/2003 |
| WO | WO-03061712 A1 | 7/2003 |
| WO | WO-03080667 A2 | 10/2003 |
| WO | WO-2004020591 A2 | 3/2004 |
| WO | WO-2004081233 A1 | 9/2004 |
| WO | WO-2005005601 A2 | 1/2005 |
| WO | WO-2005040219 A1 | 5/2005 |
| WO | WO-2005048823 A2 | 6/2005 |
| WO | WO-2005071408 A1 | 8/2005 |
| WO | WO-2005091944 A2 | 10/2005 |
| WO | WO-2005113606 A2 | 12/2005 |
| WO | WO-2006028595 A2 | 3/2006 |
| WO | WO-2006028714 A1 | 3/2006 |
| WO | WO-2006056492 A1 | 6/2006 |
| WO | WO-2006065582 A2 | 6/2006 |
| WO | WO-2006078463 A2 | 7/2006 |
| WO | WO-2006097537 A2 | 9/2006 |
| WO | WO-2006135886 A2 | 12/2006 |
| WO | WO-2006138275 A2 | 12/2006 |
| WO | WO-2007146968 A2 | 12/2007 |
| WO | WO-2008049113 A2 | 4/2008 |
| WO | WO-2008088849 A2 | 7/2008 |
| WO | WO-2008121563 A2 | 10/2008 |
| WO | WO-2009013319 A1 | 1/2009 |
| WO | WO-2009018386 A1 | 2/2009 |
| WO | WO-2009020802 A2 | 2/2009 |
| WO | WO-2009030771 A1 | 3/2009 |
| WO | WO-2009117033 A2 | 9/2009 |
| WO | WO-2009126380 A2 | 10/2009 |
| WO | WO-2009141359 A1 | 11/2009 |
| WO | WO-2010006060 A1 | 1/2010 |
| WO | WO-2010042747 A2 | 4/2010 |
| WO | WO-2010044952 A2 | 4/2010 |
| WO | WO-2010065439 A1 | 6/2010 |
| WO | WO-2010084169 A2 | 7/2010 |
| WO | WO-2010132370 A1 | 11/2010 |
| WO | WO-2010141469 A2 | 12/2010 |
| WO | WO-2010142665 A1 | 12/2010 |
| WO | WO-2011005481 A1 | 1/2011 |
| WO | WO-2011028952 A1 | 3/2011 |
| WO | WO-2011047097 A2 | 4/2011 |
| WO | WO-2011055968 A2 | 5/2011 |
| WO | WO-2011069104 A2 | 6/2011 |

(56) References Cited

FOREIGN PATENT DOCUMENTS

| | | |
|---|---|---|
| WO | WO-2011091078 A2 | 7/2011 |
| WO | WO-2011137362 A1 | 11/2011 |
| WO | WO-2012064733 A2 | 5/2012 |
| WO | WO-2012088290 A2 | 6/2012 |
| WO | WO-2012088302 A2 | 6/2012 |
| WO | WO-2012109624 A2 | 8/2012 |
| WO | WO-2013120554 A1 | 8/2013 |

OTHER PUBLICATIONS

Abcam., Anti-PGRPS antibody [188C424] (ab13903), accessea at http://www.abcam.com/PGRPS-antibody-188C424-ab13903.html accessed on Jun. 12, 2014.
Abcam., Atlas Antibodies, PGRP Antibodies, United States Biologicai, List of Anti-PGRP Abs, accessed at http://www.antibodyresource.com/search/Antibodies/ffb4623f-177 d-13a0-16e2-11 05223fb311/ PG RP accessed on Jan. 8, 2014.
Abcam., Atlas Antibodies, United States Biological, 075594 Antibodies, List of Anti-PGRP Abs, accessed at http://www. antibodyresource. com/search/ Anti bod ies/125bfebf-0922 -1605-3416-8213e4 73b271/07 5594 accessed on Jan. 8, 2014.
Abcam., Atlas Antibodies, United States Biological, Cytokine tag7 Antibodies, List of Anti-PGRP Abs, accessed at http://www. antibodyresource .com/search/ Antibodies/17 a31750-abb9-1 c85-b872-c3a2e 796189c/Cytokine-tag 7 accessed on Jan. 8, 2014.
Abcam., Atlas Antibodies, United States Biological, Peptidoglycan recognition protein 1 Antibodies, List of Anti-PGRP Abs, accessed at http://www.antibodyresource.com/search/Antibodies/1208015d-1757 -26ad-1 f04-6c9171376236/Peptidoglycan- recognition-protein-1 accessed on Jan. 8, 2014.
Abcam., Atlas Antibodies, United States Biological, Peptidoglycan recognition protein 1 Antibodies, List of Anti-PGRP Abs, accessses at http://www.antibodyresource. com/search/A nti bod ies/ede383a0-138e-c073-1710-f9db 1294bc02/Peptidoglycan- recognition-protein-1 accessed on Jan. 8, 2014.
Abcam., Atlas Antibodies, United States Biological Peptidoglycan recognition protein short Antibodies, List of Anti- PGRP Abs accessed on http://www.antibodyresource.com/search/Antibodies/ 3a8d5b63-12d8-12d6-1 b99-11 fb615758f5/Peptidoglycan- recognition-protein-short accessed on Jan. 8, 2014.
Abcam., Atlas Antibodies, United States Biological,Tag7 Antibodies, List of Anti-PGRP Abs accessed at http://www.antibodyresource. com/search/ Anti bod ies/04 1 07168-8402-51 df-bb36-4dd2bf8e 16d 1/Tag accessed on Jan. 8, 2014.
Abcam, Atlas Antibodies, United States Biological,Tag7 Antibodies,List of Anti-PGRP Abs, Retrieved from the Internet< URL:http://www. antibodyresource.com/search/Antibodies/04107f68-8402-51df-bb36-4dd2bf8e16d1/Tag7>, (Accessed Aug. 1, 2014).
Abcam., Atlas Antibodies, United States Biological,TNFSF3L Antibodies, List of Anti-PGRP Abs accessed at http://www.antibodyresource. com/search/Antibodies/f33a5126-45cd-5220-878c-Ofd9aa63ba35/ TNFSF3L accessed on Jan. 8, 2014.
Abravaya, K., et al., "Detection of Point Mutations with a Modified Ligase Chain Reaction (Gap-LCR)," Nucleic Acids Research 23(4):675-682, Oxford University Press, England (Feb. 1995).
Aderem, A. and Ulevitch, R.J., "Toll-like Receptors in the Induction of the Innate Immune Response," Nature 406(6797):782-787, Nature Publishing Group, England (Aug. 2000).
Adrie, C., et al., "Postresuscitation Disease After Cardiac Arrest: A Sepsis-like Syndrome?," Current Opinion in Critical Care 10(3):208-212, Lippincott Williams & Wilkins, United States (Jun. 2004).
Alexander, H.R., et al., "A Recombinant Human Receptor Antagonist to Interleukin 1 Improves Survival After Lethal Endotoxemia in Mice," The Journal of Experimental Medicine 173(4):1029-1032, Rockefeller University Press, United States (Apr. 1991).
Amann, E., et al., "Tightly Regulated Tac Promoter Vectors Useful for the Expression of Unfused and Fused Proteins in *Escherichia coli*," Gene 69(2):301-315, Elsevier/North-Holland, Netherlands (1988).

Amatngalim, G.D., et al., "Cathelicidin Peptide LL-37 Modulates TREM-1 Expression and Inflammatory Responses to Microbial Compounds," Inflammation 34(5):412-425, Kluwer Academic/ Plenum Publishers, United States (Oct. 2011).
Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).
Angal, S., et al., "A Single Amino Acid Substitution Abolishes the Heterogeneity of Chimeric Mouse/Human (IgG4) Antibody," Molecular Immunology 30(1):105-108, Pergamon Press, England (Jan. 1993).
Appelmelk, B.J., et al., "Use of Mucin and Hemoglobin in Experimental Murine Gram-negative Bacteremia Enhances the Immunoprotective Action of Antibodies Reactive With the Lipopolysaccharide Core Region," Antonie van Leeuwenhoek 52(6):537-542, Springer, Netherlands (1986).
Arnon, et al., "Monoclonal Antibodies for Immunotargeting of Drugs in Cancer Therapy," in Monoclonal Antibodies and Cancer Therapy, Reisfeld et al., eds., Alan R. Liss, Inc., (1985), pp. 243-256.
Arts, R.J., et al., "TREM-1 Interaction with the LPS/TLR4 Receptor Complex," European Cytokine Network 22(1):11-14, John Libbey Eurotext Ltd, France (2011).
Attwood, T.K., "Genomics. The Babel of Bioinformatics," Science 290(5491):471-473, American Association for the Advancement of Science, United States (Oct. 2000).
Bakker, A.B., et al., "DAP12-deficient Mice Fail to Develop Autoimmunity Due to Impaired Antigen Priming," Immunity 13(3):345-353, Cell Press, United States (Sep. 2000).
Bakker, A.B., et al., "Myeloid DAP12-associating Lectin (MDL)-1 is a Cell Surface Receptor Involved in the Activation of Myeloid Cells," Proceedings of the National Academy of Sciences 96(17):9792-9796, National Academy of Sciences, United States (Aug. 1999).
Bakker, A.B., et al., "NK Cell Activation: Distinct Stimulatory Pathways Counterbalancing Inhibitory Signals," Human Immunology 61(1):18-27, Elsevier/North-Holland, United States (Jan. 2000).
Baldari, C., et al., "A Novel Leader Peptide Which Allows Efficient Secretion of a Fragment of Human Interleukin 1 Beta in Saccharomyces Cerevisiae," The EMBO Journal 6(1):229-234, Wiley Blackwell, England (Jan. 1987).
Baldwin, et al., "Analysis Results, and Future Prospective of the Therapeutic Use of the Radiolabeled Antibody in Cancer Therapy," in Monoclonal Antibodies for Cancer Detection and Therapy, eds. Adacemic Press, pp. 303-316 (1985).
Banerji, J., et al., "A Lymphocyte-specific Cellular Enhancer Is Located Downstream of the Joining Region in Immunoglobulin Heavy Chain Genes," Cell 33(3):729-740, Cell Press, United States (Jul. 1983).
Barany, F., "Genetic Disease Detection and Dna Amplification Using Cloned Thermostable Ligase," Proceedings of the National Academy of Sciences 88(1):189-193, National Academy of Sciences, United States (Jan. 1991).
Bartel, D.P. and Szostak, J.W., "Isolation of New Ribozymes From a Large Pool of Random Sequences," Science 261(5127):1411-1418, American Association for the Advancement of Science, United States (Sep. 1993).
Bartel, P. "Elimination of false positives that arise in using the two-hybrid system," Biotechniques 14(6):920-924, (1993).
Basic Methods in Molecular Biology, Elsevier Science Publishing Co., New York, (1986), pp. 75-78 and 84-87.
Bauer, S., et al., "Activation of NK Cells and T Cells by NKG2D, a Receptor for Stress-inducible MICA," Science 285(5428):727-729, American Association for the Advancement of Science, United States (Jul. 1999).
Begum, N.A., et al., "Mycobacterium Bovis Bcg Cell Wall-specific Differentially Expressed Genes Identified by Differential Display and cDNA Subtraction in Human Macrophages," Infection and Immunity 72(2):937-948, American Society for Microbiology, United States (Feb. 2004).
Benda, P., et al., "Differentiated Rat Glial Cell Strain in Tissue Culture," Science 161(3839):370-371, American Association for the Advancement of Science, United States (Jul. 1968).

(56) References Cited

OTHER PUBLICATIONS

Better, M., et al., "*Escherichia coli* Secretion of an Active Chimeric Antibody Fragment," Science 240(4855):1041-1043, Association for the Advancement of Science, United States (May 1988).
Beutler, B., "Endotoxin, Toll-like Receptor 4, and the Afferent Limb of Innate Immunity," Current opinion in microbiology 3(1):23-28, Current Biology, England (Feb. 2000).
Beutler, B., et al., "Passive Immunization Against Cachectin/tumor Necrosis Factor Protects Mice From Lethal Effect of Endotoxin," Science 229(4716):869-871, American Association for the Advancement of Science, United States (Aug. 1985).
Bird, R.E., et al., "Single-chain Antigen-binding Proteins," Science 242(4877):423-426, Association for the Advancement of Science, United States (Oct. 1988).
Bleharski, J.R., et al., "A Role for Triggering Receptor Expressed on Myeloid Cells-1 in Host Defense During the Early-induced and Adaptive Phases of the Immune Response," Journal of Immunology 170(7):3812-3818, American Association of Immunologists, United States (Apr. 2003).
Boesen, J.J., et al., "Circumvention of Chemotherapy-induced Myelosuppression by Transfer of the mdr1 Gene," Biotherapy 6(4):291-302, Kluwer Academic Publishers, Netherlands (1993).
Bolin, S.R., et al., "Survey of Cell Lines in the American Type Culture Collection for Bovine Viral Diarrhea Virus," Journal of Virological Methods 48(2-3):211-221, Elsevier/North-Holland Biomedical Press, Netherlands (Jul. 1994).
Bone, R.C., et al., "Definitions for Sepsis and Organ Failure and Guidelines for the Use of Innovative Therapies in Sepsis. The ACCP/SCCM Consensus Conference Committee. American College of Chest Physicians/Society of Critical Care Medicine," Chest 101(6):1644-1655, Elsevier, United States (Jun. 1992).
Bone, R.C., "The Pathogenesis of Sepsis," Annals of Internal Medicine 115(6):457-469, American College of Physicians, United States (Sep. 1991).
Bordelon-Riser, M.E., "Necessity for Two Human Chromosomes for Human Chorionic Gonadotropin Production in Human-mouse Hybrids," Somatic Cell Genetics 5(5):597-613, Plenum, United States (Sep. 1979).
Bork, P. and Bairoch, A., "Go Hunting in Sequence Databases but Watch out for the Traps," Trends in Genetics 12(10):425-427, Elsevier Trends Journals, England (Oct. 1996).
Bork, P., "Powers and Pitfalls in Sequence Analysis: The 70% Hurdle," Genome Research 10(4):398-400, Cold Spring Harbor Laboratory Press, United States (Apr. 2000).
Bostanci, N., et al., "Involvement of the TREM-1/DAP12 Pathway in the Innate Immune Responses to Porphyromonas Gingivalis," Molecular Immunology 49(1-2):387-394, Pergamon Press, England (Oct. 2011).
Bouchon, A., et al., "Cutting Edge: Inflammatory Responses Can Be Triggered by TREM-1, A Novel Receptor Expressed on Neutrophils and Monocytes," Journal of Immunology 164(10):4991-4995, American Association of Immunologists, United States (2000).
Bouchon, A., et al., "TREM-1 Amplifies Inflammation and is a Crucial Mediator of Septic Shock," Nature 410(6832):1103-1107, Nature Publishing Group, England (2001).
Bout, A., et al., "Lung Gene Therapy: In Vivo Adenovirus-mediated Gene Transfer to Rhesus Monkey Airway Epithelium," Human Gene Therapy 5(1):3-10, Liebert, United States (Jan. 1994).
Bradley, A., "Modifying the Mammalian Genome by Gene Targeting," Current Opinion in Biotechnology 2(6):823-829, Elsevier, England (Dec. 1991).
Bradley, "Teratocarcinomas and Embryonic Stem Cells: A Practical Approach," Robertson, ed., IRL, Oxford, pp. 113-152 (1987).
Brenner, S.E., "Errors in Genome Annotation," Trends in Genetics 15(4):132-133, Elsevier Trends Journals, England (Apr. 1999).
Brinkmann, U., et al., "Phage Display of Disulfide-stabilized Fv Fragments," Journal of Immunological Methods 182(1):41-50, Elsevier, Netherlands (1995).
Burton, D.R. and Barbas, C.F. 3rd., "Human Antibodies From Combinatorial Libraries," Advances in Immunology 57:191-280, Academic Press, United States (1994).
Byrne, G.W. and Ruddle, F.H., "Multiplex Gene Regulation: a Two-tiered Approach to Transgene Regulation in Transgenic Mice," Proceedings of the National Academy of Sciences USA 86(14):5473-5477 (Jul. 1989).
Calame, K., et al., "Transcriptional Controlling Elements in the Immunoglobulin and T Cell Receptor Loci," Advances in Immunology 43:235-275 (1988).
Calandra, T., et al, "Protection From Septic Shock by Neutralization of Macrophage Migration Inhibitory Factor," Nature Medicine 6(2):164-170, Nature Publishing Company, United States (2000).
Camper, S.A. and Tilghman, S.M., "Postnatal Repression of the Alpha-fetoprotein Gene is Enhancer Independent," Genes & Development 3:537-546 (1989).
Cantoni, C., et al., "Nkp44, a Triggering Receptor Involved in Tumor Cell Lysis by Activated Human Natural Killer Cells, Is a Novel Member of the Immunoglobulin Superfamily," Journal of Experimental Medicine 189(5):787-796, Rockefeller University Press, United States (Mar. 1999 ).
Carrell., et al., "A Novel Procedure for the Synthesis of Libraries Containing Small Organic Molecules," Angewandte Chemie International Edition in English 33:2059-2061, (1994).
Casset, F., et al., "A Peptide Mimetic of an Anti-CD4 Monoclonal Antibody by Rational Design," Biochemical and Biophysical Research Communications 307(1):198-205, Academic Press,United States (Jul. 2003).
Cella, M., et al., "A Novel Inhibitory Receptor (ILT3) Expressed on Monocytes, Macrophages, and Dendritic Cells Involved in Antigen Processing," Journal of Experimental Medicine 185(10):1743-1751, Rockefeller University Press, United States (May 1997 ).
Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (Nov. 1999).
Cho, C.Y., et al., "An unnatural biopolymer," Science 261(5126):1303-1305, American Association for the Advancement of Science, United States (1993).
Cho, J.H., et al., "Human Peptidoglycan Recognition Protein S is an Effector of Neutrophil-mediated Innate Immunity," Blood 106(7):2551-2558, American Society of Hematology, United States (Oct. 2005).
Chomel, B.B., et al., "Bartonella Henselae Prevalence in Domestic Cats in California: Risk Factors and Association Between Bacteremia and Antibody Titers," Journal of Clinical Microbiology 33(9):2445-2450, American Society for Microbiology, United States (Sep. 1995).
Chothia, C. and Lesk, A.M., "Canonical Structures for the Hypervariable Regions of Immunoglobulins," Journal of Molecular Biology 196(4):901-917, Elsevier Science, United States (Aug. 1987).
Clowes, M.M., et al., "Long-term Biological Response of Injured Rat Carotid Artery Seeded With Smooth Muscle Cells Expressing Retrovirally Introduced Human Genes," The Journal of Clinical Investigation 93(2):644-651, American Society for Clinical Investigation, United States (Feb. 1994).
Cohen, A.S., et al., "Emerging Technologies for Sequencing Antisense Oligonucleotides: Capillary Electrophoresis and Mass Spectrometry," Advances in Chromatography 36:127-162, CRC Press, United States (1996).
Cohen, J., "The Immunopathogenesis of Sepsis," Nature 420(6917):885-891, Nature Publishing Group, England (Dec. 2002).
Cohen, J., "TREM-1 in Sepsis," Lancet 358(9284):776-778, Elsevier, England (Sep. 2001).
Colbere-Garapin, F., et al., "A New Dominant Hybrid Selective Marker for Higher Eukaryotic Cells," Journal of Molecular Biology 150(1):1-14, Elsevier, England (Jul. 1981).
Collart, M.A., et al., "Regulation of Tumor Necrosis Factor Alpha Transcription in Macrophages: Involvement of Four Kappa B-like Motifs and of Constitutive and Inducible Forms of NF-kappa B,"

(56) References Cited

OTHER PUBLICATIONS

Molecular and Cellular Biology 10(4):1498-1506, American Society for Microbiology, United States (Apr. 1990).
Colonna, M. and Facchetti, F., "TREM-1 (Triggering Receptor Expressed on Myeloid Cells): A New Player in Acute Inflammatory Responses," The Journal of Infectious Diseases 187(2):S397-S401, Oxford University Press, United States (Jun. 2003).
Colonna, M., "TREMS in the Immune System and Beyond," Nature Reviews. Immunology 3(6):445-453, Nature Pub. Group, England (Jun. 2003).
Coskun, T., et al., "Fibroblast Growth Factor 21 Corrects Obesity in Mice," Endocrinology 149(12):6018-6027, Oxford University Press, United States (Dec. 2008).
Cotten, M., et al., "Receptor-mediated Transport of DNA Into Eukaryotic Cells," Methods in Enzymology 217:618-644, Academic Press, United States (1993).
Cotton, R.G., "Current Methods of Mutation Detection," Mutation Research 285(1):125-144, Elsevier, Netherlands (Jan. 1993).
Cotton, R.G., et al., "Reactivity of Cytosine and Thymine in Single-base-pair Mismatches With Hydroxylamine and Osmium Tetroxide and Its Application to the Study of Mutations," Proceedings of the National Academy of Sciences 85(12):4397-4401, National Academy of Sciences, United States (Jun. 1988).
Cox, G., et al., "IL-10 Enhances Resolution of Pulmonary Inflammation in Vivo by Promoting Apoptosis of Neutrophils," The American Journal of Physiology 271(4 Pt 1):L566-L571, American Physiological Society, United States (Oct. 1996).
Cronin, M.T., et al., "Cystic Fibrosis Mutation Detection by Hybridization to Light-generated DNA Probe Arrays," Human Mutation 7(3):244-255, Wiley-Liss, United States (1996).
Cruikshank, W.W., et al., "A Lipidated Anti-Tat Antibody Enters Living Cells and Blocks HIV-1 Viral Replication," Journal of Acquired Immune Deficiency Syndromes and Human Retrovirology 14(3):193-203, Lippincott Williams & Wilkins, United States (Mar. 1997).
Cull, M.G., et al., "Screening for Receptor Ligands Using Large Libraries of Peptides Linked to the C Terminus of the Lac Repressor," Proceedings of the National Academy of Sciences 89(5):1865-1869, National Academy of Sciences, United States (Mar. 1992).
Cwirla, S.E., et al., "Peptides on phage: a vast library of peptides for identifying ligands," Proceedings of the National Academy of Sciences 87(16):6378-6382, National Academy of Sciences, United States, (1990).
Database EMBL, Sequence from Patent WO200283856-A2, Sep. 17, 2003 "Human G-protein Coupled Receptor Phosphorylation Site Peptide SEQ ID 131," retrieved from EBI Database accession No. ABJ38803.
Database EMBL, Sequence Information from JP2000116377-A, Oct. 10, 2000 "N-terminus of Porcine Trypsin," retrieved from EBI Database accession No. AAB03087.
Davenport, C.M., et al., "Inhibition of Pro-inflammatory Cytokine Generation by CTLA4-Ig in the Skin and Colon of Mice Adoptively Transplanted with CD45RBhi CD4+ T Cells Correlates with Suppression of Psoriasis and Colitis," International Immunopharmacology 2(5):653-672, Elsevier Science, Netherlands (2002).
Daws, M.R., et al., "Cloning and Characterization of a Novel Mouse Myeloid DAP12-associated Receptor Family," European Journal of Immunology 31(3):783-791, Wiley-VCH, Germany (Mar. 2001).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Devlin, J.J., et al., "Random peptide libraries: a source of specific protein binding molecules," Science 249(4967):404-406, American Association for the Advancement of Science, United States (1990).
Dewitt, S.H., et al., "Diversomers: an approach to nonpeptide, nonoligomeric chemical diversity," Proceedings of the National Academy of Sciences 90(15):6909-6913, National Academy of Sciences, United States (1993).
Dietrich, J., et al., "Cutting Edge: Signal-regulatory Protein Beta 1 is a DAP12-associated Activating Receptor Expressed in Myeloid Cells," Journal of Immunology 164(1):9-12, American Association of Immunologists, United States (Jan. 2000).
Dinarello, C.A., "Proinflammatory and Anti-inflammatory Cytokines as Mediators in the Pathogenesis of Septic Shock," Chest 112(6):3215-3295, Elsevier, United States (Dec. 1997).
Doerks T., et al., "Protein Annotation: Detective Work for Function Prediction," Trends in Genetics 14(6):248-250, Elsevier Trends Journals, England (Jun. 1998).
Downey, G.P., et al., "Intracellular Signaling in Neutrophil Priming and Activation," Seminars in Cell Biology 6(6):345-356, Academic Press, England (Dec. 1995).
Dziarski, R., et al., "Peptidoglycan Recognition in Innate Immunity," Endotoxin Research 11(5):304-310, Sage Publications, United States (2005).
Dziarski, R., et al., "Review: Mammalian Peptidoglycan Recognition Proteins (PGRPs) in Innate Immunity," Innate Immunity 16(3):168-174, Sage Publications, United States (Jun. 2010).
Dziarski, R., Gupta, D., "The Peptidoglycan Recognition Proteins (PGRPs)," Genome Biology 7(8):232.1-232.13, BioMed Central Ltd, England (2006).
Dziarski, R., "Peptidoglycan Recognition Proteins (PGRPS)," Molecular Immunology 40(12):877-886, Pergamon Press, England (Feb. 2004).
Echtenacher, B., et al., "Critical Protective Role of Mast Cells in a Model of Acute Septic Peritonitis," Nature 381(6577):75-77, Nature Publishing Group, England (May 1996).
Echtenacher, B., et al., "Requirement of Endogenous Tumor Necrosis Factor/cachectin for Recovery From Experimental Peritonitis," Journal of Immunology 145(11):3762-3766, American Association of Immunologists, United States (Dec. 1990).
Echtenacher, B., et al., "Tumor Necrosis Factor-dependent Adhesions as a Major Protective Mechanism Early in Septic Peritonitis in Mice," Infection and Immunity 69(6):3550-3555, American Society for Microbiology, United States (Jun. 2001).
Edlund, T., et al., "Cell-specific Expression of the Rat Insulin Gene: Evidence for Role of Two Distinct 5' Flanking Elements," Science 230(4728):912-916, American Association for the Advancement of Science, United States (Nov. 1985).
Erb, E., et al., "Recursive deconvolution of combinatorial chemical libraries," Proceedings of the National Academy of Sciences 91(24):11422-11426, National Academy of Sciences, United States (1994).
Erickson, S.K., "Nonalcoholic Fatty Liver Disease," Journal of Lipid Research 50:S412-S416, American Society for Biochemistry and Molecular Biology, United States (Apr. 2009).
Eskandari, M.K., et al., "Anti-tumor Necrosis Factor Antibody Therapy Fails to Prevent Lethality After Cecal Ligation and Puncture or Endotoxemia," Journal of Immunology 148(9):2724-2730, American Association of Immunologists, United States (May 1992).
Facchetti, F., et al., "Suppurative Granulomatous Lymphadenitis. Immunohistochemical Evidence for a B-cell-associated Granuloma," The American Journal of Surgical Pathology 16(10):955-961, Wolters Kluwer Health, Inc., United States (Oct. 1992).
Felici, F., et al., "Selection of Antibody Ligands from a Large Library of Oligopeptides Expressed on a Multivalent Exposition Vector," Journal of Molecular Biology 222(2):301-310, Elsevier Science, United States (Nov. 1991).
Fell, H.P., et al., "Genetic Construction and Characterization of a Fusion Protein Consisting of a Chimeric F(ab') With Specificity for Carcinomas and Human IL-2," Journal of Immunology 146(7):2446-2452, American Association of Immunologists, United States (Apr. 1991).
Fiering, S., et al., "Single Cell Assay of a Transcription Factor Reveals a Threshold in Transcription Activated by Signals Emanating From the T-cell Antigen Receptor," Genes & Development 4(10):1823-1834, Cold Spring Harbor Laboratory Press, United States (1990).

(56) References Cited

OTHER PUBLICATIONS

Finn, P.J., et al., "Synthesis and Properties of DNA-PNA Chimeric Oligomers," Nucleic Acids Research 24(17):3357-3363, Oxford University Press, England (Sep. 1996).
Fisher, C.J., et al., "Treatment of Septic Shock with the Tumor Necrosis Factor Receptor: Fc Fusion Protein the Soluble TNF Receptor Sepsis Study Group," The New England Journal of Medicine 334(26):1697-1702, Massachusetts Medical Society, United States (Jun. 1996).
Fodor, S.P., et al., "Multiplexed biochemical assays with biological chips," Nature 364(6437):555-556, Nature Publishing Group, United States (1993).
Forster, R., et al., "CCR7 Coordinates the Primary Immune Response by Establishing Functional Microenvironments in Secondary Lymphoid Organs," Cell 99(1):23-33, Cell Press, United States (Oct. 1999).
Gallop, M.A., et al., "Applications of combinatorial technologies to drug discovery. 1. Background and peptide combinatorial libraries," Journal of Medicinal Chemistry 37(9):1233-1251, (1994).
Gasparini, P., et al., "Restriction Site Generating-polymerase Chain Reaction (RG-PCR) for the Probeless Detection of Hidden Genetic Variation: Application to the Study of Some Common Cystic Fibrosis Mutations," Molecular and Cellular Probes 6(1):1-7, Academic Press, England (Feb. 1992).
Gautier, C., et al., "alpha-DNA Iv: alpha-anomeric and beta-anomeric Tetrathymidylates Covalently Linked to Intercalating Oxazolopyridocarbazole Synthesis, Physicochemical Properties and Poly," Nucleic Acids Research 15(16):6625-6641, Oxford University Press, England (Aug. 1987).
GenBank, "AL681036 XGC-gastrula Xenopus tropicalis cDNA clone TGas068103 5-, mRNA sequence," Accession No. AL681036. 2, accessed at https://www.ncbi.nlm.nih.gov/nucest/AI681036, Nov. 10, 2003.
GenBank, "AL962750 XGC-gastrula Xenopus tropicalis cDNA clone TGas109m03 5-, mRNA sequence," Accession No. AL962750. 2, accessed at https://www.ncbi.nlm.nih.gov/nucest/AI962750, Dec. 5, 2003.
GenBank, "AL968134 XGC-gastrula Xenopus tropicalis cDNA clone TGas113h24 5-, mRNA sequence," Accession No. AL968134. 2, accessed at https://www.ncbi.nlm.nih.gov/nucest/AI968134, Dec. 5, 2003.
GenBank, "Cloning Vector pIRES1hyg, Complete Plasmid Sequence," Accession No. U89672.1, accessed at https://www.ncbi.nlm.nih.gov/nuccore/U89672, Mar. 21, 1997.
GenBank, "CM0-TT0011-251099-080405 TT0011 Homo sapiens cDNA, mRNA sequence," Accession No. AW394041.1, accessed at https://www.ncbi.nlm.nih.gov/nucest/AW394041, Feb. 4, 2000.
GenBank, "Homo sapiens triggering receptor expressed on monocytes 1 mRNA, complete cds," Accession No. AF196329.1, accessed at https://www.ncbi.nlm.nih.gov/nuccore/AF196329, May 24, 2000.
GenBank, "Homo Sapiens Triggering Receptor Expressed on Myeloid Cells 1 (TREM1), mRNA," Accession No. NM_018643.2, accessed at https://www.ncbi.nlm.nih.gov/nuccore/NM_018643.2, May 15, 2011.
GenBank, "Homo sapiens triggering receptor expressed on myeloid cells 2 mRNA, complete cds," Accession No. AF213457.1, accessed at https://www.ncbi.nlm.nih.gov/nuccore/AF213457, May 23, 2000.
GenBank, "HUM517F10B Human placenta polyA+ (TFujiwara) Homo sapiens cDNA clone GEN-517F10 5-, mRNA sequence," Accession No. D78812.1, accessed at https://www.ncbi.nlm.nih.gov/nucest/D78812, Jul. 20, 2006.
GenBank, "ne55f09.s1 NCI_CGAP_Co3 Homo sapiens cDNA clone IMAGE:901289 3-, mRNA sequence," Accession No. AA494171.1, accessed at https://www.ncbi.nlm.nih.gov/nucest/AA494171, Jan. 6, 2011.
GenBank, "T3 end of clone 024CH09 of library SmBAC1 from strain Puerto-Rican of Schistosoma mansoni, genomic survey sequence," Accession No. AL621023.1, accessed at https://www.ncbi.nlm.nih.gov/nucgss/AI621023, Oct. 11, 2001.
GenBank, "T3 end of clone AR0AA015A03 of library AR0AA from strain CBS 732 of Zygosaccharomyces rouxii, genomic survey sequence," Accession No. AL394092.1, accessed at https://www.ncbi.nlm.nih.gov/nucgss/AI394092, Feb. 16, 2014.
GenBank, "tb95h04.x1 NCI_CGAP_Co16 Homo sapiens cDNA clone IMAGE:2062135 3-, mRNA sequence," Accession No. AI337247. 1, accessed at https://www.ncbi.nlm.nih.gov/nucest/AI337247, Jan. 8, 2011.
GenBank, "Tetraodon nigroviridis genome survey sequence T7 end of clone 245F13 of library G from Tetraodon nigroviridis, genomic survey sequence," Accession No. AL186456, accessed at https://www.ncbi.nlm.nih.gov/nucgss/AI186456, May 19, 2010.
GenBank, "UI-H-BI1-acf-g-10-0-UI.s1 NCI_CGAP_Sub3 Homo sapiens cDNA clone IMAGE:2714299 3-, mRNA sequence," Accession No. AW135801.1, accessed at https://www.ncbi.nlm.nih.gov/nucest/AW135801, Jan. 6, 2011.
GenBank, "UI-H-BI1-ada-h-08-0-UI.s1 NCI_CGAP_Sub3 Homo sapiens cDNA clone IMAGE:2716286 3-, mRNA sequence," Accession No. AW139363.1, accessed at https://www.ncbi.nlm.nih.gov/nucest/AW139363, Jan. 7, 2011.
GenBank, "UI-H-BI1-aea-d-11-0-UI.s1 NCI_CGAP_Sub3 Homo sapiens cDNA clone IMAGE:2718764 3-, mRNA sequence," Accession No. AW139572.1, accessed at https://www.ncbi.nlm.nih.gov/nucest/AW139572, Jan. 7, 2011.
GenBank, "UI-H-BI1-aea-d-12-0-UI.s1 NCI_CGAP_Sub3 Homo sapiens cDNA clone IMAGE:2718766 3-, mRNA sequence," Accession No. AW139573.1, accessed at https://www.ncbi.nlm.nih.gov/nucest/AW139573, Oct. 30, 1999.
GenBank, "xm62e07.x1 NCI_CGAP_GC6 Homo sapiens cDNA clone IMAGE:2688804 3-, mRNA sequence," Accession No. AW274906.1, accessed at https://www.ncbi.nlm.nih.gov/nucest/AW274906, Jan. 3, 2000.
GenBank, "yw70g03.r1 Soares_placenta_8to9weeks_2NbHP8to9W Homo sapiens cDNA clone IMAGE:257620 5-, mRNA sequence," Accession No. N41388.1, accessed at https://www.ncbi.nlm.nih.gov/nucest/N41388, Jan. 24, 1996.
GenBank, "zk87c02.r1 Soares_pregnant_uterus_NbHPU Homo sapiens cDNA clone IMAGE:489794 5-, mRNA sequence," Accession No. AA099288.1, accessed at https://www.ncbi.nlm.nih.gov/nucest/AA099288, Jan. 28, 2011.
GenBank, "zk87c02.s1 Soares_pregnant_uterus_NbHPU Homo sapiens cDNA clone IMAGE:489794 3-, mRNA sequence," Accession No. AA101983.1, accessed at https://www.ncbi.nlm.nih.gov/nucest/AA101983, Jan. 28, 2011.
Gencic, S. And Hudson, L.D., "Conservative Amino Acid Substitution in the Myelin Proteolipid Protein of Jimpymsd Mice," The Journal of Neuroscience 10(1):117-124, Society for Neuroscience, United States (Jan. 1990).
Gentz, R., et al., "Bioassay for Trans-activation using Purified Human Immunodeficiency Virus Tat-encoded Protein: Trans-activation Requires mRNA Synthesis," Proceedings of the National Academy of Sciences USA 86(3):821-824, National Academy of Sciences, United States (Feb. 1989).
Ghosh, A., et al., "A Novel Antimicrobial Peptidoglycan Recognition Protein in the Cornea," Investigative Ophthalmology & Visual Science 50(9):4185-4191, Association for Research in Vision and Ophthalmology, United States (Sep. 2009).
Gibbs, R.A., et al., "Detection of Single DNA Base Differences by Competitive Oligonucleotide Priming," Nucleic Acids Research 17(7):2437-2448, Oxford University Press, England (Apr. 1989).
Gibot, S., et al., "A Soluble Form of the Triggering Receptor Expressed on Myeloid Cells-1 Modulates the Inflammatory Response in Murine Sepsis," The Journal of Experimental Medicine 200(11):1419-1426, Rockefeller University Press, United States (Dec. 2004).
Gibot, S., et al., "Modulation of the Triggering Receptor Expressed on the Myeloid Cell Type 1 Pathway in Murine Septic Shock," Infection and immunity 74(5):2823-2830, American Society for Microbiology, United States (May 2006).
Gibot, S., et al., "Soluble Triggering Receptor Expressed on Myeloid Cells and the Diagnosis of Pneumonia," The New England Journal of Medicine 350(5):451-458, Massachusetts Medical Society, United States (Jan. 2004).

(56) References Cited

OTHER PUBLICATIONS

Gibot, S., et al., "Plasma Level of a Triggering Receptor Expressed on Myeloid Cells-1: its Diagnostic Accuracy in Patients with Suspected Sepsis," Annals of Internal Medicine 141(1):9-15, American College of Physicians-American Society of Internal Medicine, United States (Jul. 2004).
Gillies, S.D., et al., "Antibody-targeted Interleukin 2 Stimulates T-cell Killing of Autologous Tumor Cells," Proceedings of the National Academy of Sciences of the United States of America 89(4):1428-1432, National Academy of Sciences, United States (1992).
Gillies, S.D., et al., "High-level Expression of Chimeric Antibodies Using Adapted cDNA Variable Region Cassettes," Journal of Immunological Methods 125(1-2):191-202, Elsevier, Netherlands (1989).
Gingras, M.C., et al., "TREM-1, MDL-1, and DAP12 Expression is Associated with a Mature Stage of Myeloid Development," Molecular Immunology 38(11):817-824, Pergamon Press, England (Mar. 2002).
Glauser, M.P., et al., "Septic Shock: Pathogenesis," Lancet 338(8769):732-736, Elsevier, England (Sep. 1991).
Goldspiel, B.R., et al., "Human Gene Therapy," Clinical Pharmacy 12(7):488-505, American Society of Hospital Pharmacists, United States (1993).
Gon, S., et al., "Involvement of Two Types of TNF Receptor in TNF-alpha Induced Neutrophil Apoptosis," Microbiology and Immunology 40(6):463-465, Wiley-Blackwell, Australia (1996).
Griffin, H.G. and Griffin, A.M., "DNA Sequencing. Recent Innovations and Future Trends," Applied Biochemistry and Biotechnology 38(1-2):147-159, Humana Press, United States (Jan.-Feb. 1993).
Griffin, M.P., et al., "Abnormal Heart Rate Characteristics Preceding Neonatal Sepsis and Sepsis-like Illness," Pediatric Research 53(6):920-926, Nature Publishing Group, United States (Jun. 2003).
Grossman, M. and Wilson, J.M., "Retroviruses: Delivery Vehicle to the Liver," Current Opinion in Genetics & Development 3(1):110-114, Elsevier, England (Feb. 1993).
Grundy, S.M., et al., "Definition of Metabolic Syndrome: Report of the National Heart, Lung, and Blood Institute/American Heart Association Conference on Scientific Issues Related to Definition," Circulation 109(3):433-438, Lippincott Williams & Wilkins, United States (Jan. 2004).
Guan, R., et al., "Crystal Structure of Human Peptidoglycan Recognition Protein S (PGRP-S) at 1.70 A Resolution," Molecular Biology 347(4):683-691, Elsevier, England (Apr. 2005).
Guatelli, J.C., et al., "Isothermal, in Vitro Amplification of Nucleic Acids by a Multienzyme Reaction Modeled After Retroviral Replication ," Proceedings of the National Academy of Sciences 87(5):1874-1878, National Academy of Sciences, United States (Mar. 1990).
Haapala, D.K., et al., "Isolation From Cats of an Endogenous Type C Virus With a Novel Envelope Glycoprotein," Journal of Virology 53(3):827-833, American Society for Microbiology, United States (Mar. 1985).
Hammerling, G.J., et al., "Monoclonal Antibodies and T-Cell Hybridomas," pp. 563-681, Elsevier, Newyork (1981).
Harlow, E. and Lane, D., Antibodies: A Laboratory Manual, 2nd Edition, Cold Spring Harbor Press (1988).
Haselmayer, P., et al., "TREM-1 Ligand Expression on Platelets Enhances Neutrophil Activation," Blood 110(3):1029-1035, American Society of Hematology, United States (Aug. 2007).
Haseloff, J., et al., "Simple RNA Enzymes with New and Highly Specific Endoribonuclease Activities," Nature 334(6183):585-591, Nature Publishing Group, England (Aug. 1988).
Hayashi, K., "PCR-SSCP: A Method for Detection of Mutations," Genetic Analysis, Techniques and Applications 9(3):73-79, Elsevier, Netherlands (Jun. 1992).
He, X.M., et al., "Expression of 06-methylguanine-DNA Methyltransferase in Six Human Medulloblastoma Cell Lines," Cancer Research 52(5):1144-1148, American Association for Cancer Research, United States (Mar. 1992).
Hebert, M.J., et al., "Sequential Morphologic Events During Apoptosis of Human Neutrophils. Modulation by Lipoxygenase-derived Eicosanoids," Journal of Immunology 157(7):3105-3115, American Association of Immunologists, United States (Oct. 1996).
Helene, C., et al., "Control of Gene Expression by Triple Helix-forming Oligonucleotides. The Antigene Strategy," Annals of the New York Academy of Sciences 660:27-36, Blackwell, United States (Oct. 1992).
Helene, C., "The Anti-gene Strategy: Control of Gene Expression by Triplex-forming-oligonucleotides," Anti-cancer Drug Design 6(6):569-584, Oxford University Press, United States (1991).
Hellstrom, et al., "Antibodies for Drug Delivery" in Controlled Drug Delivery, 2nd edition, Robinson et al., eds., Marcel Dekker, Inc., (1987), pp. 623-653.
Hiscott, J., et al., "Characterization of a Functional NF-kappa B Site in the Human Interleukin 1 Beta Promoter: Evidence for a Positive Autoregulatory Loop," Molecular and Cellular Biology 13(10):6231-6240, American Society for Microbiology, United States (Oct. 1993).
Hoffmann, J.A., et al., "Phylogenetic Perspectives in Innate Immunity," Science 284(5418):1313-1318, American Association for the Advancement of Science, United States (May 1999).
Holliger, P, and Hudson, P.J., "Engineered Antibody Fragments and the Rise of Single Domains," Nature Biotechnology 23(9):1126-1136, Nature America Publishing, United States (2005).
Hotchkiss, R.S. and Karl, I.E., "The Pathophysiology and Treatment of Sepsis," The New England Journal of Medicine 348(2):138-150, Massachusetts Medical Society, United States (Jan. 2003).
Houghten, R.A., et al., "The Use of Synthetic Peptide Combinatorial Libraries for the Identification of Bioactive Peptides," Biotechniques 13(3):412-421, Informa Healthcare USA, England (Sep. 1992).
Hsu, I.C., et al., "Detection of DNA Point Mutations with DNA Mismatch Repair Enzymes," Carcinogenesis 15(8):1657-1662, Irl Press, England (Aug. 1994).
Human PGLYRP1/PGRP-S Antibody AF2590: R&D Systems, accessed at https://www.rndsystems.com/products/human-pglyrp1-pgrp-s- antibody_af2590 accessed on Mar. 29, 2018.
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).
Huston, J.S., et al., "Protein Engineering of Single-chain Fv Analogs and Fusion Proteins," Methods in Enzymology 203:46-88, Academic Press, United States (1991).
Hybridization with Radioactive Probes, Current Protocols in Molecular Biology, John Wiley & Sons, N.Y. 6.3.1-6.3.6 (1989).
Hyrup, B. and Nielsen, P.E., "Peptide Nucleic Acids (PNA): Synthesis, Properties and Potential Applications," Bioorganic & Medicinal Chemistry 4(1):5-23, Elsevier Science, England (Jan. 1996).
Ill, C.R., et al., "Design and Construction of a Hybrid Immunoglobulin Domain With Properties of Both Heavy and Light Chain Variable Regions," Protein Engineering 10(8):949-957, IRL Press, England (1997).
Inoue, H., et al., "Sequence-dependent Hydrolysis of RNA using Modified Oligonucleotide Splints and RNase H," FEBS letters 215(2):327-330, Elsevier Science B.V, Netherlands (May 1987).
Inoue, H., et al., "Synthesis and Hybridization Studies on Two Complementary Nona(2'-O-Methyl)Ribonucleotides," Nucleic Acids Research 15(15):6131-6148, Oxford University Press, England (Aug. 1987).
International Preliminary Report on Patentability and Written Opinion Application No. PCT/EP2012/074093, European Patent Office, Iceland, dated Aug. 19, 2014, 8 pages.
International Search for International Application No. PCT/EP2012/074093, European Patent Office, Iceland dated May 7, 2013, 5 pages
Iwabuchi, K., et al., "Use of the two-hybrid system to identify the domain of p53 involved in oligomerization," Oncogene 8(6):1693-1696, (1993).
Jespers, L.S., et al., "Guiding the Selection of Human Antibodies from Phage Display Repertoires to a Single Epitope of an Antigen," Bio/technology 12(9):899-903, Wiley-Blackwell, United States (1994).
Jobling, M.G. and Holmes, R.K., "Analysis of Structure and Function of the B Subunit of Cholera Toxin by the Use of Site-directed

(56) References Cited

OTHER PUBLICATIONS

Mutagenesis," Molecular Microbiology 5(7):1755-1767, Blackwell Scientific Publications, England (Jul. 1991).
Kabat, E.A., et al., "Sequences of Proteins of Immunological Interest," 5th Edition, U.S. Department of Public Health and Human Services, Public Health Service, National Institutes of Health, Bethesda (1991).
Kang, D., et al., "A Peptidoglycan Recognition Protein in Innate Immunity Conserved From Insects to Humans," Proceedings of the National Academy of Sciences of the United States of America 95(17):10078-10082, National Academy of Sciences, United States (Aug. 1998).
Karttunen, J. and Shastri, N., "Measurement of Ligand-induced Activation in Single Viable T Cells Using the lacZ Reporter Gene," Proceedings of the National Academy of Sciences of the United States of America 88(9):3972-3976, National Academy of Sciences, United States (1991).
Katsuura, M., et al., "CD48 Expression on Leukocytes in Infectious Diseases: Flow Cytometric Analysis of Surface Antigen," Acta Paediatrica Japonica 40(6):580-585, Blackwell Scientific, Australia (Dec. 1998).
Kaufman, R.J., et al., "Translational Efficiency of Polycistronic mRNAs and Their Utilization to Express Heterologous Genes in Mammalian Cells," The EMBO Journal 6(1):187-195, Wiley Blackwell, England (Jan. 1987).
Keane, J., et al., "Tuberculosis Associated With Infliximab, a Tumor Necrosis Factor Alpha-neutralizing Agent," The New England Journal of Medicine 345(15):1098-1104, Massachusetts Medical Society, United States (Oct. 2001).
Keen, J., et al., "Rapid Detection of Single Base Mismatches as Heteroduplexes on Hydrolink Gels," Trends in Genetics 7(1):5, Elsevier Trends Journals, England (Jan. 1991).
Kelker, M.S., et al., "Crystal Structure of Human Triggering Receptor Expressed on Myeloid Cells 1 (TREM-1) at 1.47 A," Journal of Molecular Biology 342(4):1237-1248, Elsevier, England (2004).
Kessel, M. And Gruss, P., "Murine Developmental Control Genes," Science 249(4967):374-379, American Association for the Advancement of Science, United States (Jul. 1990).
Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).
Kharitonenkov, A., et al., "FGF-21 as a Novel Metabolic Regulator," The Journal of Clinical Investigation 115(6):1627-1635, American Society for Clinical Investigation, United States (Jun. 2005).
Kharitonenkov, A., et al., "The Metabolic State of Diabetic Monkeys is Regulated by Fibroblast Growth Factor-21," Endocrinology 148(2):774-781, Oxford University Press, United States (Feb. 2007).
Kiem, H.P., et al., "Retrovirus-mediated Gene Transduction Into Canine Peripheral Blood Repopulating Cells," Blood 83(6):1467-1473, American Society of Hematology, United States (Mar. 1994).
Knappik, A. and Pluckthun, A., "An Improved Affinity Tag Based on the FLAG Peptide for the Detection and Purification of Recombinant Antibody Fragments," Biotechniques 17(4):754-761, Informa Healthcare USA, England (Oct. 1994).
Knudsen, L.B., "Glucagon-like Peptide-1: The Basis of a New Class of Treatment for Type 2 Diabetes," Journal of Medicinal Chemistry 47(17):4128-4134, American Chemical Society, United States (Aug. 2004).
Kohler, G., "Immunoglobulin Chain Loss in Hybridoma Lines," Proceedings of the National Academy of Sciences USA 77(4):2197-2199, National Academy of Sciences, United States (Apr. 1980).
Koller, B.H. and Smithies, O., "Inactivating the beta 2-Microglobulin Locus in Mouse Embryonic Stem Cells by Homologous Recombination," Proceedings of the National Academy of Sciences USA 86(22):8932-8935, National Academy of Sciences, United States (Nov. 1989).
Kozal, M.J., et al., "Extensive Polymorphisms Observed in HIV-1 Clade B Protease Gene Using High-density Oligonucleotide Arrays," Nature Medicine 2(7):753-759, Nature Publishing Company, United States (Jul. 1996).
Kozarsky, K.F. and Wilson, J.M., "Gene Therapy: Adenovirus Vectors," Current Opinion in Genetics & Development 3(3):499-503, Elsevier, England (Jun. 1993).
Kruse, C.A., et al., "Characterization of a Continuous Human Glioma Cell Line DBTRG-05MG: Growth Kinetics, Karyotype, Receptor Expression, and Tumor Suppressor Gene Analyses," In Vitro Cellular & Developmental Biology 28A(9-10):609-614, Tissue Culture Association, United States (Sep.-Oct. 1992).
Kuai, J., et al., "TREM-1 Expression is Increased in the Synovium of Rheumatoid Arthritis Patients and Induces the Expression of Pro-inflammatory Cytokines," Rheumatology 48(11):1352-1358, Mercury International, England (2009).
Kubagawa, H., et al., "Biochemical Nature and Cellular Distribution of the Paired Immunoglobulin-like Receptors, PIR-A and PIR-B," The Journal of Experimental Medicine 189(2):309-318, Rockefeller University Press, United States (Jan. 1999).
Kunkel, T.A., et al., "Rapid and Efficient Site-specific Mutagenesis Without Phenotypic Selection," Methods in Enzymology 154:367-382, Academic Press, United States (1987).
Kurjan, J. and Herskowitz, I., "Structure of a Yeast Pheromone Gene (MF Alpha): A Putative Alpha-factor Precursor Contains Four Tandem Copies of Mature Alpha-factor," Cell 30(3):933-943, Cell Press, United States (Oct. 1982).
Kwoh, D.Y., et al., "Transcription-Based Amplification System and Detection of Amplified Human Immunodeficiency Virus Type 1 with a Bead-Based Sandwich Hybridization Format," Proceedings of the National Academy of Sciences of the United States of America 86(4):1173-1177, National Academy of Sciences, United States (1989).
Lakso, M., et al., "Targeted Oncogene Activation by Site-specific Recombination in Transgenic Mice," Proceedings of the National Academy of Sciences 89(14):6232-6236, National Academy of Sciences, United States (Jul. 1992).
Lam, K.S., "Application of Combinatorial Library Methods in Cancer Research and Drug Discovery," Anticancer Drug Design 12(3):145-67, (1997).
Lam, K.S., et al., "A New Type of Synthetic Peptide Library for Identifying Ligand-Binding Activity," Nature 354:82-84, Nature Publishing Group, United States (1991).
Landegren, U., et al., "A Ligase-mediated Gene Detection Technique," Science 241(4869):1077-1080, American Association for the Advancement of Science, United States (Aug. 1988).
Lane, P., et al., "CD40 Ligand-independent B Cell Activation Revealed by CD40 Ligand-deficient T Cell Clones: Evidence for Distinct Activation Requirements for Antibody Formation and B Cell Proliferation," European Journal of Immunology 25(6):1788-1793, Wiley-VCH, Germany (Jun. 1995).
Lanier, L.L., et al., "Immunoreceptor DAP12 Bearing a Tyrosine-based Activation Motif is Involved in Activating NK Cells," Nature 391(6668):703-707, Nature Publishing Group, England (Feb. 1998).
Lanier, L.L., "NK Cell Receptors," Annual Review of Immunology 16:359-393, Annual Reviews Inc., United States (1998).
Lantz, M., et al., "Characterization in Vitro of a Human Tumor Necrosis Factor-binding Protein. A Soluble Form of a Tumor Necrosis Factor Receptor," The Journal of Clinical Investigation 86(5):1396-1402, American Society for Clinical Investigation, United States (Nov. 1990).
Larin, S.S., et al., "Immunotherapy with Autologous Tumor Cells Engineered to Secrete Tag7/PGRP, an Innate Immunity Recognition Molecule," Gene Medicine 6(7):798-808, John Wiley & Sons, England (Jul. 2004).
Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).
Letsinger, R.L., et al., "Cholesteryl-conjugated Oligonucleotides: Synthesis, Properties, and activity as Inhibitors of Replication of Human Immunodeficiency Virus in Cell Culture," Proceedings of

(56) References Cited

OTHER PUBLICATIONS the National Academy of Sciences USA 86(17):6553-6556, National Academy of Science, United States (Sep. 1989).
Li, E., et al., "Targeted Mutation of the DNA Methyltransferase Gene Results in Embryonic Lethality," Cell 69(6):915-926, Cell Press, United States (Jun. 1992).
Lizardi, M.P., et al., "Exponential Amplification of Recombinant-RNA Hybridization Probes," Nature Biotechnology 6:1197-1202 (1988).
Loeffler, J.P., et al., "Gene Transfer Into Primary and Established Mammalian Cell Lines With Lipopolyamine-coated DNA," Methods in Enzymology 217:599-618, Academic Press, United States (1993).
Lolis, E. and Bucala, R., "Therapeutic Approaches to Innate Immunity: Severe Sepsis and Septic Shock," Nature Reviews. Drug Discovery 2(8):635-645, Nature Pub. Group, England (Aug. 2003).
Lonberg, N. and Huszar, D., "Human Antibodies from Transgenic Mice," International Reviews of Immunology 13(1):65-93, Informa Healthcare, England (1995).
Lowy, I., et al., "Isolation of Transforming DNA: Cloning the Hamster aprt Gene," Cell 22(3):817-823, Cell Press, United States (Dec. 1980).
LS Bio/LifeSpan BioSciences, Inc., Pglyrp1/ pgrp antibody (ls-c579), accessed at http://www.lsbio.com/Antibodies/PGLYRP1-PGRP-Antibody-LS-C579/2801, Accessed on Jun. 12, 2014.
LS Bio/LifeSpan BioSciences, Inc., Pglyrp1 I pgrp antibody (ls-c38137), accessed at http://www.lsbio .com/Antibodies/PGLYRP1-PGRP-Antibody-LS-C38137/37645, Accessed on Aug. 1, 2014.
LS Bio/LifeSpan BioSciences, Inc., Pglyrpl/ pgrp antibody (ls-b4940), accessed at http://www.lsbio.com/Antibodies/PGLYRP1-PGRP-Antibody-LS-B4940/128350.
LS Bio/LifeSpan BioSciences, Inc., Pglyrpl/ pgrp antibody (ls-c578), accessed at http://www.lsbio.com/Antibodies/PGLYRP1-PGRP-Antibody-LS-0578/2800, Accessed on Jun. 12, 2014.
Lucklow, V.A., et al., "High Level Expression of Nonfused Foreign Genes With Autographa Californica Nuclear Polyhedrosis Virus Expression Vectors," Virology 170(1):31-39 (1989).
Maccallum, R.M., et al., "Antibody-antigen Interactions: Contact Analysis and Binding Site Topography," Journal of Molecular Biology 262(5):732-745, Academic Press, England (Oct. 1996).
Madura, K., et al., "N-Recognin/Ubc2 Interactions in Then-End Rule Pathway," Journal of Biological Chemistry 17:5973-5988 (1993).
Mag, M., et al., "Synthesis and Selective Cleavage of Oligodeoxyribonucleotides Containing Non-chiral Internucleotide Phosphoramidate Linkages," Nucleic Acids Research 17(15):5973-5988 ( Aug. 1989).
Maher, L.J., et al., "DNA Triple-helix Formation: an Approach to Artificial Gene Repressors?," BioEssays 14(12):807-815, Wiley, United States (Dec. 1992 ).
Malaviya, R., et al., "Mast Cell Modulation of Neutrophil Influx and Bacterial Clearance at Sites of Infection Through TNF-alpha," Nature 381(6577):77-80, Nature Publishing Group, England (May 1996).
Mastrangeli, A., et al., "Diversity of Airway Epithelial Cell Targets for in Vivo Recombinant Adenovirus-Mediated Gene Transfer," Journal of Clinical Investigation 91(1):225-234, American Society for Clinical Investigation, United States (Jan. 1993).
Maxam, A.M. and Gilbert, W., "A New Method for Sequencing DNA," Proceedings of the National Academy of Sciences USA 74(2):560-564, National Academy of Sciences, United States (Feb. 1977).
Mcnamara, M.J., et al., "Interleukin-1 Receptor Antibody (Il-1rab) Protection and Treatment Against Lethal Endotoxemia in Mice," Journal of Surgical Research 54(4):316-321, Academic Press, United States (Apr. 1993).
Medzhitov, R., et al., "Innate Immunity," The New England Journal of Medicine 343(5):338-344, Massachusetts Medical Society, United States (Aug. 2000).
Micanovic, R., et al., "Different Roles of N- and C- Termini in the Functional Activity of FGF21," Journal of Cellular Physiology 219(2):227-234, Wiley-Liss, United States (May 2009).
Michael, S.F., et al., "Mutagenesis by Incorporation of a Phosphorylated Oligo During PCR Amplification," BioTechniques 16(3):410-412, Informa Healthcare USA, England (Mar. 1994).
Miller, A.D., et al., "Use of Retroviral Vectors for Gene Transfer and Expression," Methods in Enzymology 217:581-599, Academic Press, United States (1993).
Mohamadzadeh, M., et al., "Activation of Triggering Receptor Expressed on Myeloid Cells-1 on Human Neutrophils by Marburg and Ebola Viruses," Journal of Virology 80(14):7235-7244, American Society for Microbiology, United States (Jul. 2006).
Molloy, E.J., "Triggering Receptor Expressed on Myeloid Cells (TREM) Family and the Application of its Antagonists," Recent Patents on Anti-infective Drug Discovery 4(1):51-56, Bentham Science Publishers, Netherlands (2009).
Morgan, R.A. and Anderson, W.F., "Human Gene Therapy," Annual Review of Biochemistry 62:191-217, Annual Reviews, United States (1993).
Mori, S.I., et al., "A Novel Amino Acid Substitution at the Receptor-binding Site on the Hemagglutinin of H3N2 Influenza a Viruses Isolated From 6 Cases With Acute Encephalopathy During the 1997-1998 Season in Tokyo," Archives of Virology 144(1):147-155, Springer-Verlag, Austria (1999).
Morrison, D.C., et al., "Endotoxins and Disease Mechanisms," Annual Review of Medicine 38:417-432, Annual Reviews, United States (1987).
Morrison, S.L., "Transfectomas Provide Novel Chimeric Antibodies," Science 229(4719):1202-1207, Association for the Advancement of Science, United States (Sep. 1985).
Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).
Mulligan, R.C., "The Basic Science of Gene Therapy," Science 260(5110):926-932, American Association for the Advancement of Science, United States (1993).
Mullinax, R.L., et al., "Expression of a Heterodimeric Fab Antibody Protein in One Cloning Step," BioTechniques 12(6):864-869, Informa Healthcare, England (1992).
Murakami, Y., et al., "Intervention of an Inflammation Amplifier, Triggering Receptor Expressed on Myeloid Cells 1, for Treatment of Autoimmune Arthritis," Arthritis and Rheumatism 60(6):1615-1623, Wiley-Blackwell, United States (Jun. 2009).
Myers, R.M., et al., "Detection of Single Base Substitutions by Ribonuclease Cleavage at Mismatches in RNA:DNA Duplexes," Science 230(4731):1242-1246, American Association for the Advancement of Science, United States (Dec. 1985 ).
Myers, R.M., et al., "Detection of Single Base Substitutions in Total Genomic DNA," Nature 313(6002):495-498, Nature Publishing Group, England (Feb. 1985).
Nakajima, H., et al., "2B4: an Nk Cell Activating Receptor With Unique Specificity and Signal Transduction Mechanism," Human Immunology 61(1):39-43, Elsevier/North-Holland, United States (Jan. 2000).
Nakajima, H., et al., "Cutting Edge: Human Myeloid Cells Express an Activating Ilt Receptor (ILT1) That Associates With Fc Receptor Gamma-chain," Journal of Immunology 162(1):5-8, American Association of Immunologists, United States (Jan. 1999).
Nakazawa, H., et al., "UV and Skin Cancer: Specific P53 Gene Mutation in Normal Skin as a Biologically Relevant Exposure Measurement," Proceedings of the National Academy of Sciences USA 91(1):360-364 (Jan. 1994).
Naramura, M., et al., "Mechanisms of Cellular Cytotoxicity Mediated by a Recombinant Antibody-IL2 Fusion Protein Against Human Melanoma Cells," Immunology Letters 39(1):91-99 (Dec. 1993).
Nathan, C. and Ding, A., "TREM-1: A New Regulator of Innate Immunity in Sepsis Syndrome," Nature Medicine 7(5):530-532, Nature Publishing Company, United States (May 2001).

(56) References Cited

OTHER PUBLICATIONS

Nauck, M.A. and Meier, J.J., "Glucagon-like Peptide 1 and its Derivatives in the Treatment of Diabetes," Regulatory Peptides 128(2):135-148, Elsevier/North Holland, Netherlands (Jun. 2005).
NCBL Sequence Viewer Accession No. AA099288 (May 11, 1997).
NCBL Sequence Viewer Accession No. AA101983 (May 11, 1997).
NCBL Sequence Viewer Accession No. AA494171 (Aug. 19, 1997).
NCBL Sequence Viewer Accession No. A1186456 (Oct. 28, 1998).
NCBL Sequence Viewer Accession No. A1337247 (Mar. 18, 1999).
NCBL Sequence Viewer Accession No. A1394092 (Mar. 30, 1999).
NCBL Sequence Viewer Accession No. A1621023 (Dec. 14, 1999).
NCBL Sequence Viewer Accession No. A1681036 (Dec. 16, 1999).
NCBL Sequence Viewer Accession No. A1962750 (Mar. 8, 2000).
NCBL Sequence Viewer Accession No. A1968134 (Aug. 25, 1999).
NCBL Sequence Viewer Accession No. AW135801 (Oct. 29, 1999).
NCBL Sequence Viewer Accession No. AW139363 (Oct. 30, 1999).
NCBL Sequence Viewer Accession No. AW139572 (Oct. 30, 1999).
Nederman, T., et al., "An in Vitro Bioassay for Quantitation of Human Interferons by Measurements of Antiproliferative Activity on a Continuous Human Lymphoma Cell Line," Biologicals 18(1):29-34, Academic Press, England (Jan. 1990).
Ngo, J.T., et al., "The Protein Folding Problem and Tertiary Structure Prediction, Chapter 14: Computational Complexity Protein Structure Prediction, and the Levinthal Paradox," 492-495 (Mar. 1995).
Nicoletti, I., et al., "A Rapid and Simple Method for Measuring Thymocyte Apoptosis by Propidium Iodide Staining and Flow Cytometry," Journal of Immunological Methods 139(2):271-279, Elsevier, Netherlands (Jun. 1991).
Office Action dated Mar. 21, 2018, in U.S. Appl. No. 15/483,309, inventors Stennicke, V., et al., filed Apr. 10, 2017, 12 pages.
O'Gorman, S., et al., "Recombinase-Mediated Gene Activation and Site-specific Integration in Mammalian Cells," Science 251(4999):1351-1355, American Association for the Advancement of Science, United States (Mar. 1991).
O'Hare, K., et al., "Transformation of Mouse Fibroblasts to Methotrexate Resistance by a Recombinant Plasmid Expressing a Prokaryotic Dihydrofolate Reductase," Proceedings of the National Academy of Sciences USA 78(3):1527-1531, National Academy of Sciences, United States (Mar. 1981).
Ohlsson, K., et al., "Interleukin-1 Receptor Antagonist Reduces Mortality from Endotoxin Shock," Nature 348(6301):550-552, Nature Publishing Group, England (Dec. 1990).
Oi, V.T. and Morrison, S.L., "Chimeric Antibodies," BioTechniques 4(3):214-221 (1986).
Oishi, K., et al., "Inhibition of Neutrophil Apoptosis by Antioxidants in Culture Medium," Scandinavian Journal of Immunology 45(1):21-27, Blackwell Scientific Publications, England (Jan. 1997 ).
Oliveira, J.S., et al., "Fungal Infections in Marrow Transplant Recipients Under Antifungal Prophylaxis With Fluconazol," Brazilian Journal of Medical and Biological Research 35(7):789-798, Brazilian Association of Scientific Dissemination, Brazil ( Jul. 2002 ).
Olopade, O.I., et al., "Molecular Analysis of Deletions of the Short Arm of Chromosome 9 in Human Gliomas," Cancer Research 52(9):2523-2529, American Association for Cancer Research, United States (May 1992).
Orita, M., et al., "Detection of Polymorphisms of Human DNA by Gel Electrophoresis as Single-strand Conformation Polymorphisms ," Proceedings of the National Academy of Sciences USA 86(8):2766-2770, National Academy of Sciences, United States (Apr. 1989 ).
Osanai, A., et al., "Mouse Peptidoglycan Recognition Protein PGLYRP-1 Plays a Role in the Host Innate Immune Response Against Listeria Monocytogenes Infection," Journal of Infection and Immunity 79(2):858-866, American Society for Microbiology, United States (Feb. 2011), XP055060881.
Owerbach, D., et al., "Genetics of the Large, External, Transformation-sensitive(LETS) Protein: Assignment of a Gene Coding for Expression of Lets to Human Chromosome 8," Proceedings of the National Academy of Sciences USA 75(11):5640-5644, National Academy of Sciences, United States (Nov. 1978 ).
Padlan, E.A., "A Possible Procedure for Reducing the Immunogenicity of Antibody Variable Domains While Preserving their Ligand-binding Properties," Molecular Immunology 28(4-5):489-498, Pergamon Press., England (Apr. 1991).
Pajunen, L., et al., "Assignment of the Gene Coding for Both the Beta-subunit of Prolyl 4-hydroxylase and the Enzyme Disulfide Isomerase to Human Chromosome Region 17p11-qter," Cytogenetics and Cell Genetics 47(1-2):37-41, Karger, Switzerland (1988).
Pant, S.,D., et al. "Bovine PGLYRP1 Polymorphisms and their Association with Resistance to Mycobacterium Avium ssp. Paratuberculosis," Animal Genetics 42(4):354-360, Wiley-Blackwell, England (Aug. 2011).
Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).
Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).
Peschon, J.J., et al., "TNF Receptor-Deficient Mice Reveal Divergent Roles for P55 and P75 in Several Models of Inftammation," Journal of Immunology 160(2):943-952, American Association of Immunologists, United States (Jan. 1998 ).
Petersen, K.H., et al., "A PNA-DNA Linker Synthesis of N-((4,4'-dimethoxytrityloxy)ethyl)- N- (Thymin-1-ylacetyl)glycine," Bioorganic & Medicinal Chemistry Letters 5:1119-1124 (1995).
Pfeffer, K., et al., "Mice Deficient for the 55 Kd Tumor Necrosis Factor Receptor are Resistant to Endotoxic Shock, Yet Succumb to L. Monocytogenes Infection," Cell 73(3):457-467, Cell Press,United States (May 1993 ).
Phua, J., et al., "Soluble Triggering Receptor Expressed on Myeloid Cells-1 in Acute Respiratory Infections," The European Respiratory Journal 28(4):695-702, European Respiratory Society, England (Oct. 2006).
Pinkert, C.A., et al., "An Albumin Enhancer Located 10 Kb Upstream Functions Along With its Promoter to Direct Efficient, Liver-specific Expression in Transgenic Mice," Genes & Development 1(3):268-276, Cold Spring Harbor Laboratory Press, United States (May 1987).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Poukoulidou, T., et al., "TREM-1 Expression on Neutrophils and Monocytes of Septic Patients: Relation to the Underlying Infection and the Implicated Pathogen," BMC Infectious Diseases 11(1): 8 pages, BioMed Central, England (Nov. 2011).
Prosser, J., "Detecting Single-base Mutations," Trends in Biotechnology 11(6):238-246, Elsevier Science Publishers, England (Jun. 1993).
Proudfoot, N.J., "Transcriptional Interference and Termination Between Duplicated Alpha-globin Gene Constructs Suggests a Novel Mechanism for Gene Regulation," Nature 322(6079):562-565, Nature Publishing Group, England (1986).
Queen, C. and Baltimore, D., "Immunoglobulin Gene Transcription is Activated by Downstream Sequence Elements," Cell 33(3):741-748, Cell Press, United States (Jul. 1983).
Radaev, S., et al., "Crystal Structure of the Human Myeloid Cell Activating Receptor TREM-1," Structure 11(12):1527-1535, Cell Press, United States (Dec. 2003).
Radany, E.H., et al., "Directed Establishment of Rat Brain Cell Lines With the Phenotypic Characteristics of Type 1 Astrocytes," Proceedings of the National Academy of Sciences of the United States of America 89(14):6467-6471, National Academy of Sciences, United States (Jul. 1992).
R&D Systems, "Human TREM-1 Antibody," accessed at http://www.rndsystems.com/Products/MAB1278 accessed on Nov. 27, 2012.

(56) References Cited

OTHER PUBLICATIONS

Redl, H., et al., "Animal Models as the Basis of Pharmacologic Intervention in Trauma and Sepsis Patients," World Journal of Surgery 20(4):487-492, Springer International, United States (May 1996).
Rheinwald, J.G., "Chapter 15 Serial Cultivation of Normal Human Epidermal Keratinocytes," Methods in Cell Biology 21A:229-254, Academic Press, United States (1980).
Riechmann, L., et al., "Reshaping Human Antibodies for Therapy," Nature 332(6162):323-327, Nature Publishing Group, United States (Mar. 1988).
Riedemann, N.C., et al., "Novel Strategies for the Treatment of Sepsis," Nature Medicine 9(5):517-524, Nature Publishing Company, United States (May 2003).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Rosenbaum, V. and Riesner, D., "Temperature-gradient Gel Electrophoresis. Thermodynamic Analysis of Nucleic Acids and Proteins in Purified Form and in Cellular Extracts," Biophysical Chemistry 26(2-3):235-246, Elsevier Science B.V, Netherlands (May 1987).
Rosenberg, H.F, and Gallin, J.I., "Inflammation," in Fundamental Immunology, 4th Ed. W. E. Paul, ed., Chapter 32, p. 1051-1058, Lippincott-Raven Publishers, 1999.
Rosenfeld, M.A., et al., "Adenovirus-mediated Transfer of a Recombinant alpha 1-antitrypsin Gene to the Lung Epithelium in Vivo," Science 252(5004):431-434, American Association for the Advancement of Science, United States (Apr. 1991).
Rosenfeld, M.A., et al., "In Vivo Transfer of the Human Cystic Fibrosis Transmembrane Conductance Regulator Gene to the Airway Epithelium," Cell 68(1):143-155, Cell Press, United States (Jan. 1992).
Rothe, J., et al., "Mice Lacking the Tumour Necrosis Factor Receptor 1 are Resistant to TNF-mediated Toxicity but Highly Susceptible to Infection by Listeria Monocytogenes," Nature 364(6440):798-802, Nature Publishing Group, England (Aug. 1993).
Royet, J., et al., "Peptidoglycan Recognition Proteins: Modulators of the Microbiome and Inflammation," Nature Reviews Immunology 11(12):837-851, Nature Pub. Group, England (Nov. 2011).
Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).
Saha, S., et al, "Peptidoglycan Recognition Proteins Protect Mice from Experimental Colitis by Promoting Normal Gut Flora and Preventing Induction of Interferon-Gamma," Cell Host & Microbe 8(2):147-162, Cell Press, United States (Aug. 2010).
Saha, S., et al, "PGLYRP-2 and Nod2 are both Required for Peptidoglycan-Induced Arthritis and Local Inflammation," Cell Host & Microbe 5(2):137-150, Cell Press, United States (Feb. 2009).
Saiki, R.K., et al., "Analysis of Enzymatically Amplified Beta-globin and HLA-DQ Alpha DNA With Allele-specific Oligonucleotide Probes," Nature 324(6093):163-166, Nature Publishing Group, England (Nov. 1986).
Saiki, R.K., et al., "Genetic Analysis of Amplified DNA With Immobilized Sequence-specific Oligonucleotide Probes," Proceedings of the National Academy of Sciences of the United States of America 86(16):6230-6234, National Academy of Sciences, United States (Aug. 1989).
Saleeba, J.A. and Cotton, R.G., "Chemical Cleavage of Mismatch to Detect Mutations," Methods in Enzymology 217:286-295, Academic Press, United States (1993).
Sallusto, F., et al., "Efficient Presentation of Soluble Antigen by Cultured Human Dendritic Cells is Maintained by Granulocyte/macrophage Colony-stimulating Factor Plus Interleukin 4 and Downregulated by Tumor Necrosis Factor Alpha," The Journal of Experimental Medicine 179(4):1109-1118, Rockefeller University Press, United States (1994).
Salmons, B. and Gunzburg, W.H., "Targeting of Retroviral Vectors for Gene Therapy," Human Gene Therapy 4(2):129-141, Liebert, United States (Apr. 1993).
Sambrook, et al., Molecular Cloning, A Laboratory Manual, 2nd Edition, Cold Spring Harbor Laboratory, Cold Spring Harbor, NY, Chapters 16 & 17 (1990).
Sanderson, S. and Shastri, N., "LacZ Inducible, Antigen/MHC-specific T Cell Hybrids," International Immunology 6(3):369-376, Oxford University Press, England (Mar. 1994).
Sanger, F., et al., "DNA Sequencing With Chain-terminating Inhibitors," Proceedings of the National Academy of Sciences of the United States of America 74(12):5463-5467, National Academy of Sciences, United States (Dec. 1977).
Santerre, R.F., et al., "Expression of Prokaryotic Genes for Hygromycin B and G418 Resistance as Dominant-selection Markers in Mouse L Cells," Gene 30(1-3):147-156, Elsevier/North-Holland, Netherlands (Oct. 1984).
Sawai, H., et al., "Direct Production of the Fab Fragment Derived From the Sperm Immobilizing Antibody Using Polymerase Chain Reaction and cDNA Expression Vectors," American Journal of reproductive immunology 34(1):26-34, Wiley-Blackwell, Denmark (1995).
Schenk, M., et al., "TREM-1-expressing Intestinal Macrophages Crucially Amplify Chronic Inflammation in Experimental Colitis and Inflammatory Bowel Diseases," The Journal of Clinical Investigation 117(10):3097-3106, American Society for Clinical Investigation, United States (2007).
Schultz, L.D., et al., "Expression and Secretion in Yeast of a 400-kDa Envelope Glycoprotein Derived From Epstein-Barr Virus," Gene 54(1):113-123, Elsevier/North-Holland, Netherlands (1987).
Scott, J.K. and Smith, G.P., "Searching for peptide ligands with an epitope library," Science 249(4967):386-390, American Association for the Advancement of Science, United States (1990).
Seed, B., "An LFA-3 cDNA Encodes a Phospholipid-linked Membrane Protein Homologous to its Receptor CD2," Nature 329(6142):840-842, Nature Publishing Group, England (Oct. 1987).
Sharif, O. and Knapp, S., "From Expression to Signaling: Roles of TREM-1 and TREM-2 in Innate Immunity and Bacterial Infection," Immunobiology 213(9-10):701-713, Elsevier, Netherlands (2008).
Shu, L., et al., "Secretion of a Single-gene-encoded Immunoglobulin From Myeloma Cells," Proceedings of the National Academy of Sciences of the USA 90(17):7995-7999, National Academy of Sciences, United States (1993).
Skerra, A. and Pluckthun, A., "Assembly of a Functional Immunoglobulin Fv Fragment in *Escherichia coli*," Science 240(4855):1038-1041, Association for the Advancement of Science, United States (May 1988).
Skolnick, "From Genes to Protein Stucture and Function: Novel Applications of Computational Approaches in the Genomic era," Trends in Biotechnology 18:34-39, Elsevier Science Publishers, London (Jan. 2000).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).
Smith, G.E., et al., "Production of Human Beta Interferon in Insect Cells Infected With a Baculovirus Expression Vector," Molecular and Cellular Biology 3(12):2156-2165, American Society for Microbiology, United States (Dec. 1983).
Smith, T.F. and Zhang, X., "The Challenges of Genome Sequence Annotation or "The Devil is in the Details"," Nature Biotechnology 15(12):1222-1223, Nature America Publishing, United States (Nov. 1997).
Springer, T.A., "Traffic Signals for Lymphocyte Recirculation and Leukocyte Emigration: The Multistep Paradigm," Cell 76(2):301-314, Cell Press, United States (Jan. 1994).
Standen, J. and Bihari, D., "Septic Shock," The New England Journal of Medicine 343:447-448 (Aug. 2010).
Steiner, H., "Peptidoglycan Recognition Proteins: On and Off Switches for Innate Immunity," Immunological Reviews 198:83-96, Blackwell, England (Apr. 2004).

(56) References Cited

OTHER PUBLICATIONS

Stemple, D.L. and Anderson, D.J., "Isolation of a Stem Cell for Neurons and Glia From the Mammalian Neural Crest," Cell 71(6):973-985, Cell Press, United States (Dec. 1992).
Stone, R., "Search for Sepsis Drugs Goes on Despite Past Failures," Science 264(5157):365-367, American Association for the Advancement of Science, United States (Apr. 1994).
Studnicka, G.M., et al., "Human-Engineered Monoclonal Antibodies Retain Full Specific Binding Activity by Preserving Non-CDR Complementarity-Modulating Residues," Protein Engineering 7(6):805-814, Oxford University Press, England (1994).
Sugimoto, T., et al., "Determination of Cell Surface Membrane Antigens Common to Both Human Neuroblastoma and Leukemia-lymphoma Cell Lines by a Panel of 38 Monoclonal Antibodies," Journal of the National Cancer Institute 73(1):51-57, Oxford University Press, United States (Jul. 1984).
Sullivan, G.W., et al., "Interaction of Tumor Necrosis Factor-alpha and Granulocyte Colony-stimulating Factor on Neutrophil Apoptosis, Receptor Expression, and Bactericidal Function," Proceedings of the Association of American Physicians 108(6):455-466, Blackwell Science, Inc., United States (Nov. 1996).
Szybalska, E.H. and Szybalski, W., "Genetics of Human Cess Line IV DNA-mediated Heritable Transformation of a Biochemical Trait," Proceedings of the National Academy of Sciences USA 48:2026-2034, National Academy of Sciences, United States (Dec. 1962).
Tessarz, A.S. and Cerwenka, A., "The TREM-1/DAP12 Pathway," Immunology Letters 116(2):111-116, Elsevier/North-Holland Biomedical Press, Netherlands (Mar. 2008).
The Merck Manuals Online Medical Library, Whitehouse Station, NJ: Merck Research Laboratories, Retrieved from the internet:< URL: http://www.merck.com/mmpe/print/sec06/ch068/ch068a. html> 2006-2007. (Retrieved on Nov. 19, 2007).
Thomas, K.R. and Capecchi, M.R., "Site-directed Mutagenesis by Gene Targeting in Mouse Embryo-derived Stem Cells," Cell 51(3):503-512, Cell Press, United States (Nov. 1987).
Thoma-Uszynski, S., et al., "Induction of Direct Antimicrobial Activity Through Mammalian Toll-like Receptors ," Science 291(5508):1544-1547, American Association for the Advancement of Science, United States (Feb. 2001).
Thorpe, Antibody Carriers of Cytotoxic Agents in Cencer Therapy: A Review, in Monoclonal Antibodies 84: Biological and Clinical Applications, Pinchera et al., eds., pp. 475-506 (1985).
Thorpe, P.E. and Ross, W.C., "The Preparation and Cytotoxic Properties of Antibody-toxin Conjugates," Immunological Reviews 62:119-158, Blackwell, England (1982).
Tolstoshev, P., "Gene Therapy, Concepts, Current Trials and Future Directions," Annual Review of Pharmacology and Toxicology 33:573-596, Annual Reviews, United States (1993).
Tomasello, E., et al., "Combined Natural Killer Cell and Dendritic Cell Functional Deficiency in KARAP/DAP12 Loss-of-function Mutant Mice," Immunity 13(3):355-364, Cell Press, United States (Sep. 2000).
Tomic, M., et al., "A Rapid and Simple Method for Introducing Specific Mutations Into Any Position of DNA Leaving All Other Positions Unaltered," Nucleic Acids Research 18(6):1656, Oxford University Press, England (Mar. 1990 ).
Tracey, K.J., et al., "Shock and Tissue Injury Induced by Recombinant Human Cachectin," Science 234(4775):470-474, American Association for the Advancement of Science, United States (1986).
Traunecker, A., et al., "Myeloma Based Expression System for Production of Large Mammalian Proteins," Trends in Biotechnology 9(4):109-113, Elsevier Science Publisher, England ( Apr. 1991 ).
Trowbridge, R.S., et al. , "Establishment and Characterization of Ferret Cells in Culture," In Vitro 18(11):952-960, Tissue Culture Assn, United States (Nov. 1982).
Tsuji, E., et al., "Simultaneous Onset of Acute Inflammatory Response, Sepsis-like Symptoms and Intestinal Mucosal Injury After Cancer Chemotherapy," International Journal of Cancer 107(2):303-308, Wiley-Liss, United States (Nov. 2003).
Turnbull, I.R., et al., "Cutting Edge: TREM-2 Attenuates Macrophage Activation," Journal of Immunology 177(6):3520-3524, American Association of Immunologists, United States (Sep. 2006).
Ulevitch, R.J., et al. , "Recognition of Gram-negative Bacteria and Endotoxin by the Innate Immune System," Current Opinion in Immunology 11(1):19-22, Elsevier, England (Feb. 1999 ).
Upender, M., et al. , "Megaprimer Method for in Vitro Mutagenesis Using Parallel Templates," Biotechniques 18(1):29-30, Informa Healthcare USA, Inc, England (Jan. 1995).
Urban, M.B., et al., "NF-kappa B Contacts DNA by a Heterodimer of the p50 and p65 Subunit," The EMBO Journal 10(7):1817-1825, Wiley Blackwell, England (Jul. 1991).
Van Der Krol, A.R., et al., "Modulation of Eukaryotic Gene Expression by Complementary RNA or DNA Sequences," Biotechniques 6(10):958-976, Informa Healthcare, United States (Nov. 1988).
Van Keuren, M., et al. , "Regional Assignment of Human Liver-Type 6-Phosphofructokinase to Chromosome 21q22.3 by Using Somatic Cell Hybrids and a Monoclonal Anti-L Antibody," Human Genetics 74(1):34-40, Springer Verlag, Germany (Sep. 1986 ).
Van Zee, K.J., et al., "Tumor Necrosis Factor Soluble Receptors Circulate During Experimental and Clinical Inflammation and Can Protect Against Excessive Tumor Necrosis Factor Alpha in Vitro and in Vivo," Proceedings of the National Academy of Sciences of the United States of America 89(11):4845-4849, National Academy of Sciences, United States (Jun. 1992).
Vincent, J.L., et al., "Clinical Trials of Immunomodulatory Therapies in Severe Sepsis and Septic Shock," Clinical Infectious Diseases 34(8):1084-1093, Oxford University Press, United States (Apr. 2002).
Wada, K.N., et al. , "Codon Usage Tabulated From the Genbank Genetic Sequence Data," Nucleic Acids Research 20:2111-2118, Oxford University Press, England (May 1992).
Wakayama, T., et al., "Mice Cloned From Embryonic Stem Cells," Proceedings of the National Academy of Sciences of the United States of America 96(26):14984-14989, National Academy of Sciences, United States (Dec. 1999).
Walsh, C.E., et al., "Gene Therapy for Human Hemoglobinopathies," Proceedings of the Society for Experimental Biology and Medicine 204(3):289-300, Blackwell Science, United States (Dec. 1993).
Wang, H., et al., "HMG-1 as a Late Mediator of Endotoxin Lethality in Mice," Science 285(5425):248-251, American Association for the Advancement of Science, United States (1999).
Wang, Q., et al., "A Packaging Cell Line for Propagation of Recombinant Adenovirus Vectors Containing Two Lethal Gene-region Deletions," Gene Therapy 2(10):775-783, Nature Publishing Group, England (Dec. 1995).
Warren, H.S., "Strategies for the Treatment of Sepsis," The New England Journal of Medicine 336(13):952-953, Massachusetts Medical Society, United States (Mar. 1997).
Wasmuth, H.E., et al., "Patients With Acute on Chronic Liver Failure Display "Sepsis-like" Immune Paralysis," Journal of Hepatology 42(2):195-201, Elsevier, Netherlands (Feb. 2005).
Weintraub, H., et al., "Anti-sense RNA as a Molecular Tool for Genetic Analysis,"Trends in Genetics 1:22-25 (1985).
Wells, J.A., "Additivity of Mutational Effects in Proteins," Biochemistry 29(37):8509-8517, American Chemical Society, United States (Sep. 1990).
Wheeler, A.P. and Bernard, G.R., "Treating Patients With Severe Sepsis," The New England Journal of Medicine 340(3):207-214, Massachusetts Medical Society, United States (Jan. 1999).
Wigler, M., et al., "Transfer of Purified Herpes Virus Thymidine Kinase Gene to Cultured Mouse Cells," Cell 11(1):223-232, Cell Press, United States (May 1977).
Wigler, M., et al., "Transformation of Mammalian Cells with an Amplifiable Dominant-Acting Gene," Proceedings of the National Academy of Sciences USA 77(6):3567-3570, National Academy of Sciences, United States (Jun. 1980).
Wilmut, I., et al., "Viable Offspring Derived From Fetal and Adult Mammalian Cells," Nature 385(6619):810-813, Nature Publishing Group, England (Feb. 1997).

(56) References Cited

OTHER PUBLICATIONS

Wilson, I.A., et al., "The Structure of an Antigenic Determinant in a Protein," Cell 37(3):767-778, Cell Press, United States (Jul. 1984).
Winoto, A. and Baltimore, D., "A Novel, Inducible and T Cell-specific Enhancer Located at the 3' End of the T Cell Receptor Alpha Locus," The EMBO Journal 8(3):729-733, Wiley Blackwell, England (Mar. 1989).
Wu, G.Y. and Wu, C.H., "Delivery Systems for Gene Therapy," Biotherapy 3(1):87-95, Kluwer Academic Publishers, Netherlands (1991).
Wu, G.Y. and Wu, C.H., "Receptor-mediated in Vitro Gene Transformation by a Soluble DNA Carrier System," The Journal of Biological Chemistry 262(10):4429-4432, American Society for Biochemistry and Molecular Biology, United States (1987).
Wu, H., et al., "Humanization of a Murine Monoclonal Antibody by Simultaneous Optimization of Framework and CDR Residues," Journal of Molecular Biology 294(1):151-162, Elsevier, England (Nov. 1999).
Xu, J., et al., "Fibroblast Growth Factor 21 Reverses Hepatic Steatosis, Increases Energy Expenditure, and Improves Insulin Sensitivity in Diet-induced Obese Mice," Diabetes 58(1):250-259, American Diabetes Association, United States (2009).
Yamashita, Y., et al., "Inhibitory and Stimulatory Functions of Paired Ig-like Receptor (PIR) Family in RBL-2H3 Cells.," Journal of Immunology 161(8):4042-4047, American Association of Immunologists, United States (Oct. 1998).
Yie, J., et al., "FGF21 N- and C-termini Play Different Roles in Receptor Interaction and Activation," FEBS Letters 583(1):19-24, John Wiley & Sons Ltd, England (Jan. 2009).
Zervos, A.S., et al., Mxi1, a protein that specifically interacts with Max to bind Myc-Max recognition site,Cell 72(2):223-232, Elsevier Science, United States (1993).
Zhang, J., et al., "Transient Expression and Purification of Chimeric Heavy Chain Antibodies," Protein Expression and Purification 65(1):77-82, Academic Press, United States (May 2009).
Zijlstra, M., et al., "Germ-line Transmission of a Disrupted beta 2-microglobulin Gene Produced by Homologous Recombination in Embryonic Stem Cells," Nature 342(6248):435-438, Nature Publishing Group, England (Nov. 1989).
Zon, G., et al., "Oligonucleotide Analogues as Potential Chemotherapeutic Agents," Pharmaceutical Research 5(9):539-549, Kluwer Academic/Plenum Publishers, United States (Sep. 1988).
Zuckermann, R.N., et al., "Discovery of nanomolar ligands for 7-transmembrane G-protein-coupled receptors from a diverse N-(substituted)glycine peptoid librar," Journal of Medicinal Chemistry 37(17):2678-2685, ACS Publications, United Kingdom (1994).
Zwaveling, J.H., et al., "High Plasma Tumor Necrosis Factor (TNF)-alpha Concentrations and a Sepsis-like Syndrome in Patients Undergoing Hyperthermic Isolated Limb Perfusion With Recombinant TNF-alpha, Interferon-gamma, and Melphalan," Critical Care Medicine 24(5):765-770, Lippincott Williams & Wilkins, United States (May 1996).

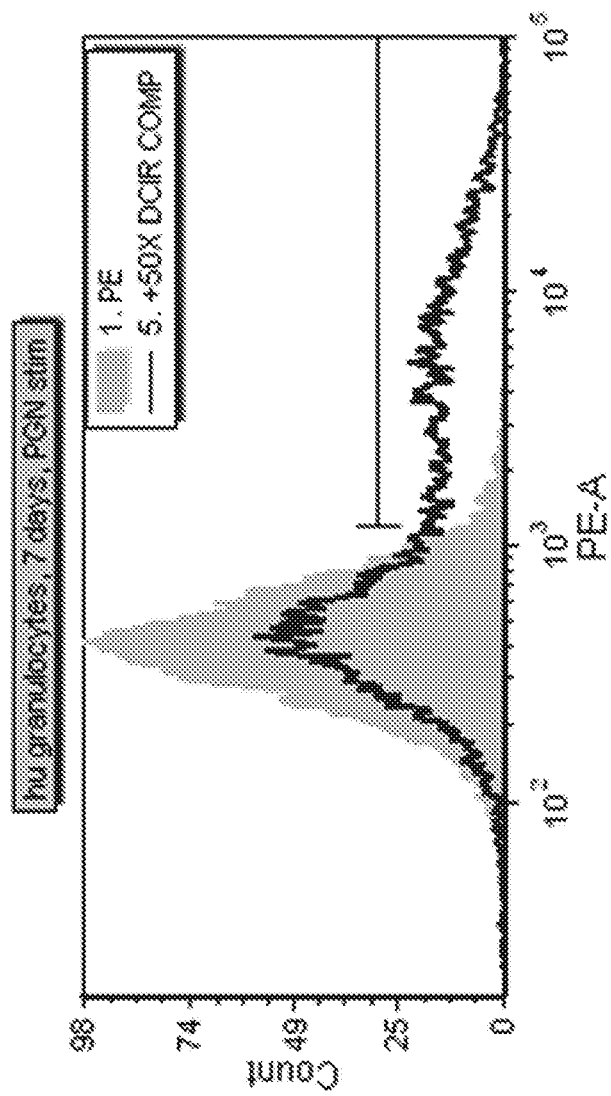

CD83/Neutrophil    Trem1/Neutrophil

| Identified Proteins | Gene Symbols | Accession Number |
|---|---|---|
| Isoform 1 of Triggering receptor expressed on myeloid cells 1 | Trem1 | IPI00427321 |
| Peptidoglycan recognition protein 1 | PGLYRP1 | IPI00021085 |
| Isoform 3 of Tyrosine-protein phosphatase non-receptor type 6 | PTPN6 | IPI00183046 |

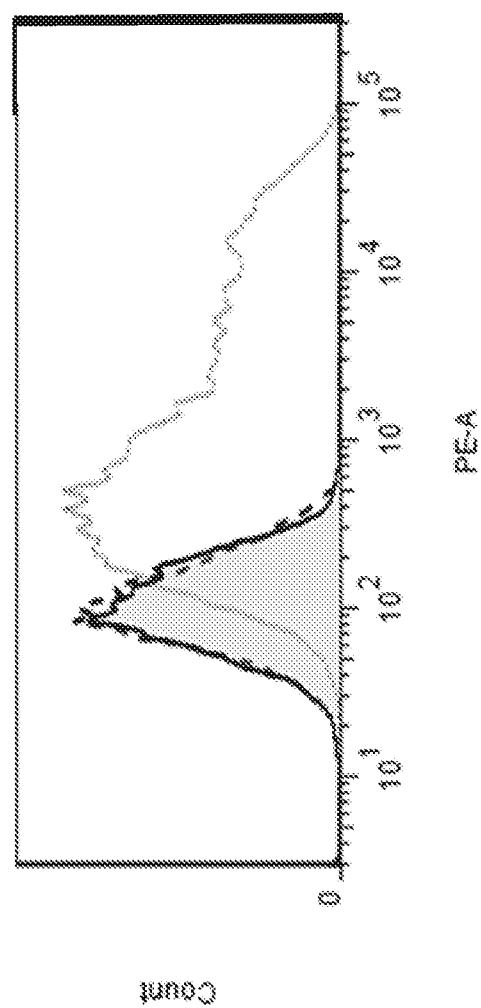

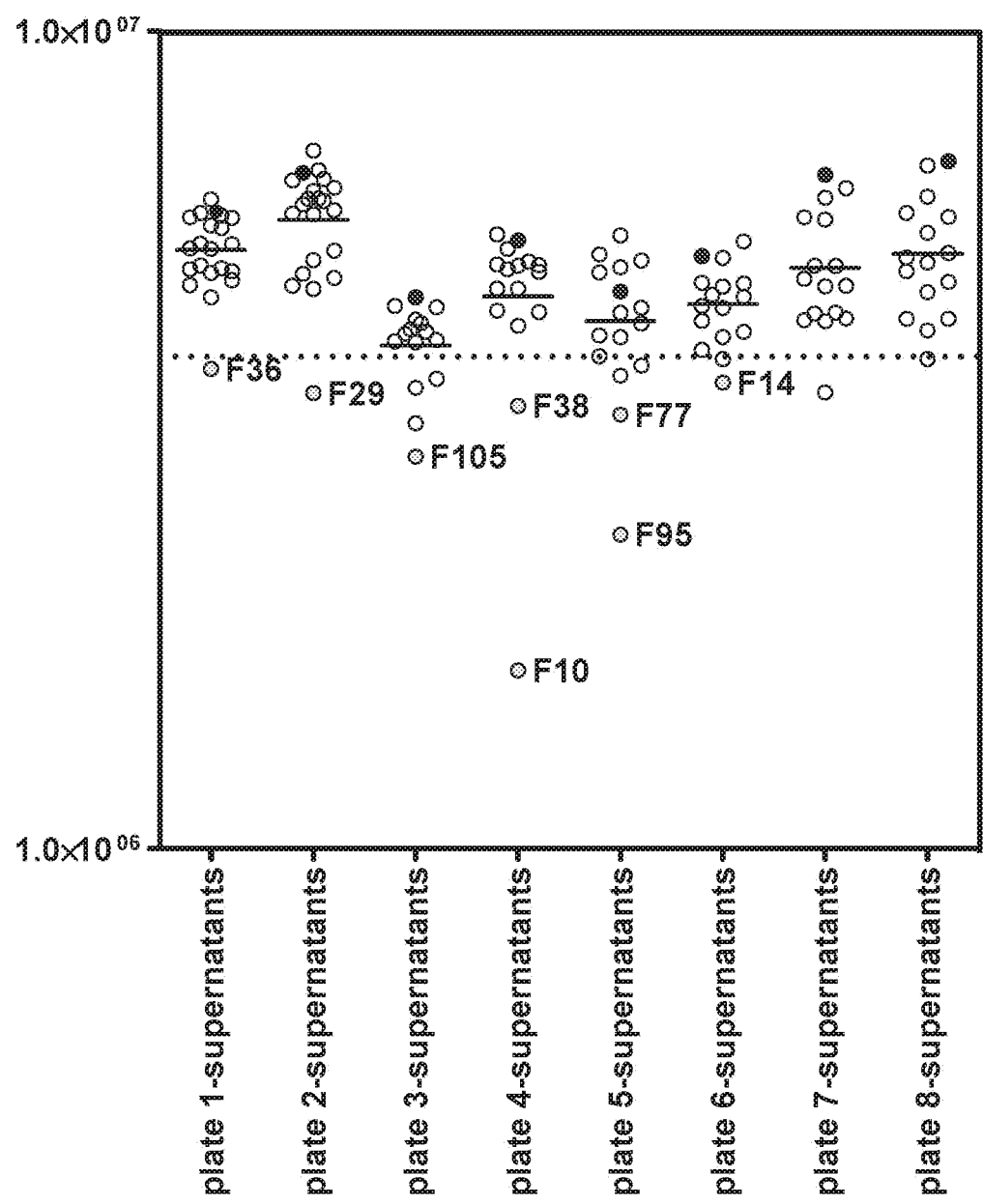

SEQUENCE LISTING

```
<160> NUMBER OF SEQ ID NOS: 53

<210> SEQ ID NO 1
<211> LENGTH: 175
<212> TYPE: PRT
<213> ORGANISM: Homo sapiens

<400> SEQUENCE: 1

Gln Glu Thr Glu Asp Pro Ala Cys Cys Ser Pro Ile Val Pro Arg Asn
1               5                   10                  15

Glu Trp Lys Ala Leu Ala Ser Glu Cys Ala Gln His Leu Ser Leu Pro
            20                  25                  30

Leu Arg Tyr Val Val Val Ser His Thr Ala Gly Ser Ser Cys Asn Thr
        35                  40                  45

Pro Ala Ser Cys Gln Gln Gln Ala Arg Asn Val Gln His Tyr His Met
    50                  55                  60

Lys Thr Leu Gly Trp Cys Asp Val Gly Tyr Asn Phe Leu Ile Gly Glu
65                  70                  75                  80

Asp Gly Leu Val Tyr Glu Gly Arg Gly Trp Asn Phe Thr Gly Ala His
                85                  90                  95

Ser Gly His Leu Trp Asn Pro Met Ser Ile Gly Ile Ser Phe Met Gly
            100                 105                 110

Asn Tyr Met Asp Arg Val Pro Thr Pro Gln Ala Ile Arg Ala Ala Gln
        115                 120                 125

Gly Leu Leu Ala Cys Gly Val Ala Gln Gly Ala Leu Arg Ser Asn Tyr
    130                 135                 140

Val Leu Lys Gly His Arg Asp Val Gln Arg Thr Leu Ser Pro Gly Asn
145                 150                 155                 160

Gln Leu Tyr His Leu Ile Gln Asn Trp Pro His Tyr Arg Ser Pro
                165                 170                 175

<210> SEQ ID NO 2
<211> LENGTH: 617
<212> TYPE: PRT
<213> ORGANISM: Artificial
<220> FEATURE:
<223> OTHER INFORMATION: TREM ECD+Fc6mut

<400> SEQUENCE: 2
```

-continued

```
Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
                20                  25                  30

Ala Ser Ser Gln Lys Ala Trp Gln Ile Ile Arg Asp Gly Glu Met Pro
        35                  40                  45

Lys Thr Leu Ala Cys Thr Glu Arg Pro Ser Lys Asn Ser His Pro Val
    50                  55                  60

Gln Val Gly Arg Ile Ile Leu Glu Asp Tyr His Asp Gly Leu Leu
65                  70                  75                  80

Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
                100                 105                 110

Ile Arg Leu Val Val Thr Lys Gly Phe Ser Gly Thr Pro Gly Ser Asn
            115                 120                 125

Glu Asn Ser Thr Gln Asn Val Tyr Lys Ile Pro Pro Thr Thr Thr Lys
130                 135                 140

Ala Leu Cys Pro Leu Tyr Thr Ser Pro Arg Thr Val Thr Gln Ala Pro
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg Gly Thr Gly Gly Gly Ser Gly
                180                 185                 190

Gly Gly Gly Ser Gly Gly Gly Ser Glu Leu Arg Ala Ala Thr Lys
            195                 200                 205

Leu Thr Glu Glu Lys Tyr Glu Leu Lys Glu Gly Gln Thr Leu Asp Val
210                 215                 220

Lys Cys Asp Tyr Thr Leu Glu Lys Phe Ala Ser Ser Gln Lys Ala Trp
225                 230                 235                 240

Gln Ile Ile Arg Asp Gly Glu Met Pro Lys Thr Leu Ala Cys Thr Glu
                245                 250                 255

Arg Pro Ser Lys Asn Ser His Pro Val Gln Val Gly Arg Ile Ile Leu
                260                 265                 270

Glu Asp Tyr His Asp His Gly Leu Leu Arg Val Arg Met Val Asn Leu
            275                 280                 285

Gln Val Glu Asp Ser Gly Leu Tyr Gln Cys Val Ile Tyr Gln Pro Pro
            290                 295                 300

Lys Glu Pro His Met Leu Phe Asp Arg Ile Arg Leu Val Val Thr Lys
305                 310                 315                 320

Gly Phe Ser Gly Thr Pro Gly Ser Asn Glu Asn Ser Thr Gln Asn Val
                325                 330                 335

Tyr Lys Ile Pro Pro Thr Thr Thr Lys Ala Leu Cys Pro Leu Tyr Thr
                340                 345                 350

Ser Pro Arg Thr Val Thr Gln Ala Pro Pro Lys Ser Thr Ala Asp Val
            355                 360                 365

Ser Thr Pro Asp Ser Glu Ile Asn Leu Thr Asn Val Thr Asp Ile Ile
        370                 375                 380

Arg Gly Pro Lys Ser Ser Asp Lys Thr His Thr Cys Pro Pro Cys Pro
385                 390                 395                 400

Ala Pro Glu Ala Glu Gly Ala Pro Ser Val Phe Leu Phe Pro Pro Lys
            405                 410                 415
```

```
Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ser Ser Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615

<210> SEQ ID NO 3
<211> LENGTH: 228
<212> TYPE: PRT
<213> ORGANISM: Artificial
<220> FEATURE:
<223> OTHER INFORMATION: Fc5mut

<400> SEQUENCE: 3

Ala Asp Lys Thr His Thr Cys Pro Pro Cys Pro Ala Pro Glu Ala Glu
1               5                   10                  15

Gly Ala Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 4
<211> LENGTH: 358
<212> TYPE: PRT
<213> ORGANISM: Artificial
<220> FEATURE:
<223> OTHER INFORMATION: hDCIR ECD COMP for pentamer

<400> SEQUENCE: 4

His His His His His Glu Asp Leu Tyr Phe Gln Ser Met Asp Glu
 1               5                  10                  15

Lys Thr Thr Gly Trp Arg Gly His Val Val Glu Gly Leu Ala Gly
            20                  25                  30

Glu Leu Glu Gln Leu Arg Ala Arg Leu Glu His His Pro Gln Gly Gln
        35                  40                  45

Arg Glu Pro Gly Ser Gly Met Asp Glu Lys Thr Thr Gly Trp Arg Gly
    50                  55                  60

Gly His Val Val Glu Gly Leu Ala Gly Glu Leu Glu Gln Leu Arg Ala
65                  70                  75                  80

Arg Leu Glu His His Pro Gln Gly Gln Arg Glu Pro Gly Gly Gly Ser
                85                  90                  95

Gly Gly Gly Ser Gly Gly Gly Ser Gly Asp Leu Ala Pro Gln Met Leu
            100                 105                 110

Arg Glu Leu Gln Glu Thr Asn Ala Ala Leu Gln Asp Val Arg Glu Leu
        115                 120                 125

Leu Arg Gln Gln Val Lys Glu Ile Thr Phe Leu Lys Asn Thr Val Met
    130                 135                 140

Glu Cys Asp Ala Cys Gly Met Gln Pro Ala Arg Thr Pro Gly Leu Ser
145                 150                 155                 160

Val Gly Gly Gly Ser Gly Gly Gly Ser Gly Gly Ser Leu Glu Val
            165                 170                 175

Leu Phe Gln Gly Pro Arg Ser Ile Ala Phe Val Ile Phe Gln Lys
        180                 185                 190

Tyr Ser Gln Leu Leu Glu Lys Lys Thr Thr Lys Glu Leu Val His Thr
    195                 200                 205

Thr Leu Glu Cys Val Lys Lys Asn Met Pro Val Glu Glu Thr Ala Trp
210                 215                 220

Ser Cys Cys Pro Lys Asn Trp Lys Ser Phe Ser Ser Asn Cys Tyr Phe
225                 230                 235                 240

Ile Ser Thr Glu Ser Ala Ser Trp Gln Asp Ser Glu Lys Asp Cys Ala
            245                 250                 255

Arg Met Glu Ala His Leu Leu Val Ile Asn Thr Gln Glu Glu Gln Asp
        260                 265                 270

Phe Ile Phe Gln Asn Leu Gln Glu Glu Ser Ala Tyr Phe Val Gly Leu
    275                 280                 285
```

```
Ser Asp Pro Glu Gly Gln Arg His Trp Gln Trp Val Asp Gln Thr Pro
        290                 295                 300

Tyr Asn Glu Ser Ser Thr Phe Trp His Pro Arg Glu Pro Ser Asp Pro
305                 310                 315                 320

Asn Glu Arg Cys Val Val Leu Asn Phe Arg Lys Ser Pro Lys Arg Trp
                325                 330                 335

Gly Trp Asn Asp Val Asn Cys Leu Gly Pro Gln Arg Ser Val Cys Glu
                340                 345                 350

Met Met Lys Ile His Leu
        355
```

<210> SEQ ID NO 5
<211> LENGTH: 367
<212> TYPE: PRT
<213> ORGANISM: Artificial
<220> FEATURE:
<223> OTHER INFORMATION: hTREM-1 ECD COMP for pentamer

<400> SEQUENCE: 5

```
Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
            20                  25                  30

Ala Ser Ser Gln Lys Ala Trp Gln Ile Ile Arg Asp Gly Glu Met Pro
        35                  40                  45

Lys Thr Leu Ala Cys Thr Glu Arg Pro Ser Lys Asn Ser His Pro Val
    50                  55                  60

Gln Val Gly Arg Ile Ile Leu Glu Asp Tyr His Asp His Gly Leu Leu
65                  70                  75                  80

Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
            100                 105                 110

Ile Arg Leu Val Val Thr Lys Gly Phe Ser Gly Thr Pro Gly Ser Asn
        115                 120                 125

Glu Asn Ser Thr Gln Asn Val Tyr Lys Ile Pro Pro Thr Thr Thr Lys
    130                 135                 140

Ala Leu Cys Pro Leu Tyr Thr Ser Pro Arg Thr Val Thr Gln Ala Pro
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg Gly Thr Leu Glu Val Leu Phe Gln
            180                 185                 190

Gly Pro Gly Gly Ser Gly Gly Gly Ser Gly Gly Gly Ser Gly Asp
        195                 200                 205

Leu Ala Pro Gln Met Leu Arg Glu Leu Gln Glu Thr Asn Ala Ala Leu
    210                 215                 220

Gln Asp Val Arg Glu Leu Leu Arg Gln Gln Val Lys Glu Ile Thr Phe
225                 230                 235                 240

Leu Lys Asn Thr Val Met Glu Cys Asp Ala Cys Gly Met Gln Pro Ala
                245                 250                 255

Arg Thr Pro Gly Leu Ser Val Gly Gly Gly Ser Gly Gly Gly Ser Gly
            260                 265                 270

Gly Gly Ser Met Asp Glu Lys Thr Thr Gly Trp Arg Gly Gly His Val
        275                 280                 285
```

```
Val Glu Gly Leu Ala Gly Glu Leu Glu Gln Leu Arg Ala Arg Leu Glu
    290                 295                 300
His His Pro Gln Gly Gln Arg Glu Pro Gly Ser Gly Met Asp Glu Lys
305                 310                 315                 320
Thr Thr Gly Trp Arg Gly Gly His Val Val Glu Gly Leu Ala Gly Glu
                325                 330                 335
Leu Glu Gln Leu Arg Ala Arg Leu Glu His His Pro Gln Gly Gln Arg
            340                 345                 350
Glu Pro Glu Asp Leu Tyr Phe Gln Ser His His His His His His
        355                 360                 365
```

<210> SEQ ID NO 6
<211> LENGTH: 505
<212> TYPE: PRT
<213> ORGANISM: Artificial
<220> FEATURE:
<223> OTHER INFORMATION: hCD83 ECD Fc

<400> SEQUENCE: 6

```
Thr Pro Glu Val Lys Val Ala Cys Ser Glu Asp Val Asp Leu Pro Cys
1               5                   10                  15
Thr Ala Pro Trp Asp Pro Gln Val Pro Tyr Thr Val Ser Trp Val Lys
            20                  25                  30
Leu Leu Glu Gly Gly Glu Glu Arg Met Glu Thr Pro Gln Glu Asp His
        35                  40                  45
Leu Arg Gly Gln His Tyr His Gln Lys Gly Gln Asn Gly Ser Phe Asp
    50                  55                  60
Ala Pro Asn Glu Arg Pro Tyr Ser Leu Lys Ile Arg Asn Thr Thr Ser
65                  70                  75                  80
Cys Asn Ser Gly Thr Tyr Arg Cys Thr Leu Gln Asp Pro Asp Gly Gln
                85                  90                  95
Arg Asn Leu Ser Gly Lys Val Ile Leu Arg Val Thr Gly Cys Pro Ala
            100                 105                 110
Gln Arg Lys Glu Glu Thr Phe Lys Lys Tyr Arg Ala Glu Gly Thr Gly
        115                 120                 125
Gly Gly Gly Ser Gly Gly Gly Gly Ser Gly Gly Gly Ser Thr Pro
    130                 135                 140
Glu Val Lys Val Ala Cys Ser Glu Asp Val Asp Leu Pro Cys Thr Ala
145                 150                 155                 160
Pro Trp Asp Pro Gln Val Pro Tyr Thr Val Ser Trp Val Lys Leu Leu
                165                 170                 175
Glu Gly Gly Glu Glu Arg Met Glu Thr Pro Gln Glu Asp His Leu Arg
            180                 185                 190
Gly Gln His Tyr His Gln Lys Gly Gln Asn Gly Ser Phe Asp Ala Pro
        195                 200                 205
Asn Glu Arg Pro Tyr Ser Leu Lys Ile Arg Asn Thr Thr Ser Cys Asn
    210                 215                 220
Ser Gly Thr Tyr Arg Cys Thr Leu Gln Asp Pro Asp Gly Gln Arg Asn
225                 230                 235                 240
Leu Ser Gly Lys Val Ile Leu Arg Val Thr Gly Cys Pro Ala Gln Arg
                245                 250                 255
Lys Glu Glu Thr Phe Lys Lys Tyr Arg Ala Glu Gly Ala Leu Ala Gly
            260                 265                 270
Thr Glu Pro Lys Ser Ser Asp Lys Thr His Thr Cys Pro Pro Cys Pro
        275                 280                 285
```

```
Ala Pro Glu Ala Glu Gly Ala Pro Ser Val Phe Leu Phe Pro Pro Lys
    290                 295                 300
Pro Lys Asp Thr Leu Met Ile Ser Arg Thr Pro Glu Val Thr Cys Val
305                 310                 315                 320
Val Val Asp Val Ser His Glu Asp Pro Glu Val Lys Phe Asn Trp Tyr
                325                 330                 335
Val Asp Gly Val Glu Val His Asn Ala Lys Thr Lys Pro Arg Glu Glu
            340                 345                 350
Gln Tyr Asn Ser Thr Tyr Arg Val Val Ser Val Leu Thr Val Leu His
        355                 360                 365
Gln Asp Trp Leu Asn Gly Lys Glu Tyr Lys Cys Lys Val Ser Asn Lys
    370                 375                 380
Ala Leu Pro Ser Ser Ile Glu Lys Thr Ile Ser Lys Ala Lys Gly Gln
385                 390                 395                 400
Pro Arg Glu Pro Gln Val Tyr Thr Leu Pro Pro Ser Arg Glu Glu Met
                405                 410                 415
Thr Lys Asn Gln Val Ser Leu Thr Cys Leu Val Lys Gly Phe Tyr Pro
            420                 425                 430
Ser Asp Ile Ala Val Glu Trp Glu Ser Asn Gly Gln Pro Glu Asn Asn
        435                 440                 445
Tyr Lys Thr Thr Pro Pro Val Leu Asp Ser Asp Gly Ser Phe Phe Leu
    450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                485                 490                 495
Lys Ser Leu Ser Leu Ser Pro Gly Lys
            500                 505

<210> SEQ ID NO 7
<211> LENGTH: 684
<212> TYPE: DNA
<213> ORGANISM: Artificial
<220> FEATURE:
<223> OTHER INFORMATION: hPGYRP1-GPI

<400> SEQUENCE: 7
gaattcgcca ccatgtcccg ccgctctatg ctgcttgcct gggctctccc cagcctcctt      60
cgactcggag cggctcagga gacagaagac ccggcctgct gcagccccat agtgccccgg     120
aacgagtgga aggccctggc atcagagtgc gcccagcacc tgagcctgcc cttacgctat     180
gtggtggtat cgcacacggc gggcagcagc tgcaacaccc ccgcctcgtg ccagcagcag     240
gcccggaatg tgcagcacta ccacatgaag acactgggct ggtgcgacgt gggctacaac     300
ttcctgattg agaagacggg gctcgtatac gagggccgtg gctggaactt cacgggtgcc     360
cactcaggtc acttatggaa ccccatgtcc attggcatca gcttcatggg caactacatg     420
gatcgggtgc ccacacccca ggccatccgg gcagcccagg gtctactggc ctgcggtgtg     480
gctcagggag ccctgaggtc caactatgtg ctcaaaggac accgggatgt gcagcgtaca     540
ctctctccag caaccagct ctaccactc atccagaatt ggccacacta ccgctccccc     600
tcctcatcga caactacgac acaaactacg accctacttc tcctgctact ctgctccta     660
cttctgctcc tactttgact cgag                                            684

<210> SEQ ID NO 8
<211> LENGTH: 180
```

```
<212> TYPE: PRT
<213> ORGANISM: Homo sapiens

<400> SEQUENCE: 8

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
                20                  25                  30

Lys Ala Trp Gln Ile Ile Arg Asp Gly Glu Met Pro Lys Thr Leu Ala
            35                  40                  45

Cys Thr Glu Arg Pro Ser Lys Asn Ser His Pro Val Gln Val Gly Arg
        50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
                100                 105                 110

Val Thr Lys Gly Phe Ser Gly Thr Pro Gly Ser Asn Glu Asn Ser Thr
            115                 120                 125

Gln Asn Val Tyr Lys Ile Pro Pro Thr Thr Lys Ala Leu Cys Pro
        130                 135                 140

Leu Tyr Thr Ser Pro Arg Thr Val Thr Gln Ala Pro Pro Lys Ser Thr
145                 150                 155                 160

Ala Asp Val Ser Thr Pro Asp Ser Glu Ile Asn Leu Thr Asn Val Thr
                165                 170                 175

Asp Ile Ile Arg
            180

<210> SEQ ID NO 9
<211> LENGTH: 1221
<212> TYPE: DNA
<213> ORGANISM: Artificial
<220> FEATURE:
<223> OTHER INFORMATION: hTREM ECD x2

<400> SEQUENCE: 9
gaattcgcaa ctatgcctct gctgctgctg ctgcctctgc tgtgggctgg cgcactggct      60
gaactgaggg ccgctaccaa actgaccgaa gaaaagtacg agctgaaaga agggcagacc     120
ctggacgtga gtgcgatta tacactggaa aagttcgcaa gctcccagaa agcctggcag     180
atcattagag acggagagat gcccaagact ctggcttgta ccgaacgccc ttcaaaaaac     240
agccacccag tgcaggtcgg ccgaatcatt ctggaggact accacgatca tgggctgctg     300
cgggtgagaa tggtcaatct gcaggtggag gactccggcc tgtaccagtg cgtcatctat     360
cagcccccta aggaaccaca tatgctgttc gataggattc gcctggtggt cactaaaggc     420
ttttctggga cccccggaag taacgagaac agcacccaga acgtgtacaa gatcccaccc     480
accacaacta aggccctgtg ccccctgtat acatctcctc gaaccgtgac acaggcccct     540
ccaaagagta ccgctgacgt gagcacaccc gattccgaga ttaacctgac aaatgtgact     600
gacatcatta ggggtaccgg aggaggagga tccggaggag gaggaagcgg aggcgggga     660 tccgaactgc gcgccgctac caagctgaca gaggaaaaat atgagctgaa agaaggccag     720
actctggacg tgaaatgcga ttataccctg gagaagtttg cttctagtca gaaagcatgg     780
cagatcattc gcgatgggga gatgcctaag acactggcct gtactgaacg gcctccaaa     840
```

| | |
|---|---|
| aactctcacc ctgtgcaggt cggaagaatc attctggaag actatcacga tcatggcctg | 900 |
| ctgcgagtgc ggatggtgaa tctgcaggtc gaggacagtg gactgtatca atgcgtcatc | 960 |
| tatcaacccc ctaaggaacc tcatatgctg ttcgatagaa ttaggctggt ggtcacaaaa | 1020 |
| ggctttagcg ggactccagg atctaacgag aatagtactc agaacgtgta caaaattcct | 1080 |
| cctactacca ccaaggccct gtgcccactg tatacaagcc cacgaactgt gacccaggca | 1140 |
| cctccaaaga gcactgcaga tgtgagcact ccagatagcg aaatcaacct gaccaatgtg | 1200 |
| acagatatta ttagggggcc c | 1221 |

<210> SEQ ID NO 10
<211> LENGTH: 1170
<212> TYPE: DNA
<213> ORGANISM: Artificial
<220> FEATURE:
<223> OTHER INFORMATION: hTREM COMP

<400> SEQUENCE: 10

| | |
|---|---|
| gaattcgcaa ctatgcctct gctgctgctg ctgcctctgc tgtgggctgg cgcactggct | 60 |
| gaactgaggg ccgctaccaa actgaccgaa gaaaagtacg agctgaaaga agggcagacc | 120 |
| ctggacgtga agtgcgatta tactggaa aagttcgcaa gctcccagaa agcctggcag | 180 |
| atcattagag acggagagat gcccaagact ctggcttgta ccgaacgccc ttcaaaaaac | 240 |
| agccacccag tgcaggtcgg ccgaatcatt ctggaggact accacgatca tgggctgctg | 300 |
| cgggtgagaa tggtcaatct gcaggtggag gactccggcc tgtaccagtg cgtcatctat | 360 |
| cagcccccta aggaaccaca tatgctgttc gataggattc gcctggtggt cactaaaggc | 420 |
| ttttctggga ccccggaag taacgagaac agcacccaga acgtgtacaa gatcccaccc | 480 |
| accacaacta aggccctgtg cccctgtat acatctcctc gaaccgtgac acaggcccct | 540 |
| ccaaagagta ccgctgacgt gagcacaccc gattccgaga ttaacctgac aaatgtgact | 600 |
| gacatcatta ggggtaccct ggaggtgctg ttccagggac caggaggagg aagcggagga | 660 |
| ggcagcggcg ggggatctgg ggacctggcc cctcagatgc tgagggagct gcaggaaacc | 720 |
| aacgccgctc tgcaggatgt gcgggagctg ctgagacagc aggtgaagga aatcacattt | 780 |
| ctgaaaaata ctgtgatgga gtgcgacgct tgtggaatgc agccagctag gacacctgga | 840 |
| ctgagcgtgg gaggaggaag tgaggaggga tcaggaggag gaagcatgga tgagaagacc | 900 |
| acaggatgga gaggaggaca cgtggtggaa ggactggctg agagctggga acagctgagg | 960 |
| gctagactgg agcaccatcc acagggacag agggagccag gtccggaat ggacgaaaaa | 1020 |
| actaccggat ggaggggagg acacgtggtg gagggcctgg ccggcgaact ggagcagctg | 1080 |
| agagctcgcc tggaacacca tcctcagggc cagagagagc cagaggacct gtacttccag | 1140 |
| tctcaccatc accatcacca ttaaggatcc | 1170 |

<210> SEQ ID NO 11
<211> LENGTH: 867
<212> TYPE: DNA
<213> ORGANISM: Artificial
<220> FEATURE:
<223> OTHER INFORMATION: hCD83 for tetramer

<400> SEQUENCE: 11

| | |
|---|---|
| gaattcgcca ccatgcctct gctgctgctg ctgccactgc tgtgggctgg cgctctggct | 60 |
| accccagagg tgaaggtggc ttgctccgaa gacgtggatc tgccttgtac agccccctgg | 120 |
| gaccctcagg tgccatacac cgtgagctgg gtgaaactgc tggaggcgg ggaggaacgg | 180 |

```
atggagacac cacaggaaga ccacctgaga gggcagcact atcatcagaa ggggcagaac      240
ggatctttcg atgctcccaa tgaacggcct tacagtctga aaatcagaaa caccacaagc      300
tgcaattccg gcacatatag gtgtactctg caggaccctg atggacagcg caacctgagc      360
ggcaaagtga tcctgcgggt gacaggctgc ccagctcaga gaaaggagga aacttttaag      420
aagtaccggg ccgagggtac cggaggcggg ggatccggag aggaggaag cggaggagga       480 ggatccactc ctgaagtgaa ggtggcttgc agtgaagacg tggatctgcc ctgtaccgcc      540
ccctgggatc ctcaggtgcc atacacagtg tcttgggtga agctgctgga gggaggcgag      600
gaacggatgg agacccctca ggaagaccat ctgagaggcc agcattacca tcagaagggc      660
cagaacgggt cattcgatgc cccaaatgaa aggccctaca gcctgaaaat ccgcaacact      720
acctcttgca atagtggaac ctataggtgt acactgcagg accccgatgg gcagcgcaat      780
ctgtccggca agtgatcct gagggtgact ggctgtcctg ctcagcgcaa agaggaaacc      840
tttaagaaat atagggccga ggggccc                                         867

<210> SEQ ID NO 12
<211> LENGTH: 1143
<212> TYPE: DNA
<213> ORGANISM: Artificial
<220> FEATURE:
<223> OTHER INFORMATION: hDCIR COMP

<400> SEQUENCE: 12
gaattcgcca ccatgccact gctgctgctg ctgccactgc tgtgggctgg agctctggct       60
caccatcacc atcaccatga ggacctgtac ttccagtcca tggatgaaaa gaccacagga      120
tggaggggag gacacgtggt ggagggactg gctggagagc tggaacagct gagggctaga      180
ctggaacacc atcctcaggg ccagagggag ccagggtctg gaatggacga aaaaactacc      240
ggctggagag gcggccatgt cgtcgaaggc ctggccggcg aactggagca gctgagagct      300
aggctggagc accatccaca gggacagagg gaacctggag gaggcagcgg aggaggctcc      360
ggaggaggct ctggcgacct ggccccacag atgctgagag agctgcagga aaccaacgcc      420
gctctgcagg atgtgcggga gctgctgaga cagcaggtga aggaaatcac attcctgaaa      480
aatactgtga tggagtgcga tgcttgtgga atgcagccag ctaggacacc tggactgagc      540
gtgggaggag gcagtggagg aggctcagga ggaggcagcc tggaggtgct gtttcagggc      600
cccagatcta ttgcttttgt catttt cttt caaaaatatt ctcagcttct tgaaaaaaag      660
actacaaaag agctggttca tacaacattg gagtgtgtga aaaaaatat gcccgtggaa      720 gagacagcct ggagctgttg cccaaagaat tggaagtcat ttagttccaa ctgctacttt      780
atttctactg aatcagcatc ttggcaagac agtgagaagg actgtgctag aatggaggct      840
cacctgctgg tgataaacac tcaagaagag caggatttca tcttccagaa tctgcaagaa      900
gaatctgctt attttgtggg gctctcagat ccagaaggtc agcgacattg gcaatgggtt      960
gatcagacac atacaatga agttccaca ttctggcatc cacgtgagcc cagtgatccc      1020
aatgagcgct gcgttgtgct aaatttcgt aaatcaccca aagatgggg ctggaatgat       1080 gttaattgtc ttggtcctca aaggtcagtt tgtgagatga tgaagatcca cttatgagga     1140
tcc                                                                   1143

<210> SEQ ID NO 13
<211> LENGTH: 426
<212> TYPE: DNA
```

<210> SEQ ID NO 13
<211> LENGTH: 426
<212> TYPE: DNA
<213> ORGANISM: Mus musculus

<400> SEQUENCE: 13

```
aagcttgccg ccaccatgcc tctgctgctg ctgctgcctc tgctgtgggc cggggctctg      60
gctcaggtcc agctgcagca gcctggggcc gaactggtcc gaccagggc atctgtgaaa      120
ctgagttgca aggcctctgg atacagtttc acctcatatt ggatgaactg ggtcaaacag      180
cgaccaggac agggactgga gtggatcggc atgattcacc ctagcgactc cgaaacaaga      240
ctgaatcaga gtttaaaga caaggctacc ctgacagtgg ataagagctc ctctacagca      300
tacatgcagc tgagttcacc cactagcgag gactccgccg tctactattg tgctagggat      360
tactctgact atgatgggtt cgcctattgg ggacagggca ctctggtgac cgtcagcgct      420
gctagc                                                                426
```

<210> SEQ ID NO 14
<211> LENGTH: 390
<212> TYPE: DNA
<213> ORGANISM: Mus musculus

<400> SEQUENCE: 14

```
aagcttgccg ccaccatgcc tctgctgctg ctgctgcctc tgctgtgggc tggggctctg      60
gctgatattg tgatgactca gtcacccgct accctgtccg tgacaccagg gaccgggtg      120
agcctgtcct gcagagcctc tcagagtatc tcagattacc tgcactggta tcagcagaag      180
tctcatgaga gtcccaggct gctgatcaag tacgccagcc agtccatctc tggcattcct      240
tcccggttca gtggctcagg gagcggatcc gactttactc tgtctatcaa cagcgtcgag      300
ccagaagatg tgggagtcta ctattgtcag aatggccaca gcttccccct gacctttggc      360
accgggacaa agctggaact gaaacgtacg                                      390
```

<210> SEQ ID NO 15
<211> LENGTH: 446
<212> TYPE: PRT
<213> ORGANISM: Mus musculus

<400> SEQUENCE: 15

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Asp Tyr Ser Asp Tyr Asp Gly Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 16
<211> LENGTH: 214
<212> TYPE: PRT
<213> ORGANISM: Mus musculus

<400> SEQUENCE: 16

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu

```
                      85                  90                  95
Thr Phe Gly Thr Gly Thr Lys Leu Glu Leu Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 17
<211> LENGTH: 429
<212> TYPE: DNA
<213> ORGANISM: Mus musculus

<400> SEQUENCE: 17

```
aagcttgccg ccaccatgcc tctgctgctg ctgctgcctc tgctgtgggc cggagccctg      60
gccgaaatcc agctgcagca gtcaggacct gaactggtga acccggggc ctcagtgaaa     120
gtcagctgca tggcttcagt gtacagcttc accgactaca acatgtattg ggtcaaacag     180
tcccggggga agtctctgga gtggatcgga tacattgacc cttataacgg cgatacatcc     240
tataatcaga agttcaaagg caaggcaact ctgaccgtgg acaagagctc aaacacagcc     300
tttatgcacc tgaattccct gacttctgaa gatagtgctg tctactattg tatcagagga     360
gactacggca atccctttta cctggattat tggggccagg ggaccacact gaccgtgtct     420
agtgctagc                                                             429
```

<210> SEQ ID NO 18
<211> LENGTH: 387
<212> TYPE: DNA
<213> ORGANISM: Mus musculus

<400> SEQUENCE: 18

```
aagcttgccg ccaccatgcc cctgctgctg ctgctgcctc tgctgtgggc cggcgcactg      60
gctcagattg tcctgattca gtctcccgcc atcgtgtccg cttcccctgg ggagaaggtg     120
accatgacat gcagcgtgag ctcctctgtc aactacatgt attggtacca gcagaagagc     180
ggaacatccc ccaaacggtg gatctatgac acttctaaac tgccaagtgg agtcccagca     240
agattcagcg gatccggatc tggaactagt tactcactga ccattagttc aatggaggcc     300
gaagatgccg ctacatacta ttgtcagcag tggacatcta ccccctac ttttggcagc     360
gggaccaatc tggaaatcaa gcgtacg                                         387
```

<210> SEQ ID NO 19
<211> LENGTH: 447
<212> TYPE: PRT
<213> ORGANISM: Mus musculus

<400> SEQUENCE: 19

```
Glu Ile Gln Leu Gln Gln Ser Gly Pro Glu Leu Val Lys Pro Gly Ala
 1               5                  10                  15

Ser Val Lys Val Ser Cys Met Ala Ser Val Tyr Ser Phe Thr Asp Tyr
            20                  25                  30

Asn Met Tyr Trp Val Lys Gln Ser Arg Gly Lys Ser Leu Glu Trp Ile
            35                  40                  45

Gly Tyr Ile Asp Pro Tyr Asn Gly Asp Thr Ser Tyr Asn Gln Lys Phe
50                  55                  60

Lys Gly Lys Ala Thr Leu Thr Val Asp Lys Ser Ser Asn Thr Ala Phe
65                  70                  75                  80

Met His Leu Asn Ser Leu Thr Ser Glu Asp Ser Ala Val Tyr Tyr Cys
                85                  90                  95

Ile Arg Gly Asp Tyr Gly Asn Pro Phe Tyr Leu Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 20
<211> LENGTH: 213
<212> TYPE: PRT
<213> ORGANISM: Mus musculus

<400> SEQUENCE: 20

Gln Ile Val Leu Ile Gln Ser Pro Ala Ile Val Ser Ala Ser Pro Gly
1               5                   10                  15

Glu Lys Val Thr Met Thr Cys Ser Val Ser Ser Ser Val Asn Tyr Met
                20                  25                  30

Tyr Trp Tyr Gln Gln Lys Ser Gly Thr Ser Pro Lys Arg Trp Ile Tyr
            35                  40                  45

Asp Thr Ser Lys Leu Pro Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Ser Asn Pro Pro Thr
                85                  90                  95

Phe Gly Ser Gly Thr Asn Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 21
<211> LENGTH: 426
<212> TYPE: DNA
<213> ORGANISM: Mus musculus

<400> SEQUENCE: 21
aagcttgccg ccaccatgcc cctgctgctg ctgctgcctc tgctgtgggc cggagccctg      60
gccgaagtcc agctgcagca gtctggcgct gagtttgtga agccaggggc aagcgtgaag     120
ctgtcctgca ccgcctctgg attcaacatc aaagacacat acattcactg ggtcaatcag     180
cggcccgagc agggactgga atggatcggc agaattgacc ccgccaacga cgatactaag     240
tacgatccta attttcaggg caaagctacc atcacatccg acactagctc caacaccgca     300
tatgtgcagc tgtctagtct gacaagcgag gatactgccg tctactattg tgcttcaagc     360
gacaattccg attcttggtt cgcctattgg ggccagggga cactggtgag tgtctcagct     420
gctagc                                                                426

<210> SEQ ID NO 22
<211> LENGTH: 387
<212> TYPE: DNA
<213> ORGANISM: Mus musculus

<400> SEQUENCE: 22

```
aagcttgccg ccaccatgcc cctgctgctg ctgctgcctc tgctgtgggc tggagccctg      60
gcccagattg tcctgactca gtcccccgct attatgtccg cttcaccagg ggagaaggtg     120
accatcacat gcagtgtgag ctcctctgtc aacttcatga attggtacca gcagaagctg     180
ggaagttcac ccaaactgtg gatctacgac accagcaaac tggcaccagg agtccctgca     240
cggttttcag gaagcggatc cggaacttct tacagtctga ccatcagctc catggagaca     300
gaagatgccg cttcctactt ctgtcaccag tggtctagtt attctctgac atttggcgct     360
gggactaagc tggaactgaa acgtacg                                          387
```

<210> SEQ ID NO 23
<211> LENGTH: 446
<212> TYPE: PRT
<213> ORGANISM: Mus musculus

<400> SEQUENCE: 23

```
Glu Val Gln Leu Gln Gln Ser Gly Ala Glu Phe Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Asn Gln Arg Pro Glu Gln Gly Leu Glu Trp Ile
        35                  40                  45

Gly Arg Ile Asp Pro Ala Asn Asp Asp Thr Lys Tyr Asp Pro Asn Phe
    50                  55                  60

Gln Gly Lys Ala Thr Ile Thr Ser Asp Thr Ser Asn Thr Ala Tyr
65                  70                  75                  80

Val Gln Leu Ser Ser Leu Thr Ser Glu Asp Thr Ala Val Tyr Tyr Cys
                85                  90                  95

Ala Ser Ser Asp Asn Ser Asp Ser Trp Phe Ala Tyr Trp Gly Gln Gly
            100                 105                 110

Thr Leu Val Ser Val Ser Ala Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 24
<211> LENGTH: 213
<212> TYPE: PRT
<213> ORGANISM: Mus musculus

<400> SEQUENCE: 24

Gln Ile Val Leu Thr Gln Ser Pro Ala Ile Met Ser Ala Ser Pro Gly
1               5                   10                  15

Glu Lys Val Thr Ile Thr Cys Ser Val Ser Ser Ser Val Asn Phe Met
            20                  25                  30

Asn Trp Tyr Gln Gln Lys Leu Gly Ser Ser Pro Lys Leu Trp Ile Tyr
        35                  40                  45

Asp Thr Ser Lys Leu Ala Pro Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Ser Tyr Phe Cys His Gln Trp Ser Ser Tyr Ser Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
        195                 200                 205

Asn Arg Gly Glu Cys
    210

<210> SEQ ID NO 25
<211> LENGTH: 420
<212> TYPE: DNA
<213> ORGANISM: Mus musculus

<400> SEQUENCE: 25
aagcttgccg ccaccatgcc tctgctgctg ctgctgcctc tgctgtgggc cggggctctg      60
gccgagattc agctgcagca gtctggacct gacctggtga aacccggcac ctctgtgaaa     120
gtcagttgca aggcttctgg gtacagtttc acagactata acatgcactg ggtgaaacag     180
tctcatggga agagcctgga gtggatcgga tacgtcgacc cttatgatgg cggactagc     240 tccaatcaga agttcaaagg caaggcaact ctgaccgtgg ataaatctag ttcaacagcc     300
tttatgcacc tgaagtcact gactagcgag gactccgccg tgtactattg tgctcgggaa     360
gtcccctact attttgatta ctggggacag ggcaccacac tgacagtgag ctccgctagc     420

<210> SEQ ID NO 26
<211> LENGTH: 384
<212> TYPE: DNA
<213> ORGANISM: Mus musculus

<400> SEQUENCE: 26
aagcttgccg ccaccatgcc cctgctgctg ctgctgcccc tgctgtgggc cggagctctg      60
gctcagattg tgctgactca gtcccctagt attatgtccg cctcccctgg cgagaaggtg     120
accatgacat gcgtcgccag ctcctctgtg acatacatgt attggtacca gcagaaaagc     180
ggaacctccc cacaggacgg cttcatgaca cacccactgg caagcggagt cccagcacgg     240
tttatcggag aggatctggc acaagttat tcactgacta ttagtaacat ggaggccgaa     300
gatgccgcta cttactattg tccccattgg aacactaatc ccctaccttc ggctctggg     360 accaagctgg aaatcaatcg tacg                                            384

<210> SEQ ID NO 27
<211> LENGTH: 444
<212> TYPE: PRT
<213> ORGANISM: Mus musculus

<400> SEQUENCE: 27

Glu Ile Gln Leu Gln Gln Ser Gly Pro Asp Leu Val Lys Pro Gly Thr
1               5                   10                  15

Ser Val Lys Val Ser Cys Lys Ala Ser Gly Tyr Ser Phe Thr Asp Tyr
            20                  25                  30

Asn Met His Trp Val Lys Gln Ser His Gly Lys Ser Leu Glu Trp Ile
        35                  40                  45

Gly Tyr Val Asp Pro Tyr Asp Gly Gly Thr Ser Ser Asn Gln Lys Phe
    50                  55                  60

Lys Gly Lys Ala Thr Leu Thr Val Asp Lys Ser Ser Ser Thr Ala Phe
65                  70                  75                  80

Met His Leu Lys Ser Leu Thr Ser Glu Asp Ser Ala Val Tyr Tyr Cys
                85                  90                  95

Ala Arg Glu Val Pro Tyr Tyr Phe Asp Tyr Trp Gly Gln Gly Thr Thr
            100                 105                 110

Leu Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 28
<211> LENGTH: 212
<212> TYPE: PRT
<213> ORGANISM: Mus musculus

<400> SEQUENCE: 28

Gln Ile Val Leu Thr Gln Ser Pro Ser Ile Met Ser Ala Ser Pro Gly
1               5                   10                  15

Glu Lys Val Thr Met Thr Cys Val Ala Ser Ser Ser Val Thr Tyr Met
            20                  25                  30

Tyr Trp Tyr Gln Gln Lys Ser Gly Thr Ser Pro Gln Asp Gly Phe Met

```
                35                  40                  45
Thr His Pro Leu Ala Ser Gly Val Pro Ala Arg Phe Ile Gly Gly
    50                  55                  60
Ser Gly Thr Ser Tyr Ser Leu Thr Ile Ser Asn Met Glu Ala Glu Asp
65                  70                  75                  80
Ala Ala Thr Tyr Tyr Cys Pro His Trp Asn Thr Asn Pro Pro Thr Phe
                85                  90                  95
Gly Ser Gly Thr Lys Leu Glu Ile Asn Arg Thr Val Ala Ala Pro Ser
            100                 105                 110
Val Phe Ile Phe Pro Pro Ser Asp Glu Gln Leu Lys Ser Gly Thr Ala
            115                 120                 125
Ser Val Val Cys Leu Leu Asn Asn Phe Tyr Pro Arg Glu Ala Lys Val
    130                 135                 140
Gln Trp Lys Val Asp Asn Ala Leu Gln Ser Gly Asn Ser Gln Glu Ser
145                 150                 155                 160
Val Thr Glu Gln Asp Ser Lys Asp Ser Thr Tyr Ser Leu Ser Ser Thr
                165                 170                 175
Leu Thr Leu Ser Lys Ala Asp Tyr Glu Lys His Lys Val Tyr Ala Cys
            180                 185                 190
Glu Val Thr His Gln Gly Leu Ser Ser Pro Val Thr Lys Ser Phe Asn
            195                 200                 205
Arg Gly Glu Cys
    210

<210> SEQ ID NO 29
<211> LENGTH: 360
<212> TYPE: DNA
<213> ORGANISM: Mus musculus

<400> SEQUENCE: 29
gaagtgcagc tggtggagtc tgggggaggc ttagtgaagc ctggagggtc cctgaaactc      60
tcctgtgcag cctctggatt ctctttcagt gactattaca tgtattgggt tcgccagact     120
ccggaaaaga ggctggagtg ggtcgcagcc attagtgatg atagtactta cacctactat     180
ccagacagtg tgaaggggcg attcaccatc tccagagaca tgccaagaa caacctgtac      240 ctgcaaatga gcagtctgaa gtctgaggac acagccatgt attactgtgc aagaggggg      300 tatggtaacc tctatgctat ggactactgg ggtcaaggaa cctcagtcac cgtctcctca     360

<210> SEQ ID NO 30
<211> LENGTH: 327
<212> TYPE: DNA
<213> ORGANISM: Mus musculus

<400> SEQUENCE: 30
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gctcgcttca gtggcagtgg gtctgggacc tcttactctc tcacaatcag cagcatggag     240
gctgaagatg ctgccactta ttactgccac cagtatcatc gttccccatt cacgttcggc     300
tcggggacaa agttggaaat aaaacgg                                          327

<210> SEQ ID NO 31
<211> LENGTH: 120
<212> TYPE: PRT
```

<213> ORGANISM: Mus musculus

<400> SEQUENCE: 31

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Tyr Met Tyr Trp Val Arg Gln Thr Pro Glu Lys Arg Leu Glu Trp Val
        35                  40                  45

Ala Ala Ile Ser Asp Asp Ser Thr Tyr Thr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Gly Gly Tyr Gly Asn Leu Tyr Ala Met Asp Tyr Trp Gly Gln
            100                 105                 110

Gly Thr Ser Val Thr Val Ser Ser
        115                 120

<210> SEQ ID NO 32
<211> LENGTH: 109
<212> TYPE: PRT
<213> ORGANISM: Mus musculus

<400> SEQUENCE: 32

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Phe Thr Phe Gly Ser Gly Thr Lys Leu Glu Ile Lys Arg
            100                 105

<210> SEQ ID NO 33
<211> LENGTH: 360
<212> TYPE: DNA
<213> ORGANISM: Mus musculus

<400> SEQUENCE: 33
gaggtccagc tgcagcagtc tggacctgag gtggtaaagc ctgggacttc agtgaagatg      60
tcctgcaagg cttctggata cacattcact aactatgtta tgcactgggt gaggcagaag    120
cctgggcagg gccttgaatg ggttggatgg attaatccct caatgatgg tacaaattat     180 aatgagaact tcaaaacaa ggccacactg acttcagaca atcctccag cacagcctac      240 atggagctca gcagcctgac ctctgaggac tctgcggtct attactgtgc aagatccggt    300
tttattacta cacttataga agactactgg ggccaaggca ccactctcac agtctcctca    360

<210> SEQ ID NO 34

```
<211> LENGTH: 321
<212> TYPE: DNA
<213> ORGANISM: Mus musculus

<400> SEQUENCE: 34
aacattgtga tgacccaatc tcccaaatac atgtccatgt cagtaggaga gagggtcacc      60
ttgacctgca aggccagtga gagtgtggga agttttgtat cctggtatca acagaaagca     120
gaccagtctc ctaacctact gatatacggg gcatccaacc ggtacactgg ggtccccgat     180
cgcttcacag gcagtggatc tgcaagagat tcactctga ccatcagtag tgtgcaggct      240
aaagaccttg cagaatatta ctgtggacag tattacaccc atcccacgtt cggtgctggg     300
accaagctgg agctgaaacg g                                                321

<210> SEQ ID NO 35
<211> LENGTH: 120
<212> TYPE: PRT
<213> ORGANISM: Mus musculus

<400> SEQUENCE: 35

Glu Val Gln Leu Gln Gln Ser Gly Pro Glu Val Val Lys Pro Gly Thr
1               5                   10                  15

Ser Val Lys Met Ser Cys Lys Ala Ser Gly Tyr Thr Phe Thr Asn Tyr
            20                  25                  30

Val Met His Trp Val Arg Gln Lys Pro Gly Gln Gly Leu Glu Trp Val
        35                  40                  45

Gly Trp Ile Asn Pro Phe Asn Asp Gly Thr Asn Tyr Asn Glu Asn Phe
    50                  55                  60

Lys Asn Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Phe Ile Thr Thr Leu Ile Glu Asp Tyr Trp Gly Gln
            100                 105                 110

Gly Thr Thr Leu Thr Val Ser Ser
        115                 120

<210> SEQ ID NO 36
<211> LENGTH: 107
<212> TYPE: PRT
<213> ORGANISM: Mus musculus

<400> SEQUENCE: 36

Asn Ile Val Met Thr Gln Ser Pro Lys Tyr Met Ser Met Ser Val Gly
1               5                   10                  15

Glu Arg Val Thr Leu Thr Cys Lys Ala Ser Glu Ser Val Gly Ser Phe
            20                  25                  30

Val Ser Trp Tyr Gln Gln Lys Ala Asp Gln Ser Pro Asn Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Arg Asp Phe Thr Leu Thr Ile Ser Ser Val Gln Ala
65                  70                  75                  80

Lys Asp Leu Ala Glu Tyr Tyr Cys Gly Gln Tyr Tyr Thr His Pro Thr
                85                  90                  95

Phe Gly Ala Gly Thr Lys Leu Glu Leu Lys Arg
            100                 105
```

```
<210> SEQ ID NO 37
<211> LENGTH: 200
<212> TYPE: PRT
<213> ORGANISM: Artificial sequence
<220> FEATURE:
<223> OTHER INFORMATION: Type II 1.0 PGLYRP1

<400> SEQUENCE: 37

Met Asn Trp His Met Ile Ile Ser Gly Leu Ile Val Val Leu Lys
1               5                   10                  15

Val Val Gly Met Thr Leu Phe Leu Leu Gln Glu Thr Glu Asp Pro Ala
            20                  25                  30

Cys Cys Ser Pro Ile Val Pro Arg Asn Glu Trp Lys Ala Leu Ala Ser
        35                  40                  45

Glu Cys Ala Gln His Leu Ser Leu Pro Leu Arg Tyr Val Val Val Ser
    50                  55                  60

His Thr Ala Gly Ser Ser Cys Asn Thr Pro Ala Ser Cys Gln Gln Gln
65                  70                  75                  80

Ala Arg Asn Val Gln His Tyr His Met Lys Thr Leu Gly Trp Cys Asp
                85                  90                  95

Val Gly Tyr Asn Phe Leu Ile Gly Glu Asp Gly Leu Val Tyr Glu Gly
            100                 105                 110

Arg Gly Trp Asn Phe Thr Gly Ala His Ser Gly His Leu Trp Asn Pro
        115                 120                 125

Met Ser Ile Gly Ile Ser Phe Met Gly Asn Tyr Met Asp Arg Val Pro
    130                 135                 140

Thr Pro Gln Ala Ile Arg Ala Ala Gln Gly Leu Leu Ala Cys Gly Val
145                 150                 155                 160

Ala Gln Gly Ala Leu Arg Ser Asn Tyr Val Leu Lys Gly His Arg Asp
                165                 170                 175

Val Gln Arg Thr Leu Ser Pro Gly Asn Gln Leu Tyr His Leu Ile Gln
            180                 185                 190

Asn Trp Pro His Tyr Arg Ser Pro
        195                 200

<210> SEQ ID NO 38
<211> LENGTH: 210
<212> TYPE: PRT
<213> ORGANISM: Artificial sequence
<220> FEATURE:
<223> OTHER INFORMATION: Type II 2.0 PGLYRP1

<400> SEQUENCE: 38

Met Asn Trp His Met Ile Ile Ser Gly Leu Ile Val Val Leu Leu
1               5                   10                  15

Val Val Gly Met Thr Leu Phe Leu Leu Asp Tyr Lys Asp Asp Asp
            20                  25                  30

Lys Gly Ser Gln Glu Thr Glu Asp Pro Ala Cys Cys Ser Pro Ile Val
        35                  40                  45

Pro Arg Asn Glu Trp Lys Ala Leu Ala Ser Glu Cys Ala Gln His Leu
    50                  55                  60

Ser Leu Pro Leu Arg Tyr Val Val Val Ser His Thr Ala Gly Ser Ser
65                  70                  75                  80

Cys Asn Thr Pro Ala Ser Cys Gln Gln Gln Ala Arg Asn Val Gln His
                85                  90                  95

Tyr His Met Lys Thr Leu Gly Trp Cys Asp Val Gly Tyr Asn Phe Leu
            100                 105                 110
```

```
Ile Gly Glu Asp Gly Leu Val Tyr Glu Gly Arg Gly Trp Asn Phe Thr
            115                 120                 125

Gly Ala His Ser Gly His Leu Trp Asn Pro Met Ser Ile Gly Ile Ser
    130                 135                 140

Phe Met Gly Asn Tyr Met Asp Arg Val Pro Thr Pro Gln Ala Ile Arg
145                 150                 155                 160

Ala Ala Gln Gly Leu Leu Ala Cys Gly Val Ala Gln Gly Ala Leu Arg
                165                 170                 175

Ser Asn Tyr Val Leu Lys Gly His Arg Asp Val Gln Arg Thr Leu Ser
            180                 185                 190

Pro Gly Asn Gln Leu Tyr His Leu Ile Gln Asn Trp Pro His Tyr Arg
        195                 200                 205

Ser Pro
    210

<210> SEQ ID NO 39
<211> LENGTH: 8
<212> TYPE: PRT
<213> ORGANISM: Artificial sequence
<220> FEATURE:
<223> OTHER INFORMATION: Epitope tag

<400> SEQUENCE: 39

Asp Tyr Lys Asp Asp Asp Asp Lys
1               5

<210> SEQ ID NO 40
<211> LENGTH: 589
<212> TYPE: PRT
<213> ORGANISM: Homo sapiens

<400> SEQUENCE: 40

Met Asn Trp His Met Ile Ile Ser Gly Leu Ile Val Val Val Leu Leu
1               5                   10                  15

Val Val Gly Met Thr Leu Phe Leu Asp Tyr Lys Asp Asp Asp Asp Lys
            20                  25                  30

Asp Lys Ser Leu Pro Leu Leu Met Asp Ser Val Ile Gln Ala Leu Ala
        35                  40                  45

Glu Leu Glu Gln Lys Val Pro Ala Ala Lys Thr Arg His Thr Ala Ser
    50                  55                  60

Ala Trp Leu Met Ser Ala Pro Asn Ser Gly Pro His Asn Arg Leu Tyr
65                  70                  75                  80

His Phe Leu Leu Gly Ala Trp Ser Leu Asn Ala Thr Glu Leu Asp Pro
                85                  90                  95

Cys Pro Leu Ser Pro Glu Leu Leu Gly Leu Thr Lys Gly Val Ala Arg
            100                 105                 110

His Asp Val Arg Glu Gly Lys Glu Tyr Gly Val Val Leu Ala Pro Asp
        115                 120                 125

Gly Ser Thr Val Ala Val Glu Pro Leu Leu Ala Gly Leu Glu Ala Gly
    130                 135                 140

Leu Gln Gly Arg Arg Val Ile Asn Leu Pro Leu Asp Ser Met Ala Ala
145                 150                 155                 160

Pro Trp Glu Thr Gly Asp Thr Phe Pro Asp Val Val Ala Ile Ala Pro
                165                 170                 175

Asp Val Arg Ala Thr Ser Ser Pro Gly Leu Arg Asp Gly Ser Pro Asp
            180                 185                 190
```

Val Thr Thr Ala Asp Ile Gly Ala Asn Thr Pro Asp Ala Thr Lys Gly
        195                 200                 205

Cys Pro Asp Val Gln Ala Ser Leu Pro Asp Ala Lys Ala Lys Ser Pro
210                 215                 220

Pro Thr Met Val Asp Ser Leu Leu Ala Val Thr Leu Ala Gly Asn Leu
225                 230                 235                 240

Gly Leu Thr Phe Leu Arg Gly Ser Gln Thr Gln Ser His Pro Asp Leu
                245                 250                 255

Gly Thr Glu Gly Cys Trp Asp Gln Leu Ser Ala Pro Arg Thr Phe Thr
            260                 265                 270

Leu Leu Asp Pro Lys Ala Ser Leu Leu Thr Met Ala Phe Leu Asn Gly
        275                 280                 285

Ala Leu Asp Gly Val Ile Leu Gly Asp Tyr Leu Ser Arg Thr Pro Glu
    290                 295                 300

Pro Arg Pro Ser Leu Ser His Leu Leu Ser Gln Tyr Tyr Gly Ala Gly
305                 310                 315                 320

Val Ala Arg Asp Pro Gly Phe Arg Ser Asn Phe Arg Gln Asn Gly
                325                 330                 335

Ala Ala Leu Thr Ser Ala Ser Ile Leu Ala Gln Gln Val Trp Gly Thr
                340                 345                 350

Leu Val Leu Leu Gln Arg Leu Glu Pro Val His Leu Gln Leu Gln Cys
            355                 360                 365

Met Ser Gln Glu Gln Leu Ala Gln Val Ala Ala Asn Ala Thr Lys Glu
        370                 375                 380

Phe Thr Glu Ala Phe Leu Gly Cys Pro Ala Ile His Pro Arg Cys Arg
385                 390                 395                 400

Trp Gly Ala Ala Pro Tyr Arg Gly Arg Pro Lys Leu Leu Gln Leu Pro
                405                 410                 415

Leu Gly Phe Leu Tyr Val His His Thr Tyr Val Pro Ala Pro Pro Cys
            420                 425                 430

Thr Asp Phe Thr Arg Cys Ala Ala Asn Met Arg Ser Met Gln Arg Tyr
        435                 440                 445

His Gln Asp Thr Gln Gly Trp Gly Asp Ile Gly Tyr Ser Phe Val Val
    450                 455                 460

Gly Ser Asp Gly Tyr Val Tyr Glu Gly Arg Gly Trp His Trp Val Gly
465                 470                 475                 480

Ala His Thr Leu Gly His Asn Ser Arg Gly Phe Gly Val Ala Ile Val
                485                 490                 495

Gly Asn Tyr Thr Ala Ala Leu Pro Thr Glu Ala Ala Leu Arg Thr Val
            500                 505                 510

Arg Asp Thr Leu Pro Ser Cys Ala Val Arg Ala Gly Leu Leu Arg Pro
        515                 520                 525

Asp Tyr Ala Leu Leu Gly His Arg Gln Leu Val Arg Thr Asp Cys Pro
    530                 535                 540

Gly Asp Ala Leu Phe Asp Leu Leu Arg Thr Trp Pro His Phe Thr Ala
545                 550                 555                 560

Thr Val Lys Pro Arg Pro Ala Arg Ser Val Ser Lys Arg Ser Arg Arg
                565                 570                 575

Glu Pro Pro Pro Arg Thr Leu Pro Ala Thr Asp Leu Gln
            580                 585

<210> SEQ ID NO 41
<211> LENGTH: 355
<212> TYPE: PRT

<213> ORGANISM: Homo sapiens

<400> SEQUENCE: 41

```
Met Asn Trp His Met Ile Ile Ser Gly Leu Ile Val Val Leu Leu
1               5                   10                  15

Val Val Gly Met Thr Leu Phe Leu Leu Asp Tyr Lys Asp Asp Asp
            20                  25                  30

Asp Lys Trp Asp Thr Pro Thr Ile Val Ser Arg Lys Glu Trp Gly Ala
        35                  40                  45

Arg Pro Leu Ala Cys Arg Ala Leu Leu Thr Leu Pro Val Ala Tyr Ile
    50                  55                  60

Ile Thr Gln Leu Pro Gly Met Gln Cys Gln Gln Ser Val Cys Ser
65                  70                  75                  80

Gln Met Leu Arg Gly Leu Gln Ser His Ser Val Tyr Thr Ile Gly Trp
                85                  90                  95

Cys Asp Val Ala Tyr Asn Phe Leu Val Gly Asp Asp Gly Arg Val Tyr
            100                 105                 110

Glu Gly Val Gly Trp Asn Ile Gln Gly Leu His Thr Gln Gly Tyr Asn
        115                 120                 125

Asn Ile Ser Leu Gly Ile Ala Phe Phe Gly Asn Lys Ile Gly Ser Ser
    130                 135                 140

Pro Ser Pro Ala Ala Leu Ser Ala Ala Glu Gly Leu Ile Ser Tyr Ala
145                 150                 155                 160

Ile Gln Lys Gly His Leu Ser Pro Arg Tyr Ile Gln Pro Leu Leu Leu
                165                 170                 175

Lys Glu Glu Thr Cys Leu Asp Pro Gln His Pro Val Met Pro Arg Lys
            180                 185                 190

Val Cys Pro Asn Ile Ile Lys Arg Ser Ala Trp Glu Ala Arg Glu Thr
        195                 200                 205

His Cys Pro Lys Met Asn Leu Pro Ala Lys Tyr Val Ile Ile Ile His
    210                 215                 220

Thr Ala Gly Thr Ser Cys Thr Val Ser Thr Asp Cys Gln Thr Val Val
225                 230                 235                 240

Arg Asn Ile Gln Ser Phe His Met Asp Thr Arg Asn Phe Cys Asp Ile
                245                 250                 255

Gly Tyr His Phe Leu Val Gly Gln Asp Gly Val Tyr Glu Gly Val Gly
            260                 265                 270

Trp His Ile Gln Gly Ser His Thr Tyr Gly Phe Asn Asp Ile Ala Leu
        275                 280                 285

Gly Ile Ala Phe Ile Gly Tyr Phe Val Glu Lys Pro Pro Asn Ala Ala
    290                 295                 300

Ala Leu Glu Ala Ala Gln Asp Leu Ile Gln Cys Ala Val Val Glu Gly
305                 310                 315                 320

Tyr Leu Thr Pro Asn Tyr Leu Leu Met Gly His Ser Asp Val Asn Ile
                325                 330                 335

Leu Ser Pro Gly Gln Ala Leu Tyr Asn Ile Ile Ser Thr Trp Pro His
            340                 345                 350

Phe Lys His
        355
```

<210> SEQ ID NO 42
<211> LENGTH: 390
<212> TYPE: PRT
<213> ORGANISM: Homo sapiens

<400> SEQUENCE: 42

```
Met Asn Trp His Met Ile Ile Ser Gly Leu Ile Val Val Leu Leu
1               5                   10                  15

Val Val Gly Met Thr Leu Phe Leu Leu Asp Tyr Lys Asp Asp Asp
            20                  25                  30

Asp Lys Asp Ser Ser Trp Asn Lys Thr Gln Ala Lys Gln Val Ser Glu
        35                  40                  45

Gly Leu Gln Tyr Leu Phe Glu Asn Ile Ser Gln Leu Thr Glu Lys Gly
    50                  55                  60

Leu Pro Thr Asp Val Ser Thr Thr Val Ser Arg Lys Ala Trp Gly Ala
65              70                  75                  80

Glu Ala Val Gly Cys Ser Ile Gln Leu Thr Thr Pro Val Asn Val Leu
                85                  90                  95

Val Ile His His Val Pro Gly Leu Glu Cys His Asp Gln Thr Val Cys
                100                 105                 110

Ser Gln Arg Leu Arg Glu Leu Gln Ala His His Val His Asn Asn Ser
            115                 120                 125

Gly Cys Asp Val Ala Tyr Asn Phe Leu Val Gly Asp Asp Gly Arg Val
    130                 135                 140

Tyr Glu Gly Val Gly Trp Asn Ile Gln Gly Val His Thr Gln Gly Tyr
145                 150                 155                 160

Asn Asn Ile Ser Leu Gly Phe Ala Phe Gly Thr Lys Lys Gly His
                165                 170                 175

Ser Pro Ser Pro Ala Ala Leu Ser Ala Met Glu Asn Leu Ile Thr Tyr
            180                 185                 190

Ala Val Gln Lys Gly His Leu Ser Ser Ser Tyr Val Gln Pro Leu Leu
        195                 200                 205

Gly Lys Gly Glu Asn Cys Leu Ala Pro Arg Gln Lys Thr Ser Leu Lys
    210                 215                 220

Lys Ala Cys Pro Gly Val Val Pro Arg Ser Val Trp Gly Ala Arg Glu
225                 230                 235                 240

Thr His Cys Pro Arg Met Thr Leu Pro Ala Lys Tyr Gly Ile Ile Ile
                245                 250                 255

His Thr Ala Gly Arg Thr Cys Asn Ile Ser Asp Glu Cys Arg Leu Leu
            260                 265                 270

Val Arg Asp Ile Gln Ser Phe Tyr Ile Asp Arg Leu Lys Ser Cys Asp
        275                 280                 285

Ile Gly Tyr Asn Phe Leu Val Gly Gln Asp Gly Ala Ile Tyr Glu Gly
    290                 295                 300

Val Gly Trp Asn Val Gln Gly Ser Ser Thr Pro Gly Tyr Asp Asp Ile
305                 310                 315                 320

Ala Leu Gly Ile Thr Phe Met Gly Thr Phe Thr Gly Ile Pro Pro Asn
                325                 330                 335

Ala Ala Ala Leu Glu Ala Gln Asp Leu Ile Gln Cys Ala Met Val
            340                 345                 350

Lys Gly Tyr Leu Thr Pro Asn Tyr Leu Leu Val Gly His Ser Asp Val
        355                 360                 365

Ala Arg Thr Leu Ser Pro Gly Gln Ala Leu Tyr Asn Ile Ile Ser Thr
    370                 375                 380

Trp Pro His Phe Lys His
385                 390
```

<210> SEQ ID NO 43

<211> LENGTH: 1317
<212> TYPE: DNA
<213> ORGANISM: Artificial sequence
<220> FEATURE:
<223> OTHER INFORMATION: huCD33-huTrem1 ECD(aa17-200)-Fc6mut

<400> SEQUENCE: 43

```
gaattcgcaa ctatgcctct gctgctgctg ctgcctctgc tgtgggctgg cgcactggct      60
gaactgaggg ccgctaccaa actgaccgaa gaaaagtacg agctgaaaga agggcagacc     120
ctggacgtga agtgcgatta tacactggaa aagttcgcaa gctcccagaa agcctggcag     180
atcattagag acggagagat gcccaagact ctggcttgta ccgaacgccc ttcaaaaaac     240
agccacccag tgcaggtcgg ccgaatcatt ctggaggact accacgatca tgggctgctg     300
cgggtgagaa tggtcaatct gcaggtggag gactccggcc tgtaccagtg cgtcatctat     360
cagcccccta aggaaccaca tatgctgttc gataggattc gcctggtggt cactaaaggc     420
ttttctggga cccccggaag taacgagaac agcacccaga acgtgtacaa gatcccaccc     480
accacaacta aggccctgtg cccctgtat acatctcctc gaaccgtgac acaggcccct     540
ccaaagagta ccgctgacgt gagcacaccc gattccgaga ttaacctgac aaatgtgact     600
gacatcatta ggggtaccga gcccaaatct tctgacaaaa ctcacacatg cccaccgtgc     660
ccagcacctg aagccgaggg ggcaccgtca gtcttcctct ccccccaaa acccaaggac     720
accctcatga tctcccggac ccctgaggtc acatgcgtgg tggtggacgt gagccacgaa     780
gaccctgagg tcaagttcaa ctggtacgtg gacggcgtgg aggtgcataa tgccaagaca     840
aagccgcggg aggagcagta caacagcacg taccgtgtgg tcagcgtcct caccgtcctg     900
caccaggact ggctgaatgg caaggagtac aagtgcaagg tctccaacaa agccctccca     960
tcctccatcg agaaaaccat ctccaaagcc aagggcagc cccgagaacc acaggtgtac    1020
accctgcccc catcccggga ggagatgacc aagaaccagg tcagcctgac ctgcctggtc    1080
aaaggcttct atcccagcga catcgccgtg gagtgggaga gcaatgggca gccggagaac    1140
aactacaaga ccacgcctcc cgtgctggac tccgacggct ccttcttcct ctatagcaag    1200
ctcaccgtgg acaagagcag gtggcagcag gggaacgtct tctcatgctc cgtgatgcat    1260
gaggctctgc acaaccacta cacgcagaag agcctctccc tgtccccggg taaatga      1317
```

<210> SEQ ID NO 44
<211> LENGTH: 434
<212> TYPE: PRT
<213> ORGANISM: Artificial sequence
<220> FEATURE:
<223> OTHER INFORMATION: huCD33-huTrem1 ECD(aa17-200)-Fc6mut

<400> SEQUENCE: 44

```
Met Pro Leu Leu Leu Leu Leu Pro Leu Leu Trp Ala Gly Ala Leu Ala
 1               5                  10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95
```

-continued

Arg Val Arg Met Val Asn Leu Gln Val Glu Asp Ser Gly Leu Tyr Gln
            100                 105                 110
Cys Val Ile Tyr Gln Pro Pro Lys Glu Pro His Met Leu Phe Asp Arg
            115                 120                 125
Ile Arg Leu Val Val Thr Lys Gly Phe Ser Gly Thr Pro Gly Ser Asn
130                 135                 140
Glu Asn Ser Thr Gln Asn Val Tyr Lys Ile Pro Pro Thr Thr Thr Lys
145                 150                 155                 160
Ala Leu Cys Pro Leu Tyr Thr Ser Pro Arg Thr Val Thr Gln Ala Pro
                165                 170                 175
Pro Lys Ser Thr Ala Asp Val Ser Thr Pro Asp Ser Glu Ile Asn Leu
            180                 185                 190
Thr Asn Val Thr Asp Ile Ile Arg Gly Thr Glu Pro Lys Ser Ser Asp
            195                 200                 205
Lys Thr His Thr Cys Pro Pro Cys Pro Ala Pro Glu Ala Glu Gly Ala
210                 215                 220
Pro Ser Val Phe Leu Phe Pro Pro Lys Pro Lys Asp Thr Leu Met Ile
225                 230                 235                 240
Ser Arg Thr Pro Glu Val Thr Cys Val Val Val Asp Val Ser His Glu
                245                 250                 255
Asp Pro Glu Val Lys Phe Asn Trp Tyr Val Asp Gly Val Glu Val His
            260                 265                 270
Asn Ala Lys Thr Lys Pro Arg Glu Glu Gln Tyr Asn Ser Thr Tyr Arg
            275                 280                 285
Val Val Ser Val Leu Thr Val Leu His Gln Asp Trp Leu Asn Gly Lys
290                 295                 300
Glu Tyr Lys Cys Lys Val Ser Asn Lys Ala Leu Pro Ser Ser Ile Glu
305                 310                 315                 320
Lys Thr Ile Ser Lys Ala Lys Gly Gln Pro Arg Glu Pro Gln Val Tyr
                325                 330                 335
Thr Leu Pro Pro Ser Arg Glu Glu Met Thr Lys Asn Gln Val Ser Leu
            340                 345                 350
Thr Cys Leu Val Lys Gly Phe Tyr Pro Ser Asp Ile Ala Val Glu Trp
            355                 360                 365
Glu Ser Asn Gly Gln Pro Glu Asn Asn Tyr Lys Thr Thr Pro Pro Val
370                 375                 380
Leu Asp Ser Asp Gly Ser Phe Phe Leu Tyr Ser Lys Leu Thr Val Asp
385                 390                 395                 400
Lys Ser Arg Trp Gln Gln Gly Asn Val Phe Ser Cys Ser Val Met His
                405                 410                 415
Glu Ala Leu His Asn His Tyr Thr Gln Lys Ser Leu Ser Leu Ser Pro
            420                 425                 430
Gly Lys

<210> SEQ ID NO 45
<211> LENGTH: 1206
<212> TYPE: DNA
<213> ORGANISM: Artificial sequence
<220> FEATURE:
<223> OTHER INFORMATION: huCD33-huTremL1 ECD(aa16-162)-Fc6mut

<400> SEQUENCE: 45
gaattcgcca ccatgcctct gctgctgctg ctgcctctgc tgtgggctgg cgcactggct    60
cagggcatag ttggcagcct ccctgaggtg ctgcaggcac ccgtgggaag ctccattctg    120

-continued

```
gtgcagtgcc actacaggct ccaggatgtc aaagctcaga aggtgtggtg ccggttcttg    180 ccggagggt gccagcccct ggtgtcctca gctgtggatc gcagagctcc agcgggcagg    240
cgtacgtttc tcacagacct gggtgggggc ctgctgcagg tggaaatggt taccctgcag    300
gaagaggatg ctggcgagta tggctgcatg gtggatgggg caggggggcc ccagattttg    360
cacagagtct ctctgaacat actgcccca gaggaagaag aagagaccca taagattggc     420
agtctggctg agaacgcatt ctcagaccct gcaggcagtg ccaacccttt ggaacccagc    480
caggatgaga agagcatccc cggtaccgag cccaaatctt ctgacaaaac tcacacatgc    540
ccaccgtgcc cagcacctga agccgagggg gcaccgtcag tcttcctctt ccccccaaaa    600
cccaaggaca cctcatgat ctcccggacc cctgaggtca catgcgtggt ggtggacgtg      660
agccacgaag accctgaggt caagttcaac tggtacgtgg acggcgtgga ggtgcataat    720
gccaagacaa agccgcggga ggagcagtac aacagcacgt accgtgtggt cagcgtcctc    780
accgtcctgc accaggactg gctgaatggc aaggagtaca gtgcaaggt ctccaacaaa     840 gccctcccat cctccatcga gaaaaccatc tccaaagcca aggcagcc ccgagaacca      900 caggtgtaca ccctgccccc atcccgggag gagatgacca gaaccaggt cagcctgacc     960 tgcctggtca aaggcttcta tcccagcgac atcgccgtgg agtgggagag caatgggcag   1020
ccggagaaca actacaagac cacgcctccc gtgctggact ccgacggctc cttcttcctc   1080
tatagcaagc tcaccgtgga caagagcagg tggcagcagg ggaacgtctt ctcatgctcc   1140
gtgatgcatg aggctctgca caaccactac acgcagaaga gcctctccct gtccccgggt   1200
aaatga                                                              1206
```

<210> SEQ ID NO 46
<211> LENGTH: 397
<212> TYPE: PRT
<213> ORGANISM: Artificial sequence
<220> FEATURE:
<223> OTHER INFORMATION: huCD33-huTremL1 ECD(aa16-162)-Fc6mut

<400> SEQUENCE: 46

```
Met Pro Leu Leu Leu Leu Pro Leu Leu Trp Ala Gly Ala Leu Ala
1               5                   10                  15

Gln Gly Ile Val Gly Ser Leu Pro Glu Val Leu Gln Ala Pro Val Gly
            20                  25                  30

Ser Ser Ile Leu Val Gln Cys His Tyr Arg Leu Gln Asp Val Lys Ala
        35                  40                  45

Gln Lys Val Trp Cys Arg Phe Leu Pro Glu Gly Cys Gln Pro Leu Val
    50                  55                  60

Ser Ser Ala Val Asp Arg Arg Ala Pro Ala Gly Arg Arg Thr Phe Leu
65                  70                  75                  80

Thr Asp Leu Gly Gly Gly Leu Leu Gln Val Glu Met Val Thr Leu Gln
                85                  90                  95

Glu Glu Asp Ala Gly Glu Tyr Gly Cys Met Val Asp Gly Ala Arg Gly
            100                 105                 110

Pro Gln Ile Leu His Arg Val Ser Leu Asn Ile Leu Pro Pro Glu Glu
        115                 120                 125

Glu Glu Glu Thr His Lys Ile Gly Ser Leu Ala Glu Asn Ala Phe Ser
    130                 135                 140

Asp Pro Ala Gly Ser Ala Asn Pro Leu Glu Pro Ser Gln Asp Glu Lys
145                 150                 155                 160
```

```
Ser Ile Pro Gly Thr Glu Pro Lys Ser Ser Asp Lys Thr His Thr Cys
            165                 170                 175

Pro Pro Cys Pro Ala Pro Glu Ala Glu Gly Ala Pro Ser Val Phe Leu
            180                 185                 190

Phe Pro Pro Lys Pro Lys Asp Thr Leu Met Ile Ser Arg Thr Pro Glu
            195                 200                 205

Val Thr Cys Val Val Val Asp Val Ser His Glu Asp Pro Glu Val Lys
        210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ser Ser Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly Lys
385                 390                 395

<210> SEQ ID NO 47
<211> LENGTH: 1515
<212> TYPE: DNA
<213> ORGANISM: Artificial sequence
<220> FEATURE:
<223> OTHER INFORMATION: huCD33-huTremL2 ECD(aa19-268)-Fc6mut

<400> SEQUENCE: 47
gaattcgcca ccatgcctct gctgctgctg ctgcctctgc tgtgggctgg cgcactggct      60
ggcccctctg ctgacagtgt atacacaaaa gtgaggctcc ttgaagggga gactctgtct     120
gtgcagtgct cctataaggg ctacaaaaac cgcgtggagg gcaaggtttg gtgcaaaatc     180
aggaagaaga agtgtgagcc tggctttgcc cgagtctggg tgaaagggcc cgctacttg      240 ctgcaggacg atgcccaggc caaggtggtc aacatcacca tggtggccct caagctccag     300
gactcaggcc gatactggtg catgcgcaac acctctggga tcctgtaccc cttgatgggc     360
ttccagctgg atgtgtctcc agctccccaa actgagagga cattcccttt cacacatctg     420
gacaacatcc tcaagagtgg aactgtcaca actggccaag cccctacctc aggccctgat     480
gcccctttta ccactggtgt gatggtgttc accccaggac tcatcacctt gcctaggctc     540
ttagcctcca ccagacctgc ctccaagaca ggctacagct tcactgctac cagcaccacc     600
agccagggac ccaggaggac catggggtcc cagacagtga ccgcgtctcc cagcaatgcc     660
agggactcct ctgctggccc cagaatccatc tccactaagt ctggggacct cagcaccaga     720
```

```
tcgcccacca cagggctctg cctcaccagc agatctctcc tcaacagact accctccatg    780
ccctccatca ggcaccagga tgtttactcc ggtaccgagc ccaaatcttc tgacaaaact    840
cacacatgcc caccgtgccc agcacctgaa gccgaggggg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccatc ctccatcgag aaaaccatct ccaaagccaa agggcagccc   1200
cgagaaccac aggtgtacac cctgccccca tcccgggagg agatgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct atagcaagct caccgtggac aagagcaggt ggcagcaggg gaacgtcttc   1440
tcatgctccg tgatgcatga ggctctgcac aaccactaca cgcagaagag cctctccctg   1500
tccccgggta aatga                                                   1515
```

<210> SEQ ID NO 48
<211> LENGTH: 500
<212> TYPE: PRT
<213> ORGANISM: Artificial sequence
<220> FEATURE:
<223> OTHER INFORMATION: huCD33-huTremL2 ECD(aa19-268)-Fc6mut

<400> SEQUENCE: 48

```
Met Pro Leu Leu Leu Leu Pro Leu Leu Trp Ala Gly Ala Leu Ala
1               5                   10                  15

Gly Pro Ser Ala Asp Ser Val Tyr Thr Lys Val Arg Leu Leu Glu Gly
            20                  25                  30

Glu Thr Leu Ser Val Gln Cys Ser Tyr Lys Gly Tyr Lys Asn Arg Val
        35                  40                  45

Glu Gly Lys Val Trp Cys Lys Ile Arg Lys Lys Lys Cys Glu Pro Gly
    50                  55                  60

Phe Ala Arg Val Trp Val Lys Gly Pro Arg Tyr Leu Leu Gln Asp Asp
65                  70                  75                  80

Ala Gln Ala Lys Val Val Asn Ile Thr Met Val Ala Leu Lys Leu Gln
                85                  90                  95

Asp Ser Gly Arg Tyr Trp Cys Met Arg Asn Thr Ser Gly Ile Leu Tyr
            100                 105                 110

Pro Leu Met Gly Phe Gln Leu Asp Val Ser Pro Ala Pro Gln Thr Glu
        115                 120                 125

Arg Asn Ile Pro Phe Thr His Leu Asp Asn Ile Leu Lys Ser Gly Thr
    130                 135                 140

Val Thr Thr Gly Gln Ala Pro Thr Ser Gly Pro Asp Ala Pro Phe Thr
145                 150                 155                 160

Thr Gly Val Met Val Phe Thr Pro Gly Leu Ile Thr Leu Pro Arg Leu
                165                 170                 175

Leu Ala Ser Thr Arg Pro Ala Ser Lys Thr Gly Tyr Ser Phe Thr Ala
            180                 185                 190

Thr Ser Thr Thr Ser Gln Gly Pro Arg Arg Thr Met Gly Ser Gln Thr
        195                 200                 205

Val Thr Ala Ser Pro Ser Asn Ala Arg Asp Ser Ser Ala Gly Pro Glu
    210                 215                 220
```

Ser Ile Ser Thr Lys Ser Gly Asp Leu Ser Thr Arg Ser Pro Thr Thr
225                 230                 235                 240

Gly Leu Cys Leu Thr Ser Arg Ser Leu Leu Asn Arg Leu Pro Ser Met
            245                 250                 255

Pro Ser Ile Arg His Gln Asp Val Tyr Ser Gly Thr Glu Pro Lys Ser
        260                 265                 270

Ser Asp Lys Thr His Thr Cys Pro Pro Cys Pro Ala Pro Glu Ala Glu
    275                 280                 285

Gly Ala Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ser Ser
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500

<210> SEQ ID NO 49
<211> LENGTH: 1233
<212> TYPE: DNA
<213> ORGANISM: Artificial sequence
<220> FEATURE:
<223> OTHER INFORMATION: huCD33-huTrem2 ECD(aa19-174)-Fc6mut

<400> SEQUENCE: 49
gaattcgcca ccatgcctct gctgctgctg ctgcctctgc tgtgggctgg cgcactggct      60
cacaacacca cagtgttcca gggcgtggcg ggccagtccc tgcaggtgtc ttgcccctat     120
gactccatga agcactgggg gaggcgcaag gcctggtgcc gccagctggg agagaagggc     180
ccatgccagc gtgtggtcag cacgcacaac ttgtggctgc tgtccttcct gaggaggtgg     240
aatgggagca cagccatcac agacgatacc ctgggtggca ctctcaccat tacgctgcgg     300
aatctacaac ccatgatgc gggtctctac cagtgccaga gcctccatgg cagtgaggct     360 gacacccctca ggaaggtcct ggtggaggtg ctggcagacc ccctgatca ccggatgct     420

```
ggagatctct ggttccccgg ggagtctgag agcttcgagg atgcccatgt ggagcacagc    480
atctccagga gcctcttgga aggagaaatc cccttcccac ccacttccgg taccgagccc    540
aaatcttctg acaaaactca cacatgccca ccgtgcccag cacctgaagc cgagggggca    600
ccgtcagtct tcctcttccc cccaaaaccc aaggacaccc tcatgatctc ccggacccct    660
gaggtcacat gcgtggtggt ggacgtgagc cacgaagacc ctgaggtcaa gttcaactgg    720
tacgtggacg gcgtggaggt gcataatgcc aagacaaagc cgcgggagga gcagtacaac    780
agcacgtacc gtgtggtcag cgtcctcacc gtcctgcacc aggactggct gaatggcaag    840
gagtacaagt gcaaggtctc caacaaagcc ctcccatcct ccatcgagaa aaccatctcc    900
aaagccaaag gcagccccga gaaccacagg tgtacaccc tgcccccatc ccgggaggag    960
atgaccaaga accaggtcag cctgacctgc ctggtcaaag gcttctatcc cagcgacatc   1020
gccgtggagt gggagagcaa tgggcagccg gagaacaact acaagaccac gcctcccgtg   1080
ctggactccg acggctcctt cttcctctat agcaagctca ccgtggacaa gagcaggtgg   1140
cagcagggga acgtcttctc atgctccgtg atgcatgagg ctctgcacaa ccactacacg   1200
cagaagagcc tctccctgtc cccgggtaaa tga                                1233
```

<210> SEQ ID NO 50
<211> LENGTH: 406
<212> TYPE: PRT
<213> ORGANISM: Artificial sequence
<220> FEATURE:
<223> OTHER INFORMATION: huCD33-huTrem2 ECD(aa19-174)-Fc6mut

<400> SEQUENCE: 50

```
Met Pro Leu Leu Leu Leu Pro Leu Leu Trp Ala Gly Ala Leu Ala
1               5                   10                  15

His Asn Thr Thr Val Phe Gln Gly Val Ala Gly Gln Ser Leu Gln Val
            20                  25                  30

Ser Cys Pro Tyr Asp Ser Met Lys His Trp Gly Arg Arg Lys Ala Trp
        35                  40                  45

Cys Arg Gln Leu Gly Glu Lys Gly Pro Cys Gln Arg Val Val Ser Thr
    50                  55                  60

His Asn Leu Trp Leu Leu Ser Phe Leu Arg Arg Trp Asn Gly Ser Thr
65                  70                  75                  80

Ala Ile Thr Asp Asp Thr Leu Gly Gly Thr Leu Thr Ile Thr Leu Arg
                85                  90                  95

Asn Leu Gln Pro His Asp Ala Gly Leu Tyr Gln Cys Gln Ser Leu His
            100                 105                 110

Gly Ser Glu Ala Asp Thr Leu Arg Lys Val Leu Val Glu Val Leu Ala
        115                 120                 125

Asp Pro Leu Asp His Arg Asp Ala Gly Asp Leu Trp Phe Pro Gly Glu
    130                 135                 140

Ser Glu Ser Phe Glu Asp Ala His Val Glu His Ser Ile Ser Arg Ser
145                 150                 155                 160

Leu Leu Glu Gly Glu Ile Pro Phe Pro Pro Thr Ser Gly Thr Glu Pro
                165                 170                 175

Lys Ser Ser Asp Lys Thr His Thr Cys Pro Pro Cys Pro Ala Pro Glu
            180                 185                 190

Ala Glu Gly Ala Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220
```

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
            245                 250                 255

Ser Thr Tyr Arg Val Val Ser Val Leu Thr Val Leu His Gln Asp Trp
        260                 265                 270

Leu Asn Gly Lys Glu Tyr Lys Cys Lys Val Ser Asn Lys Ala Leu Pro
    275                 280                 285

Ser Ser Ile Glu Lys Thr Ile Ser Lys Ala Lys Gly Gln Pro Arg Glu
290                 295                 300

Pro Gln Val Tyr Thr Leu Pro Pro Ser Arg Glu Glu Met Thr Lys Asn
305                 310                 315                 320

Gln Val Ser Leu Thr Cys Leu Val Lys Gly Phe Tyr Pro Ser Asp Ile
            325                 330                 335

Ala Val Glu Trp Glu Ser Asn Gly Gln Pro Glu Asn Asn Tyr Lys Thr
        340                 345                 350

Thr Pro Pro Val Leu Asp Ser Asp Gly Ser Phe Phe Leu Tyr Ser Lys
    355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys
            405

<210> SEQ ID NO 51
<211> LENGTH: 29
<212> TYPE: DNA
<213> ORGANISM: Artificial sequence
<220> FEATURE:
<223> OTHER INFORMATION: Primer

<400> SEQUENCE: 51
tagtagggat ccgctggtgc acaggaagg                                      29

<210> SEQ ID NO 52
<211> LENGTH: 32
<212> TYPE: DNA
<213> ORGANISM: Artificial sequence
<220> FEATURE:
<223> OTHER INFORMATION: Primer

<400> SEQUENCE: 52
tagtaggcgg ccgcttcgtg ggcctagggt ac                                  32

<210> SEQ ID NO 53
<211> LENGTH: 16
<212> TYPE: PRT
<213> ORGANISM: Homo sapiens

<400> SEQUENCE: 53

Met Pro Leu Leu Leu Leu Leu Pro Leu Leu Trp Ala Gly Ala Leu Ala
1               5                   10                  15

METHODS OF TREATING AUTOIMMUNE DISEASE OR CHRONIC INFLAMMATION WTIH ANTIBODIES THAT BIND PEPTIDOGLYCAN RECOGNITION PROTEIN 1

This application is a continuation of U.S. application Ser. No. 15/483,390, filed Apr. 10, 2017, now U.S. Pat. No. 10,150,809; which is a continuation of U.S. application Ser. No. 14/376,968, filed Aug. 6, 2014, now U.S. Pat. No. 9,663,568; which is a 371 of International Application PCT/EP2012/074093, filed Nov. 30, 2012; which claims benefit of U. S. Provisional Application 61/598,968, filed Feb. 15, 2012, EP 12158974.1, filed Mar. 12, 2012, and U.S. Provisional Application 61/672,799, filed Jul. 18, 2012. The contents of all above-named applications are incorporated herein by reference.

REFERENCE TO SEQUENCE LISTING SUBMITTED ELECTRONICALLY

The content of the electronically submitted sequence listing in ASCII text file (Name: 3338_0820005_ST25.txt; Size: 102,716 bytes; and Date of Creation: Oct. 23, 2018) is incorporated herein by reference in its entirety.

FIELD OF THE INVENTION

The present invention relates to the field of immunology. More particularly, the present invention relates to a method for the identification of the ligand that is able to stimulate Triggering Receptor Expressed on Myeloid cells (TREM-1), as well as antibodies that bind TREM-1's ligand. Such antibodies are capable of modulating myeloid cell activation and, therefore, inflammatory responses.

BACKGROUND

Peptidoglycan recognition protein 1 (otherwise known as PGLYRP1, PGRP-S, TNFSF3L, PGRP, TAG7 and PGRPS) is expressed in neutrophils and released upon their activation. PGLYRP1 is highly abundant in diseased tissue and has been shown to play an important role in the clearance of bacterial infections by the innate immune system. The family of PGLYRP proteins (PGLYRP1, PGLYRP2, PGLYRP3, PGLYRP4) all interact with bacterial peptidoglycans (PGNs) but there are important differences in the proteins' PGN binding sites. PGLYRP1 has an additional groove hypothesized to constitute a binding site for an unknown effector or signalling protein (J. Mol. Biol. 347: 683-691 (2005)). PGLYRP1 is a highly conserved, 196 amino acid long protein consisting of a signal peptide and a peptidoglycan binding domain.

The identification of a signalling mechanism mediated by PGLYRP1 is important in order to understand and thereby manipulate the function of this protein in various infectious and inflammatory diseases.

TREM-1, likewise, has well-described effects in immune modulation but, thus far, the mechanism leading to TREM-1 mediated immune function has not been understood. TREM-1 is a receptor expressed on myeloid cells, such as monocytes, macrophages and neutrophils. It is a transmembrane protein consisting of 234 amino acids, including a single extracellular immunoglobulin domain and a short cytoplasmic tail. TREM-1 has no apparent signalling motif but, when activated, forms dimers/multimers and mediates signalling by associating with the ITAM-containing signalling adaptor protein, DAP12. Downstream signalling may include phosphorylation of Syk and Zap70. Downstream signalling may include activation of the NFAT, ELK, NK-kappaB transcription factor. When TREM-1 is activated, it triggers the release of pro-inflammatory cytokines, such as TNF-α (TNF-alpha), IL-8 and monocyte chemotactic protein-1, from myeloid cells.

TREM-1 is upregulated in patients with sepsis, rheumatoid arthritis (RA) and inflammatory bowel disease (IBD) and increasing evidence supports the theory that TREM-1 contributes to the development and progression of inflammatory diseases. The blocking of TREM-1 signalling has furthermore been shown to have therapeutic activity in in vivo mouse models of RA and IBD.

The mode of action of TREM-1 activation has remained elusive because the ligand that activates TREM-1 is not known in the art. Therefore, there is a need in the art for a means of identifying TREM-1's ligand. There is a need in the art for a method of identifying a molecule, such as an antibody, that is capable of reducing, blocking, or interfering with the interaction of TREM-1 with its ligand. There is a need in the art for a molecule, such as an antibody, that is capable of binding TREM-1's ligand and thus reducing, blocking, or interfering with the stimulation of TREM-1 by its ligand. There is a need in the art for a molecule, such as an antibody, that is capable of binding TREM-1's ligand. There is a need in the art for a molecule, such as an antibody, that is capable of binding TREM-1's ligand and thus blocking TREM-1 activation and signalling. There is a need in the art for a molecule, such as an antibody, that is capable of binding TREM-1's ligand and thus reducing or blocking cytokine release from a myeloid cell expressing TREM-1.

Disclosed herein is a method and assay for identifying TREM-1's ligand and molecules, such as antibodies, that are capable of binding the ligand of TREM-1. Described herein are antibodies that are capable of influencing TREM-1 activation. Thus, the antibodies disclosed herein are suitable for use as pharmaceuticals. Antibodies that bind the ligand of TREM-1 and that reduce or block the interaction of TREM-1 with its ligand may have a substantial impact upon the quality of life of individuals with chronic inflammatory diseases such as rheumatoid arthritis, psoriatic arthritis and inflammatory bowel diseases.

SUMMARY

The invention relates to a method for identifying TREM-1's ligand and molecules, such as antibodies, that bind to TREM-1's ligand, herein identified as being PGLYRP1. The invention also relates to PGLYRP1 antibodies that may be identified by means of the invented method. Thus, the invention relates to PGLYRP1 antibodies that are capable of modifying the activation of TREM-1 by PGLYRP1, such as PGLYRP1 antibodies that are capable of reducing TREM-1 activity (signalling and/or activation) by PGLYRP1. Antibodies that reduce TREM-1 activity may be used for the treatment of inflammation.

The method for identifying a TREM-1 ligand comprises (a) culturing a cell expressing TREM-1, a signalling protein for TREM-1 and a reporter construct that is activated by said signalling protein; (b) detecting, preferably quantifying, the activity of said cell expressing TREM-1 when it is contacted with a cell, a compound or a fluid, such as a biological fluid or a tissue, that triggers TREM-1 activation; (c) contacting the culture of (b) with a TREM-1-activating component; (d) isolating the component that binds TREM-1 and (e) characterising the isolated component. The ligand for TREM-1, identified by means of the current invention as being PGLYRP1, may be used to modify the activity of TREM-1.

The method for identifying a molecule that specifically binds PGLYRP1 and that modifies TREM-1 mediated cellular activity, comprises: (a) culturing the cell according to any one of embodiments 1-18; (b) detecting, preferably quantifying, the activity of said cell expressing TREM-1 when it is contacted with PGLYRP1 and, optionally, a multimerisation agent such as PGN; (c) contacting the culture of (b) with a molecule that specifically binds PGLYRP1; and (d) detecting, preferably quantifying, that the activity of said cell expressing TREM-1 is less than or more than its activity as measured in (b).

The method for identifying a PGLYRP1 antibody that modifies TREM-1 mediated cellular activity comprises: (a) culturing a cell expressing TREM-1, a signalling protein for TREM-1 and a reporter construct that is activated by said signalling protein; (b) detecting, preferably quantifying, the activity of said cell expressing TREM-1 when it is contacted with PGLYRP1 and, optionally, in combination with a multimerising agent such as PGN; (c) contacting the culture of (b) with an antibody that binds PGLYRP1; and (d) detecting, preferably quantifying, that the activity of said cell expressing TREM-1 is less than or more than its activity as measured in (b).

One method of identifying a PGLYRP1 antibody that decreases TREM-1 mediated cellular activity comprises: (a) culturing a cell such as a T-cell expressing TREM-1, a signalling protein such as DAP12 and a reporter gene such as luciferase or beta-galactosidase; (b) incubating said cell with an activated neutrophil and, optionally, in combination with a multimerising agent such as PGN (c) detecting, preferably quantifying, the luminescence of said cell; (d) contacting the culture of the cell and the activated neutrophil with a PGLYRP1 antibody; and (e) detecting, preferably quantifying, that the luminescence of said cell is less than the activity measured in (c).

BRIEF DESCRIPTION OF THE DRAWINGS

FIGS. 2A-2D show the flow cytometric staining of PGN-stimulated neutrophils with a TREM-1-tetramer recombinant protein. Control protein does not bind (FIG. 2A), whereas a TREM-1-tetramer (SEQ ID NO: 2) binds to a subset of PGN-activated neutrophils (FIG. 2B), and this can be competed by another TREM-1 protein (FIG. 2D) but not by a control protein (FIG. 2C), confirming the specificity of the interaction.

FIGS. 6A-6G show that monoclonal anti-PGLYRP1 antibodies can block the TREM-1 response in the reporter assay stimulated with PGN-activated neutrophils. Examples of antibody hybridoma clone supernatants screened in various plates for their ability to block the activation signal. A few antibodies (those below the dotted line, such as F10, F95) are able to block this signal. Black dots represent isotype control in each plate (FIG. 6A). FIG. 6B shows testing from another fusion given rise to 2 additional blocking PGLYRP1 antibodies M-hPGRPS-2F5 and -2F7. Testing of commercially available anti-PGLYRP1 mAbs show that they are not able to block this signal even at high doses, whereas the polyclonal, commercially available PGLYRP1 pAb (AF2590, R&D Systems Minneapolis Minn., USA) can. FIG. 6C shows a comparison of the commercially available anti-PGLYRP1 mAb 1880424 from Thermo Scientific (Thermo Scientific, Waltham Mass., USA) with an isotype control (MAB002) and the polyclonal anti-PGLYRP1 pAb (AF2590). FIG. 6D shows a comparison of the commercially available anti-PGLYRP1 mAb 4H230 (US Biological, Salem Mass., USA) with an isotype control (MAB002) and the polyclonal anti-PGLYRP1 pAb (AF2590). FIG. 6E shows a comparison of the commercially available anti-PGLYRP1 mAb 9A319 (US Biological, Salem Mass., USA) with an isotype control (MAB002) and the polyclonal anti-PGLYRP1 pAb (AF2590), FIG. 6F shows a comparison of the commercially available anti-PGLYRP1 mAb 6D653 (Santa Cruz Biotechnology, Santa Cruz Calif., USA) with an isotype control (MAB002) and the polyclonal anti-PGLYRP1 pAb (AF2590). The slight decrease in activity seen for the SC 6D653 mAb appears to be due to the azide-containing formulation since a PGLYRP1 independent signal triggering TREM-1 with 1 µg/ml platebound anti-TREM-1 mAb shows the same phenomenon (FIG. 6G).

FIG. 7 shows that plate-bound agonistic anti-TREM-1 mAb (R&D MAB1278, Minneapolis, Minn., USA) stimulates TREM-1 (star) and that an RA synovial fluid (SF) sample to which PGN has been added displayed hTREM-1 ligand activity which can be neutralized by a PGLYRP1 polyclonal antibody (AF2590), indicating that TREM-1 activity is PGLYRP1 dependent.

BRIEF DESCRIPTION OF THE SEQUENCES

Figure 1:
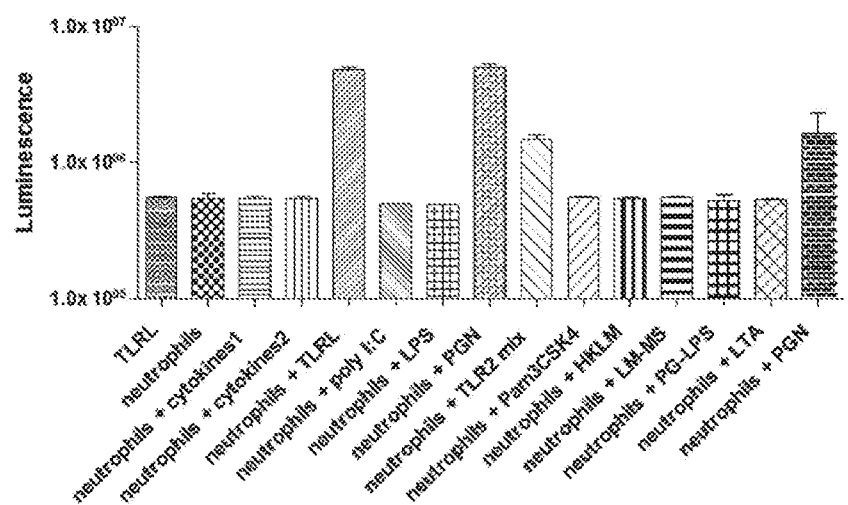
FIG. 1 shows that neutrophils activate the BWZ-TREM-1 reporter cell line. The BWZ reporter cell line expresses human TREM-1 and mediates activation of a NFAT-linked beta (β)-galactosidase reporter gene that may be quantitated by luminescence using the Beta-Glo Assay System kit from Promega, Denmark. The figure illustrates activation of the reporter cell line when cultured with neutrophils in the presence of either cytokine cocktails containing TNF-alpha (α), IL-6, IFN-gamma (γ) and GM-CSF or Toll-like Receptor (TLR) activating 'cocktails' (TLRL and TLR2 mix (tlrl-kit2hm, Invivogen, Sigma-Aldrich, Denmark), as well as in the presence of separate components of these activation mixtures.

SEQ ID NO: 1 represents the amino acid sequence of mature, full length hPGLYRP1 peptide sequence.

SEQ ID NO: 2 represents a recombinant protein sequence containing the following elements: human TREM-1 ECD, linker peptide, human TREM-1 ECD, human allotype IgG1 Fc with 7 mutations differing from wild type. (L15A, L16E, G18A, A111S, P112S, D137E, L139M) SEQ ID NO: 3 represents human allotype IgG1 Fc with 5 mutations differing from wild type: L15A, L16E, G18A, A111S, P112S.

SEQ ID NO: 4 represents a recombinant protein sequence containing the following elements from N to C terminus: 6xHIS tag, two copies of the streptavidin binding protein domain (SBP), GS linker, C terminus of cartilage oligomeric protein (COMP), GS linker, hDCIR-ECD.

SEQ ID NO: 5 represents a recombinant protein sequence containing the following elements: hTREM-1-ECD GS linker, C terminus of cartilage oligomeric protein (COMP), GS linker, two copies of the streptavidin binding protein domain (SBP), 6xHIS tag.

SEQ ID NO: 6 represents a recombinant protein sequence containing the following elements in order from N to C terminus, human CD83 ECD, G4Sx3 linker peptide, human CD83 ECD, human allotype IgG1 Fc mutant.

SEQ ID NO: 7 represents full length human PGLYRP1 coding cDNA sequence with C terminal GPI signal sequence. This sequence was cloned into pcDNA3.1zeo(+) (Invitrogen: V860-20, Carlsbad, Calif., USA) via EcoR1 and Xho1 restriction sites.

SEQ ID NO: 8 represents mature full length hTREM-1 ECD (aa. 21-200).

SEQ ID NO: 9 represents cDNA for a CD33 leader tandem hTREM extracellular domains separated by a G4Sx3 linker. A synthetic cDNA with a 5' EcoRI restriction site, a GCCACC Kozak sequence the CD33 leader sequence followed by the extracellular domain of human TREM-1 (aa17-200) with a interspaced KpnI restriction site and glycine-glycine-glycine-serine spacer repeated three times (G4Sx3) followed by an additional copy of the extracellular domain of human TREM-1 (aa17-200) and an Apa1 site to allow cloning.

SEQ ID NO: 10 represents pentameric hTREM-COMP-SBP38x2-6HIS. EcoR1 site and Kozak are 5' and BamH1 site is 3' of ORF.

SEQ ID NO: 11 represents hCD83 tetramer cloned into pJSV002-hFc6mut vector with EcoR1 and Apa1. EcoR1 site and Kozak are 5' and Apa1 site is 3' of ORF.

SEQ ID NO: 12 represents pentameric 6HIS-SBP38x2-COMP-hDCIR. EcoR1 site and Kozak 5' and BamH1 3' of ORF.

SEQ ID NO: 13 represents the nucleic acid sequence of the variable heavy chain of a monoclonal PGLYRP1 antibody (1F36, mAb 0182).

SEQ ID NO: 14 represents the nucleic acid sequence of the variable light chain of a monoclonal PGLYRP1 antibody (1F36, mAb 0182).

SEQ ID NO: 15 represents the amino acid sequence of the variable heavy chain of a monoclonal PGLYRP1 antibody (1F36, mAb 0182).

SEQ ID NO: 16 represents the amino acid sequence of the variable light chain of a monoclonal PGLYRP1 antibody (1 F36, mAb 0182).

SEQ ID NO: 17 represents the nucleic acid sequence of the variable heavy chain of a monoclonal PGLYRP1 antibody (1 F10).

SEQ ID NO: 18 represents the nucleic acid sequence of the variable light chain of a monoclonal PGLYRP1 antibody (1 F10).

SEQ ID NO: 19 represents the amino acid sequence of the variable heavy chain of a monoclonal PGLYRP1 antibody (1F10).

SEQ ID NO: 20 represents the amino acid sequence of the variable light chain of a monoclonal PGLYRP1 antibody (1F10).

SEQ ID NO: 21 represents the nucleic acid sequence of the variable heavy chain of a monoclonal PGLYRP1 antibody (1F105, mAb 0184).

SEQ ID NO: 22 represents the nucleic acid sequence of the variable light chain of a monoclonal PGLYRP1 antibody (1F105, mAb 0184).

SEQ ID NO: 23 represents the amino acid sequence of the variable heavy chain of a monoclonal PGLYRP1 antibody (1F105, mAb 0184).

SEQ ID NO: 24 represents the amino acid sequence of the variable light chain of a monoclonal PGLYRP1 antibody (1F105, mAb 0184).

SEQ ID NO: 25 represents the nucleic acid sequence of the variable heavy chain of a monoclonal PGLYRP1 antibody (1F95).

SEQ ID NO: 26 represents the nucleic acid sequence of the variable light chain of a monoclonal PGLYRP1 antibody (1F95).

SEQ ID NO: 27 represents the amino acid sequence of the variable heavy chain of a monoclonal PGLYRP1 antibody (1F95).

SEQ ID NO: 28 represents the amino acid sequence of the variable light chain of a monoclonal PGLYRP1 antibody (1F95).

SEQ ID NO: 29 represents the nucleic acid sequence of the variable heavy chain of a monoclonal PGLYRP1 antibody (2F5).

SEQ ID NO: 30 represents the nucleic acid sequence of the variable light chain of a monoclonal PGLYRP1 antibody (2F5).

SEQ ID NO: 31 represents the amino acid sequence of the variable heavy chain of a monoclonal PGLYRP1 antibody (2F5).

SEQ ID NO: 32 represents the amino acid sequence of the variable light chain of a monoclonal PGLYRP1 antibody (2F5).

SEQ ID NO: 33 represents the nucleic acid sequence of the variable heavy chain of a monoclonal PGLYRP1 antibody (2F7).

SEQ ID NO: 34 represents the nucleic acid sequence of the variable light chain of a monoclonal PGLYRP1 antibody (2F7).

SEQ ID NO: 35 represents the amino acid sequence of the variable heavy chain of a monoclonal PGLYRP1 antibody (2F7).

SEQ ID NO: 36 represents the amino acid sequence of the variable light chain of a monoclonal PGLYRP1 antibody (2F7).

SEQ ID NO: 37 represents the amino acid sequence of Type II 1.0 PGLYRP1.

SEQ ID NO: 38 represents the amino acid sequence of Type II 2.0 PGLYRP1.

SEQ ID NO: 39 represents the amino acid sequence of an epitope tag.

SEQ ID NO: 40 represents the amino acid sequence of full-length human PGLYRP2.

SEQ ID NO: 41 represents the amino acid sequence of full-length human PGLYRP3.

SEQ ID NO: 42 represents the amino acid sequence of full-length human PGLYRP4.

SEQ ID NO: 43 represents the nucleic acid sequence of hCD33-hTrem1 ECD(aa17-200)-Fc6mut.

SEQ ID NO: 44 represents the amino acid sequence of hCD33-hTrem1 ECD(aa17-200)-Fc6mut.

SEQ ID NO: 45 represents the nucleic acid sequence for hCD33-hTremL1 ECD(aa16-162)-Fc6mut.

SEQ ID NO: 46 represents the amino acid sequence of hCD33-hTremL1 ECD(aa16-162)-Fc6mut.

SEQ ID NO: 47 represents the nucleic acid sequence for hCD33-hTremL2 ECD(aa19-268)-Fc6mut.

SEQ ID NO: 48 represents the amino acid sequence of hCD33-hTremL2 ECD(aa19-268)-Fc6mut SEQ ID NO: 49 represents the nucleic acid sequence of hCD33-hTREM2-Fc6mut dimer SEQ ID NO: 50 represents the amino acid sequence of the hCD33-hTREM2-Fc6mut dimer.

SEQ ID NO: 51 represents the nucleic acid sequence of a primer.

SEQ ID NO: 52 represents the nucleic acid sequence of a primer.

SEQ ID NO: 53 represents the amino acid sequence of hCD33.

Description

The invention relates to a method for the identification of molecules such as antibodies that are capable of specifically binding TREM-1's signalling partner, herein identified as being PGLYRP1, and influencing PGLYRP1 binding with its signalling partner, TREM-1. PGLYRP1 may be used to modify the activity of TREM-1. Hence, the invention relates to molecules, such as antibodies, that influence inflammatory responses that are mediated by PGLYRP1. Antibodies that are capable of binding to PGLYRP1 and that influence TREM-1 activation and signalling have been created and identified.

A method or assay for the identification of TREM-1's ligand and for identification of molecules, such as antibodies, that are capable of specifically binding PGLYRP1 and reducing or blocking PGLYRP1 activation of TREM-1 may be created as follows:

A first cell or population of first cells is transfected with genes encoding TREM-1 or fragments thereof, a signalling protein and a reporter construct. The cell may be of haematopoietic origin, such as a myeloid cell, it may be a T-cell or it may be any other cell type that is capable of being transfected and expressing such molecules. The signalling protein may be any protein that is capable of transmitting or conveying a signal, either directly or indirectly, from TREM-1 to the reporter construct and may include DAP10, DAP12, TCR zeta, Fc gammaRIII, an Fc receptor, or any other protein that is capable of transmitting or conveying a signal from TREM-1 to the reporter construct. Alternatively, the signalling protein may be a TREM-1/signalling chimera molecule. The reporter construct comprises a transcription factor and a reporter gene, which in turn encodes a reporter protein that produces a detectable signal, such as a quantifiable signal. The transcription factor may be NFAT or NFkB or any other suitable transcription factor known in the art. The reporter gene may encode beta (β)-galactosidase, luciferase, green fluorescent protein (GFP), chloramphenicol transferase or any other reporter protein capable of producing a detectable signal. One suitable cell line that may be used for this bioassay is the BWZ.36/hTREM-1:DAP12:NFAT-LacZ T-cell (herein also identified as the "BWZ/hTREM-1 reporter cell"), the creation of which is described in detail in the examples. When activated, the BWZ/hTREM-1 reporter cell produces beta (3)-galactosidase, the production of which may be measured using equipment or kits known in the art, such as Beta Glow™ (Promega E4720, Madison, Wis., USA).

The first cell or population of first cells may be activated by incubation with PGLYRP1 and, optionally, a multimerisation agent. The optional multimerisation agent acts as a scaffold for PGLYRP1 and may be peptidoglycan (PGN), neutrophil extracellular traps (NETs), hyaluronic acid, a proteoglycan structure such as versican, aggrecan, decorin or fibrin, or any other naturally occurring matrix structure or molecule that is able to multimerise or present PGLYRP1. The first cell may be activated by incubation with one or more second cell(s) that expressPGLYRP1 on its/their surface, or intracellularly. An example of intracellular expression may be the storage of PGLYRP1 in secretory granules. The second cell may thus be any cell (or population of cells) that expresses or is transfected with a gene encoding PGLYRP1 and that expresses PGLYRP1 on its surface. Such a second cell may be a prokaryotic or a eukaryotic cell, such as a mammalian cell, such as a CHO cell, a BHK cell or a HEK cell. The second cell may also be an activated neutrophil. Neutrophils may be obtained from the whole blood or tissue of an individual and used either in bulk or as purified neutrophils. Any agent that mimics the bacterial activation of neutrophils, such as peptidoglycan (PGN) from the cell wall of a bacterium, such as PGN-SA, PGN-EB, PGN-EC, PGN-BS (InVivogen, tlrl-pgnsa, San Diego, Calif.), may be used to activate a neutrophil.

The activity of the first cell or population of first cells is then detected and, preferably, measured.

The culture of the first cell and the second cell(s) expressing PGLYRP1 and/or the culture of the first cell incubated with PGLYRP1 and, optionally, a multimerisation agent such as PGN, is contacted with an antibody that has been raised against PGLYRP1. The activity of the first cell or population of first cells is detected, and preferably measured.

In this way, antibodies that are capable of binding TREM-1's ligand, PGLYRP1, and that influence the interaction of PGLYRP1 with TREM-1 may be identified, PGLYRP1 antibodies that cause an increase in the activity of the first cell enhance the interaction of PGLYRP1 with TREM-1 and are herein identified as "stimulating PGLYRP1 antibodies". PGLYRP1 antibodies that cause a decrease in the activity of the first cell reduce, interfere, or block the interaction of PGLYRP1 with TREM-1 and are herein identified as "inhibitory PGLYRP1 antibodies". Inhibitory PGLYRP1 antibodies reduce or block TREM-1 activation and signalling.

Hence, the present invention relates to a method of characterising the function of PGLYRP1 antibodies. Antibodies capable of specifically binding PGLYRP1 and that have any effect upon TREM-1 activation and downstream signalling are herein referred to as "functional PGLYRP1 antibodies". Consequently, the term "functional PGLYRP1 antibodies" is intended to encompass both stimulating PGLYRP1 antibodies and inhibitory PGLYRP1 antibodies.

Furthermore, the present invention relates to antibodies that are capable of specifically binding PGLYRP1 and reducing, interfering with, or blocking its interaction with TREM-1, hence reducing TREM-1 activation and downstream signalling. Antibodies of the invention may have an immunoregulatory function, reducing the cytokine production of myeloid cells expressing TREM-1. For example, antibodies of the invention may reduce or prevent release of TNF-alpha (a), IL-1beta (b), IL-6, IFN-gamma (γ), MIP-1beta (b), MCP-1, IL-8 and/or GM-CSF from myeloid cells such as macrophages and/or neutrophils and/or myeloid cells in diseased tissue such as synovial tissue. Antibodies of the invention may be capable of down-regulating neutrophil responses.

PGLYRP1 antibodies according to the invention may reduce or block TREM-1 activation by means of one or a combination of several different mechanisms, affecting TREM-1 directly or indirectly. Antibodies of the invention may prevent PGLYRP1 from creating a functional complex with TREM-1.

Antibodies of the invention may block PGLYRP1 function by reducing or blocking TREM-1 activation and downstream signalling.

The present invention also relates to inhibitory PGLYRP1 antibodies that may be identified by other means than the method disclosed herein.

Antibodies of the invention may be capable of binding both human PGLYRP1 and PGLYRP1 from a species other than a human being. The term "PGLYRP1", as used herein, thus encompasses any naturally occurring form of PGLYRP1 which may be derived from any suitable organism, such as an invertebrate species or a vertebrate species. PGLYRP1 for use as described herein may be vertebrate PGLYRP1, such as mammalian PGLYRP1, such as PGLYRP1 from a primate (such as a human, a chimpanzee, a cynomolgus monkey or a rhesus monkey); a rodent (such as a mouse or a rat), a lagomorph (such as a rabbit), or an artiodactyl (such a cow, sheep, pig or camel), among others. Preferably, the PGLYRP1 is human PGLYRP1 (SEQ ID NO: 1). The PGLYRP1 may be a mature form of PGLYRP1 such as a PGLYRP1 protein that has undergone post-translational processing within a suitable cell. Such a mature PGLYRP1 protein may, for example, be glycosylated. The PGLYRP1 may be a full length PGLYRP1 protein. The PGLYRP1 may be a splice variant.

Antibodies of the invention may also be capable of specifically binding variants of PGLYRP1 such as SEQ ID NO: 37 (Type II 1.0 PGLYRP1) and/or SEQ ID NO: 38 (Type II 1.0 PGLYRP1).

Antibodies of the invention may be capable of influencing, such as inhibiting/reducing/blocking, the activity (signalling and/or activation) of both human TREM-1 and TREM-1 from another species than a human being. The term "TREM-1", as used herein, thus encompasses any naturally occurring form of TREM-1 which may be derived from any suitable organism. For example, TREM-1 for use as described herein may be vertebrate TREM-1, such as mammalian TREM-1, such as TREM-1 from a primate (such as a human, a chimpanzee, a cynomolgous monkey or a rhesus monkey); a rodent (such as a mouse or a rat), a lagomorph (such as a rabbit), or an artiodactyl (such a cow, sheep, pig or camel), among others. Preferably, the TREM-1 is human TREM-1. The TREM-1 may be a mature form of TREM-1 such as a TREM-1 protein that has undergone post-translational processing within a suitable cell. Such a mature TREM-1 protein may, for example, be glycosylated. The TREM-1 may be a full length TREM-1 protein. The TREM-1 may be a splice variant.

The term "antibody" herein refers to a protein, derived from a germline immunoglobulin sequence, which is capable of specifically binding to PGLYRP1 or a portion thereof. The term includes full length antibodies of any isotype (that is, IgA, IgE, IgG, IgM and/or IgY) and any single chain or fragment thereof. An antibody that specifically binds to PGLYRP1, or portion thereof, may bind exclusively to PGLYRP1, or portion thereof, or it may bind to a limited number of homologous antigens, or portions thereof.

Antibodies of the invention may be monoclonal antibodies, in the sense that they may be directly or indirectly derived from a single clone of a B lymphocyte. An antibody of the invention may be a monoclonal antibody, with the proviso that it is not 188C424 (Thermo Scientific), 4H230 or 9A319 (US Biological) or Clone 6D653 (Santa Cruz Biotechnology).

Antibodies of the current invention may be isolated. The term "isolated antibody" refers to an antibody that has been separated and/or recovered from another/other component(s) of its natural environment and/or purified from a mixture of components in its natural environment.

Antibodies may be recombinantly expressed in prokaryotic cells, eukaryotic cells or an acellular system derived from cellular extracts. The prokaryotic cell may be *E. coli*. The eukaryotic cell may be a yeast, insect or mammalian cell, such as a cell derived from an organism that is a primate (such as a human, a chimpanzee, a cynomolgus monkey or a rhesus monkey), a rodent (such as a mouse or a rat), a lagomorph (such as a rabbit) or an artiodactyl (such a cow, sheep, pig or camel). Suitable mammalian cell lines include, but are not limited to, HEK293 cells, CHO cells and HELA cells. PGLYRP1 antibodies may also be produced by means of other methods known to the person skilled in the art, such as a phage display or a yeast display. Antibodies of the invention may be raised in vivo by immunising a suitable mammal with PGLYRP1, a cell expressing PGLYRP1 or a combination of both.

PGLYRP1 antibodies may be produced, screened and purified using, for example, the methods described in the Examples. In brief, any suitable mouse, including a PGLYRP1 knock-out (KO) mouse or a TREM-1 KO mouse, may be immunised with PGLYRP1, a cell expressing PGLYRP1 or a combination of both. Primary screening of hybridoma supernatants may be performed using direct ELISA or FMAT and secondary screening may be performed using flow cytometry. Positive hybridoma supernatants, as well as purified antibodies, may then be screened for binding to, for example, full length PGLYRP1. Positive hybridoma supernatants or purified antibodies may then be tested for their ability to reduce or block PGLYRP1-stimulation of TREM-1-bearing cells. The method of the current invention may be used for this purpose.

Full-length antibodies of the invention may comprise at least four polypeptide chains: that is, two heavy (H) chains and two light (L) chains that are interconnected by disulfide bonds. One immunoglobulin sub-class of particular pharmaceutical interest is the IgG family, which may be subdivided into isotypes IgG1, IgG2, IgG3 and IgG4. IgG molecules are composed of two heavy chains, interlinked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a [binding] domain that is capable of interacting with an antigen (PGLYRP1), whilst the constant region of an antibody may mediate binding of the immunoglobulin to host tissues or factors, including but not limited to various cells of the immune system (effector cells), Fc receptors and the first component (Clq) of the classical complement system.

Examples of antigen-binding fragments include Fab, Fab', F(ab)$_2$, F(ab')$_2$, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10: 949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S: 1126-1136; WO2005040219, and published U.S. Patent Applications 20050238646 and 20020161201.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragments of an antibody that retain the ability to specifically bind to an antigen, such as human PGLYRP1 or PGLYRP1 from another species, as described herein. Examples of antigen-binding fragments include Fab, Fab', F(ab)$_2$, F(ab')$_2$, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

An antibody of the invention may be a human antibody or a humanised antibody. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains one or more sequences (CDR regions) derived from a non-human immunoglobulin. A humanised antibody is, thus, a human immunoglobulin (recipient antibody) in which at least residues from a hypervariable region of the recipient are replaced by residues from a hypervariable region of a non-human species (donor antibody) such as from a mouse, rat, rabbit, or non-human primate, which have the desired specificity, affinity, and capacity. In some instances, FR residues of the human immunoglobulin are replaced by corresponding non-human residues. An example of such a modification is the introduction of one or more so-called back-mutations.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant segments.

The fragment crystallisable region ("Fc region"/"Fc domain") of an antibody is the N-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. Preferably, a modified Fc domain comprises one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may further be modified to stabilise the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., MolImmunol. 199S; 30:105-8).

Antibodies or fragments thereof may also be defined in terms of their complementarity-determining regions (CDRs). The term "complementarity-determining region" or "hypervariable region", when used herein, refers to the regions of an antibody in which amino acid residues involved in antigen binding are situated. The CDRs are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may comprise a CDR region from one or more of the specific antibodies disclosed herein, such as a CDR region from within SEQ ID NOs: 15, 16, 19, 20, 23, 24, 27, 28, 31, 32, 35 or 36.

The 1F36 antibody has a heavy chain as shown in SEQ ID NO: 15 and a light chain as shown in SEQ ID NO: 16. An antibody of the invention may comprise this variable heavy chain sequence and/or this variable light chain sequence. The 1F36 antibody has the CDR sequences shown at amino acids 31 to 35, 50 to 66 and 98 to 108 of SEQ ID NO: 15 and amino acids 24 to 34, 51 to 56 and 89 to 97 of SEQ ID NO: 16. An antibody of the invention may comprise 1, 2, 3, 4, 5 or all 6 of these CDR sequences.

An antibody according to the invention may comprise: a CDRH1 sequence that corresponds to amino acid residues 31 to 35 (SWAM) of SEQ ID NO: 15, wherein one of these amino acid residues may be substituted by a different amino acid residue; and/or a CDRH2 sequence that corresponds to amino acids 50 to 66 (MIHPSDSETRLNQKFKD) of SEQ ID NO: 15, wherein one, two or three of these amino acids may be substituted by a different amino acid residue; and/or a CDRH3 sequence that corresponds to amino acid residues 98 to 108 (DYSDYDGFAY]) of SEQ ID NO: 15, wherein one, two or three of these amino acid residues may be substituted by a different amino acid.

An antibody according to the invention may comprise: a CDRL1 sequence that corresponds to amino acid residues 24 to 34 (RASQSISDYLH) of SEQ ID NO: 16, wherein one, two or three of these amino acid residues may be substituted with a different amino acid; and/or a CDRL2 sequence that corresponds to amino acid residues 51 to 56 (ASQSIS) of SEQ ID NO: 16, wherein one or two of these amino acid residues may be substituted with a different amino acid; and/or a CDRL3 sequence that corresponds to amino acid residues 89 to 97 (QNGHSFPLT) of SEQ ID NO: 16, wherein one or two of these amino acid residues may be substituted with a different amino acid.

The 1F10 antibody has a heavy chain as shown in SEQ ID NO: 19 and a light chain as shown in SEQ ID NO: 20. An antibody of the invention may comprise this variable heavy chain sequence and/or this variable light chain sequence. The 1F10 antibody has the CDR sequences shown at amino acids 31 to 35, 50 to 66 and 99 to 109 of SEQ ID NO: 19 and amino acids 24 to 33, 49 to 55 and 88 to 96 of SEQ ID NO: 20. An antibody of the invention may comprise 1, 2, 3, 4, 5 or all 6 of these CDR sequences.

An antibody according to the invention may comprise: a CDRH1 sequence that corresponds to amino acid residues 31 to 35 (DYNMY) of SEQ ID NO: 19, wherein one of these amino acid residues may be substituted by a different amino acid residue; and/or a CDRH2 sequence that corresponds to amino acids 50 to 66 (YIDPYNGDTSYNQKFKG) of SEQ ID NO: 19, wherein one, two or three of these amino acids may be substituted by a different amino acid residue; and/or a CDRH3 sequence that corresponds to amino acid residues 99 to 109 (GDYGNPFYLDY) of SEQ ID NO: 19, wherein one, two or three of these amino acid residues may be substituted by a different amino acid.

An antibody according to the invention may comprise a CDRL1 sequence that corresponds to amino acid residues 24 to 33 (SVSSSVNYMY) of SEQ ID NO: 20, wherein one, two or three of these amino acid residues may be substituted with a different amino acid; and/or a CDRL2 sequence that corresponds to amino acid residues 49 to 55 (DTSKLPS) of SEQ ID NO: 20, wherein one or two of these amino acid residues may be substituted with a different amino acid; and/or a CDRL3 sequence that corresponds to amino acid residues 88 to 96 (QQWTSNPPT) of SEQ ID NO: 20, wherein one or two of these amino acid residues may be substituted with a different amino acid.

The 1F105 antibody has a heavy chain as shown in SEQ ID NO: 23 and a light chain as shown in SEQ ID NO: 24. An antibody of the invention may comprise this variable heavy chain sequence and/or this variable light chain sequence. The 1F105 antibody has the CDR sequences shown at amino acids 31 to 35, 50 to 66 and 99 to 108 of SEQ ID NO: 23 and amino acids 24 to 33, 49 to 55 and 88 to 96 of SEQ ID NO: 24. An antibody of the invention may comprise 1, 2, 3, 4, 5 or all 6 of these CDR sequences.

An antibody according to the invention may comprise: a CDRH1 sequence that corresponds to amino acid residues 31 to 35 (DTYIH) of SEQ ID NO: 23, wherein one of these amino acid residues may be substituted by a different amino acid residue; and/or a CDRH2 sequence that corresponds to amino acids 50 to 66 (RIDPANDDTKYDPNFQG) of SEQ ID NO: 23, wherein one, two or three of these amino acids may be substituted by a different amino acid residue; and/or a CDRH3 sequence that corresponds to amino acid residues 99 to 108 (SDNSDSWFAY) of SEQ ID NO: 23, wherein one, two or three of these amino acid residues may be substituted by a different amino acid.

An antibody according to the invention may comprise: a CDRL1 sequence that corresponds to amino acid residues 24 to 33 (SVSSSVNFMN) of SEQ ID NO: 24, wherein one, two or three of these amino acid residues may be substituted with a different amino acid; and/or a CDRL2 sequence that corresponds to amino acid residues 49 to 55 (DTSKLAP) of SEQ ID NO: 24, wherein one or two of these amino acid residues may be substituted with a different amino acid; and/or a CDRL3 sequence that corresponds to amino acid residues 88 to 96 (HQWSSYSLT) of SEQ ID NO: 24, wherein one or two of these amino acid residues may be substituted with a different amino acid.

The 1F95 antibody has a heavy chain as shown in SEQ ID NO: 27 and a light chain as shown in SEQ ID NO: 28. An antibody of the invention may comprise this variable heavy chain sequence and/or this variable light chain sequence. The 1F95 antibody has the CDR sequences shown at amino acids 31 to 35, 50 to 66 and 99 to 106 of SEQ ID NO: 27 and amino acids 24 to 33, 49 to 54 and 87 to 95 of SEQ ID NO: 28. An antibody of the invention may comprise 1, 2, 3, 4, 5 or all 6 of these CDR sequences.

An antibody according to the invention may comprise: a CDRH1 sequence that corresponds to amino acid residues 31 to 35 (DYNMH) of SEQ ID NO: 27, wherein one of these amino acid residues may be substituted by a different amino acid residue; and/or a CDRH2 sequence that corresponds to amino acids 50 to 66 (YVDPYDGGTSSNQKFKG) of SEQ ID NO: 27, wherein one, two or three of these amino acids may be substituted by a different amino acid residue; and/or a CDRH3 sequence that corresponds to amino acid residues 99 to 106 (EVPYYFDY) of SEQ ID NO: 27, wherein one, two or three of these amino acid residues may be substituted by a different amino acid.

An antibody according to the invention may comprise: a CDRL1 sequence that corresponds to amino acid residues 24 to 33 (VASSSVTYMY) of SEQ ID NO: 28, wherein one, two or three of these amino acid residues may be substituted with a different amino acid; and/or a CDRL2 sequence that corresponds to amino acid residues 49 to 54 (THPLAS) of SEQ ID NO: 28, wherein one or two of these amino acid residues may be substituted with a different amino acid; and/or a CDRL3 sequence that corresponds to amino acid residues 87 to 95 (PHWNTNPPT) of SEQ ID NO: 28, wherein one or two of these amino acid residues may be substituted with a different amino acid.

The 2F5 antibody has a heavy chain as shown in SEQ ID NO: 31 and a light chain as shown in SEQ ID NO: 32. An antibody of the invention may comprise this variable heavy chain sequence and/or this variable light chain sequence. The 2F5 antibody has the CDR sequences shown at amino acids 31 to 35, 50 to 66 and 99 to 109 of SEQ ID NO: 31 and amino acids 24 to 33, 49 to 55 and 88 to 96 of SEQ ID NO: 32. An antibody of the invention may comprise 1, 2, 3, 4, 5 or all 6 of these CDR sequences.

An antibody according to the invention may comprise: a CDRH1 sequence that corresponds to amino acid residues 31 to 35 (DYYMY) of SEQ ID NO: 31, wherein one of these amino acid residues may be substituted by a different amino acid residue; and/or a CDRH2 sequence that corresponds to amino acids 50 to 66 (AISDDSTYTYYPDSVKG) of SEQ ID NO: 31, wherein one, two or three of these amino acids may be substituted by a different amino acid residue; and/or a CDRH3 sequence that corresponds to amino acid residues 99 to 109 (GGYGNLYAMDY) of SEQ ID NO: 31, wherein one, two or three of these amino acid residues may be substituted by a different amino acid.

An antibody according to the invention may comprise: a CDRL1 sequence that corresponds to amino acid residues 24 to 35 (TASSSVSSSYLH) of SEQ ID NO: 32, wherein one, two or three of these amino acid residues may be substituted with a different amino acid; and/or a CDRL2 sequence that corresponds to amino acid residues 51-57 (STSNLAS) of SEQ ID NO: 32, wherein one or two of these amino acid residues may be substituted with a different amino acid; and/or a CDRL3 sequence that corresponds to amino acid residues 90-98 (HQYHRSPFT) of SEQ ID NO: 32, wherein one or two of these amino acid residues may be substituted with a different amino acid.

The 2F7 antibody has a heavy chain as shown in SEQ ID NO: 35 and a light chain as shown in SEQ ID NO: 36. An antibody of the invention may comprise this variable heavy chain sequence and/or this variable light chain sequence. The 2F5 antibody has the CDR sequences shown at amino acids 31 to 35, 50 to 66 and 99 to 109 of SEQ ID NO: 35 and amino acids 24 to 34, 50 to 56 and 89 to 96 of SEQ ID NO: 36. An antibody of the invention may comprise 1, 2, 3, 4, 5 or all 6 of these CDR sequences.

An antibody according to the invention may comprise: a CDRH1 sequence that corresponds to amino acid residues 31 to 35 (NYVMH) of SEQ ID NO: 35, wherein one of these amino acid residues may be substituted by a different amino acid residue; and/or a CDRH2 sequence that corresponds to amino acids 50 to 66 (WINPFNDGTNYNENFKN) of SEQ ID NO: 35, wherein one, two or three of these amino acids may be substituted by a different amino acid residue; and/or a CDRH3 sequence that corresponds to amino acid residues 99 to 109 (SGFITTLIEDY) of SEQ ID NO: 35, wherein one, two or three of these amino acid residues may be substituted by a different amino acid.

An antibody according to the invention may comprise: a CDRL1 sequence that corresponds to amino acid residues 24 to 34 (KASESVGSFVS) of SEQ ID NO: 36, wherein one, two or three of these amino acid residues may be substituted with a different amino acid; and/or a CDRL2 sequence that corresponds to amino acid residues 50 to 56 (GASNRYT) of SEQ ID NO: 36, wherein one or two of these amino acid residues may be substituted with a different amino acid; and/or a CDRL3 sequence that corresponds to amino acid residues 89 to 96 (GQYYTHPT) of SEQ ID NO: 36, wherein one or two of these amino acid residues may be substituted with a different amino acid.

The term "antigen" (Ag) refers to the molecular entity used to immunise an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process, or other process, e.g. phage display, used for generating the Ab.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined using various criteria (e.g., a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term epitope herein comprises both types of binding region in any particular region of PGLYRP1 that specifically binds to a PGLYRP1 antibody. PGLYRP1 may comprise a number of different epitopes, which may include, without limitation, conformational epitopes which consist of one or more non-contiguous amino acids located near each other in the mature PGLYRP1 conformation and post-translational epitopes which consist, either in whole or part, of molecular structures covalently attached to PGLYRP1, such as carbohydrate groups. PGLYRP1 may also comprise linear epitopes.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criteria such as the distance between or solvent accessibility of atoms in the Ab:Ag complex. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as PGLYRP1 residues characterized by having a heavy atom (i.e. a non-hydrogen atom) within a distance of, eg., 2-6 Å, such as 3 Å, such as 4 Å, such as 5 Å from a heavy atom in the Ab.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g. determined from an X-ray structure, are said to be identical if they contain the same set of amino acid residues, Epitopes are said to overlap if at least one amino acid is shared by the epitopes. Epitopes are said to be separate (unique) if no amino acid residue are shared by the epitopes.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in PGLYRP1.

The epitope and paratope for a given antibody (Ab)/antigen (Ag) pair may be identified by routine methods. For example, the general location of an epitope may be determined by assessing the ability of an antibody to bind to different fragments or variant PGLYRP1 polypeptides. The specific amino acids within PGLYRP1 that make contact with an antibody (epitope) and the specific amino acids in an antibody that make contact with PGLYRP1 (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

An antibody according to the current invention may be capable of competing with 1F10 for binding to PGLYRP1. An antibody according to the current invention may be capable of competing with 1F36/mAb 0182 for binding to PGLYRP1. An antibody according to the current invention may be capable of competing with 1F95 for binding to PGLYRP1. An antibody according to the current invention may be capable of competing with 1F105/mAb 0184 for binding to PGLYRP1. An antibody according to the current invention may be capable of competing with 2F5 for binding to PGLYRP1. An antibody according to the current invention may be capable of competing with 2F7 for binding to PGLYRP1. Hence, an antibody according to the current invention may belong to the same bin as any one or more of these antibodies.

The term "binding affinity" herein refers to a measurement of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determining the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

A PGLYRP1 antibody of the invention may have a $K_D$ for its target (PGLYRP1) of $1\times10^{-6}$M or less, $1\times10^{-7}$M or less, $1\times10^{-8}$M or less, or $1\times10^{-9}$M or less, or $1\times10^{-10}$M or less, $1\times10^{-11}$M or less, $1\times10^{-12}$M or less or $1\times10^{-13}$M or less.

An antibody according to the current invention may be able to compete with another molecule, such as a naturally occurring ligand or receptor or another antibody, for binding to PGLYRP1. Therefore, an antibody according to the current invention may be able to bind PGLYRP1 with a greater affinity that that of another molecule also capable of binding PGLYRP1. The ability of an antibody to compete with a natural ligand/receptor for binding to an antigen may be assessed by determining and comparing the $K_D$ value for the interactions of interest, such as a specific interaction between an antibody and an antigen, with that of the $K_D$ value of an interaction not of interest.

The term "binding specificity" herein refers to the interaction of a molecule such as an antibody, or fragment thereof, with a single exclusive antigen, or with a limited number of highly homologous antigens (or epitopes). Antibodies that are capable of specifically binding to PGLYRP1 are not capable of binding dissimilar molecules. Antibodies according to the invention may not be able to bind PGLYRP family members such as PGLYRP2, PGLYRP3 and PGLYRP4. Antibodies according to the invention may not be able to bind human PGLYRP family members such as human PGLYRP2, human PGLYRP3 and human PGLYRP4.

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

In another aspect, the present invention provides compositions and formulations comprising molecules of the invention, such as the PGLYRP1 antibodies, polynucleotides, vectors and cells described herein. For example, the invention provides a pharmaceutical composition that comprises one or more PGLYRP1 antibodies of the invention, formulated together with a pharmaceutically acceptable carrier.

Accordingly, one object of the invention is to provide a pharmaceutical formulation comprising such a PGLYRP1 antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabiliser, or a surfactant, as well as various combinations thereof. The use of preservatives, isotonic agents, chelating agents, stabilisers and surfactants in pharmaceutical compositions is well-known to the skilled person. Reference may be made to Remington: The Science and Practice of Pharmacy, 19$^{th}$ edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

The PGLYRP1 antibodies of the present invention and pharmaceutical compositions comprising such antibodies may be used for the treatment of inflammatory diseases such as the following: inflammatory bowel disease (IBD), Crohns disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atoptic dermatitis, vitiligo, graft versus host disease, Sjogrens's syndrome, autoimmune nephritis, Goodpasture's syndrome, chronic inflammatory demyelinating polyneuropathy, allergy, asthma and other autoimmune diseases that are a result of either acute or chronic inflammation. The PGLYRP1 antibodies of the present invention and pharmaceutical compositions comprising such antibodies may be used for the treatment of cardiovascular disease, stroke, ischemic reperfusion injury, pneumonia, sepsis and cancer.

PGLYRP1 antibodies of the invention are suitable for use in the treatment of individuals with inflammatory bowel disease. Inflammatory Bowel Disease (IBD) is a disease that may affect any part of the gastrointestinal tract from mouth to anus, causing a wide variety of symptoms. IBD primarily causes abdominal pain, diarrhea (which may be bloody), vomiting, or weight loss, but may also cause complications outside of the gastrointestinal tract such as skin rashes, arthritis, inflammation of the eye, fatigue, and lack of concentration. Patients with IBD can be divided into two major classes, those with ulcerative colitis (UC) and those with Crohn's disease (CD). While CD generally involves the ileum and colon, it can affect any region of the intestine but is often discontinuous (focused areas of disease spread throughout the intestine), UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

PGLYRP1 antibodies of the invention are suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain amongst other physiologic effects. The involved joint can lose its shape and alignment, resulting in pain and loss of movement.

There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

PGLYRP1 antibodies of the invention are suitable for use in the treatment of individuals with psoriasis. Psoriasis is a T-cell mediated inflammatory disorder of the skin that can cause considerable discomfort. It is a disease for which there is currently no cure and affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., Internat. Immunopharmacol 2: 653-672, 2002), Efficacy in this model is a measured by reduction in skin pathology using a scoring system. Similarly, efficacy in patients is measured by a decrease in skin pathology.

PGLYRP1 antibodies of the invention are suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by joint swelling, similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said treatment is beneficial to the health of said human or other animal subject. The timing and purpose of said treatment may vary from one individual to another, according to many factors, such as the status quo of the subject's health. Thus, said treatment may be prophylactic, palliative, symptomatic and/or curative.

In terms of the present invention, prophylactic, palliative, symptomatic and/or curative treatments may represent separate aspects of the invention.

An antibody of the invention may be administered parenterally, such as intravenously, such as intramuscularly, such as subcutaneously. Alternatively, an antibody of the invention may be administered via a non-parenteral route, such as perorally or topically. An antibody of the invention Exemplary Embodiments 1. A cell expressing TREM-1, a signalling protein for TREM-1 and a reporter construct that is activated by said signalling protein.
2. The cell according to embodiment 1, wherein the cell is of haematopoetic origin.
3. The cell according to embodiment 2, wherein the cell is a myeloid cell.
4. The cell according to embodiment 2, wherein the cell is a T-cell.
5. The cell according to any one of embodiments 1-4, wherein the signalling protein is DAP10.
6. The cell according to any one of embodiments 1-4, wherein the signalling protein is DAP12.
7. The cell according to any one of embodiments 1-4, wherein the signalling protein is TCR zeta.
8. The cell according to any one of embodiments 1-4, wherein the signalling protein is Fc gamma RIII.
9. The cell according to any one of embodiments 1-4, wherein the signalling protein is a Fc receptor.
10. The cell according to any one of embodiments 1-9, wherein the reporter construct comprises a transcription factor and a reporter gene.
11. The cell according to embodiment 10, wherein said transcription factor is NFAT.
12. The cell according to embodiment 11, wherein said transcription factor is NFkB.
13. The cell according to any one of embodiments 10-12, wherein said reporter gene encodes β-galactosidase.
14. The cell according to any one of embodiments 10-12, wherein said reporter gene encodes luciferase.
15. The cell according to any one of embodiments 10-12, wherein said reporter gene encodes green fluorescent protein (GFP).
16. The cell according to any one of embodiments 10-12, wherein said reporter gene is a gene that encodes chloramphenicol transferase.
17. The cell according to any one of embodiments 1-4, 6, 10-11 and 13, which is a BWZ.36/hTREM-1:DAP12: NFAT-LacZ T-cell.
18. A method of stimulating the cell according to any one of embodiments 1-17, comprising contacting said cell with PGLYRP1.
19. A method of stimulating the cell according to any one of embodiments 1-17, comprising contacting said cell with PGLYRP1 and PGN.
20. The method according to any one of embodiments 18-19, wherein said PGLYRP1 is expressed by a cell.
21. The method according to embodiment 20, wherein the cell expressing PGLYRP1 is a prokaryotic cell.
22. The method according to embodiment 20, wherein the cell expressing PGLYRP1 is a eukaryotic cell.
23. The method according to embodiment 22, wherein the cell expressing PGLYRP1 is a mammalian cell.
24. The method according to embodiment 23, wherein the cell expressing PGLYRP1 is an activated neutrophil.
25. The method according to embodiment 23, wherein the cell expressing PGLYRP1 is a HEK cell.
26. A method of identifying a TREM-1 ligand, comprising; (a) culturing the cell according to any one of embodiments 1-18; (b) detecting, preferably quantifying, the activity of said cell expressing TREM-1 when it is contacted with a cell, a fluid such as a biological fluid or a tissue that triggers TREM-1 activation; (c) contacting the culture of (b) with a TREM-1 protein; (d) isolating the component that binds TREM-1 and (e) characterising the isolated component.
27. A method of identifying a molecule that specifically binds PGLYRP1 and that modifies TREM-1 mediated cellular activity, comprising: (a) culturing the cell according to any one of embodiments 1-18; (b) detecting, preferably quantifying, the activity of said cell expressing TREM-1 when it is contacted with PGLYRP1 and, optionally, a multimerisation agent such as PGN; (c) contacting the culture of (b) with a molecule that specifically binds PGLYRP1; and (d) detecting, preferably quantifying, that the activity of said cell expressing TREM-1 is less than or more than its activity as measured in (b).
28. A method of identifying a PGLYRP1 antibody, or fragment thereof, that modifies TREM-1 mediated cellular activity, comprising: (a) culturing the cell according to any one of embodiments 1-18; (b) detecting, preferably quantifying, the activity of said cell expressing TREM-1 when it is contacted with PGLYRP1 and, optionally, a multimerisation agent such as PGN; (c) contacting the culture of (b) with an antibody that binds PGLYRP1; and (d) detecting, preferably quantifying, that the activity of said cell expressing TREM-1 is less than or more than its activity as measured in (b).
29. The method according to embodiment 27, wherein said PGLYRP1 antibody, or fragment thereof, decreases TREM-1 mediated cellular activity and wherein the activity of the first cell when measured in (d) is less than its activity when measured in (b).
30. The method according to embodiment 27, wherein said PGLYRP1 antibody, or fragment thereof, increases TREM-1 mediated cellular activity and wherein the activity of the first cell when measured in (d) is more than its activity when measured in (b).
31. The PGLYRP1 antibody or fragment thereof that is identified by means of the method according to any one of embodiments 28-30,
32. A PGLYRP1 antibody or fragment thereof which is capable of specifically binding PGLYRP1 and reducing PGLYRP1-mediated TREM-1 activity.
33. The antibody, or fragment thereof, according to any one of embodiments 31-32, which is capable of reducing the release of one or more cytokines from cells that express TREM-1.
34. The antibody or fragment thereof according to any one of embodiments 31-33, which is a monoclonal antibody.
35. The antibody or fragment thereof according to any one of embodiments 31-34, which is a humanised antibody.
36. The antibody or fragment thereof according to any one of embodiments 31-34, which is a human antibody.
37. The antibody or fragment thereof according to any one of embodiments 31-34, which is a chimeric antibody.
38. The antibody according to any one of embodiments 31-37, wherein the isotype of said antibody is IgG.
39. The antibody according to embodiment 38, wherein said isotype is IgG1, IgG2 or IgG4.
40. The antibody according to embodiment 37, wherein the isotype of said antibody is IgG1.
41. The antibody according to embodiment 37, wherein the isotype of said antibody is IgG4.
42. The antibody or fragment thereof according to any one of embodiments 31-41, which is capable of competing with antibody 1F10 for binding to PGLYRP1.

43. The antibody or fragment thereof according to any one of embodiments 31-41, which is capable of competing with antibody 1F36/mAb 0182 for binding to PGLYRP1.

44. The antibody or fragment thereof according to any one of embodiments 31-41, which is capable of competing with antibody 1F95 for binding to PGLYRP1.

45. The antibody according to any one of embodiments 31-41, which is capable of competing with antibody 1F105/mAb 0184 for binding to PGLYRP1.

46. The antibody according to any one of embodiments 31-41, which is capable of competing with antibody 2F5 for binding to PGLYRP1.

47. The antibody according to any one of embodiments 31-41, which is capable of competing with antibody 2F7 for binding to PGLYRP1.

48. The antibody or fragment thereof according to any one of embodiments 31-47, which is capable of specifically binding SEQ ID NO: 37 (Type II 1.0 PGLYRP1) and/or SEQ ID NO: 38 (Type II 2.0 PGLYRP1).

49. The antibody or fragment thereof according to any one of embodiments 31-48, which has a $K_D$ for its target that is $1\times10^{-6}$M or less, $1\times10^{-7}$M or less, $1\times10^{-8}$M or less, or $1\times10^{-9}$M or less, or $1\times10^{-10}$M or less, $1\times10^{-11}$M or less, $1\times10^{-12}$M or less or $1\times10^{-13}$M or less, when determined using surface plasmon resonance.

50. The antibody according to any one of embodiments 31-49, the heavy chain of which comprises: a CDRH1 sequence corresponding to amino acid residues 31 to 35 (SYWMN) of SEQ ID NO: 15, wherein one of said amino acid residues may be substituted by a different amino acid residue; and/or a CDRH2 sequence corresponding to amino acids 50 to 66 (MIHPSDSETRLNQKFKD) of SEQ ID NO: 15, wherein one, two or three of said amino acids may be substituted by a different amino acid residue; and/or a CDRH3 sequence corresponding to amino acid residues 98 to 108 (DYSDYDGFAY]) of SEQ ID NO: 15, wherein one, two or three of said amino acid residues may be substituted by a different amino acid.

51. The antibody according to any one of embodiments 31-49, the heavy chain of which comprises: a CDRH1 sequence corresponding to amino acid residues 31 to 35 (DYNMY) of SEQ ID NO: 19, wherein one of said amino acid residues may be substituted by a different amino acid residue; and/or a CDRH2 sequence corresponding to amino acids 50 to 66 (YIDPYNGDTSYNQKFKG) of SEQ ID NO: 19, wherein one, two or three of said amino acids may be substituted by a different amino acid residue; and/or a CDRH3 sequence corresponding to amino acid residues 99 to 109 (GDYGNPFYLDY) of SEQ ID NO: 19, wherein one, two or three of said amino acid residues may be substituted by a different amino acid.

52. The antibody according to any one of embodiments 31-49, the heavy chain of which comprises: a CDRH1 sequence corresponding to amino acid residues 31 to 35 (DTYIH) of SEQ ID NO: 23, wherein one of said amino acid residues may be substituted by a different amino acid residue; and/or a CDRH2 sequence of amino acids 50 to 66 (RIDPANDDTKYDPNFQG) of SEQ ID NO: 23, wherein one, two or three of said amino acids may be substituted by a different amino acid residue; and/or a CDRH3 sequence of amino acid residues 99 to 108 (SDNSDSWFAY) of SEQ ID NO: 23, wherein one, two or three of said amino acid residues may be substituted by a different amino acid.

53. The antibody according to any one of embodiments 31-49, the heavy chain of which comprises: a CDRH1 sequence corresponding to amino acid residues 31 to 35 (DYNMH) of SEQ ID NO: 27, wherein one of said amino acid residues may be substituted by a different amino acid residue; and/or a CDRH2 sequence corresponding to amino acids 50 to 66 (YVDPYDGGTSSNQKFKG) of SEQ ID NO: 27, wherein one, two or three of said amino acids may be substituted by a different amino acid residue; and/or a CDRH3 sequence corresponding to amino acid residues 99 to 106 (EVPYYFDY) of SEQ ID NO: 27, wherein one, two or three of said amino acid residues may be substituted by a different amino acid.

54. The antibody according to any one of embodiments 31-49, the heavy chain of which comprises: a CDRH1 sequence that corresponds to amino acid residues 31 to 35 (DYYMY) of SEQ ID NO: 31, wherein one of these amino acid residues may be substituted by a different amino acid residue; and/or a CDRH2 sequence that corresponds to amino acids 50 to 66 (AISDDSTYTYYPDSVKG) of SEQ ID NO: 31, wherein one, two or three of these amino acids may be substituted by a different amino acid residue; and/or a CDRH3 sequence that corresponds to amino acid residues 99 to 109 (GGYGNLYAMDY) of SEQ ID NO: 31, wherein one, two or three of these amino acid residues may be substituted by a different amino acid.

55. The antibody according to any one of embodiments 31-49, the heavy chain of which comprises: a CDRH1 sequence that corresponds to amino acid residues 31 to 35 (NYVMH) of SEQ ID NO: 35, wherein one of these amino acid residues may be substituted by a different amino acid residue; and/or a CDRH2 sequence that corresponds to amino acids 50 to 66 (WINPFNDGTNYNENFKN) of SEQ ID NO: 35, wherein one, two or three of these amino acids may be substituted by a different amino acid residue; and/or a CDRH3 sequence that corresponds to amino acid residues 99 to 109 (SGFITTLIEDY) of SEQ ID NO: 35, wherein one, two or three of these amino acid residues may be substituted by a different amino acid.

56. The antibody according to any one of embodiments 50-55, the light chain of which comprises: a CDRL1 sequence corresponding to amino acid residues 24 to 34 (RASQSISDYLH) of SEQ ID NO: 16, wherein one, two or three of said amino acid residues may be substituted with a different amino acid; and/or a CDRL2 sequence corresponding to amino acid residues 51 to 56 (ASQSIS) of SEQ ID NO: 16, wherein one or two of said amino acid residues may be substituted with a different amino acid; and/or a CDRL3 sequence corresponding to amino acid residues 89 to 97 (QNGHSFPLT) of SEQ ID NO: 16, wherein one or two of said amino acid residues may be substituted with a different amino acid.

57. The antibody according to any one of embodiments 50-55, the light chain of which comprises: a CDRL1 sequence corresponding to amino acid residues 24 to 33 (SVSSSVNYMY) of SEQ ID NO: 20, wherein one, two or three of said amino acid residues may be substituted with a different amino acid; and/or a CDRL2 sequence corresponding to amino acid residues 49 to 55 (DTSKLPS) of SEQ ID NO: 20, wherein one or two of said amino acid residues may be substituted with a different amino acid; and/or a CDRL3 sequence corresponding to amino acid residues 88 to 96 (QQWTSNPPT) of SEQ ID NO: 20, wherein one or two of said amino acid residues may be substituted with a different amino acid.

58. The antibody according to any one of embodiments 50-55, the light chain of which comprises: a CDRL1 sequence corresponding to amino acid residues 24 to 33

(SVSSSVNFMN) of SEQ ID NO: 24, wherein one, two or three of said amino acid residues may be substituted with a different amino acid; and/or a CDRL2 sequence corresponding to amino acid residues 49 to 55 (DTSK-LAP) of SEQ ID NO: 24, wherein one or two of said amino acid residues may be substituted with a different amino acid; and/or a CDRL3 sequence corresponding to amino acid residues 88 to 96 (HQWSSYSLT) of SEQ ID NO: 24, wherein one or two of said amino acid residues may be substituted with a different amino acid.

59. The antibody according to any one of embodiments 50-55, the light chain of which comprises: a CDRL1 sequence corresponding to amino acid residues 24 to 33 (VASSSVTYMY) of SEQ ID NO: 28, wherein one, two or three of said amino acid residues may be substituted with a different amino acid; and/or a CDRL2 sequence corresponding to amino acid residues 49 to 54 (THPLAS) of SEQ ID NO: 28, wherein one or two of said amino acid residues may be substituted with a different amino acid; and/or a CDRL3 sequence corresponding to amino acid residues 87 to 95 (PHWNTNPPT) of SEQ ID NO: 28, wherein one or two of said amino acid residues may be substituted with a different amino acid.

60. The antibody according to any one of embodiments 50-55, the light chain of which comprises: a CDRL1 sequence that corresponds to amino acid residues 24 to 35 (TASSSVSSSYLH) of SEQ ID NO: 32, wherein one, two or three of these amino acid residues may be substituted with a different amino acid; and/or a CDRL2 sequence that corresponds to amino acid residues 51-57 (STSNLAS) of SEQ ID NO: 32, wherein one or two of these amino acid residues may be substituted with a different amino acid; and/or a CDRL3 sequence that corresponds to amino acid residues 90-98 (HQYHRSPFT) of SEQ ID NO: 32, wherein one or two of these amino acid residues may be substituted with a different amino acid.

61. The antibody according to any one of embodiments 50-55, the light chain of which comprises: a CDRL1 sequence that corresponds to amino acid residues 24 to 34 (KASESVGSFVS) of SEQ ID NO: 36, wherein one, two or three of these amino acid residues may be substituted with a different amino acid; and/or a CDRL2 sequence that corresponds to amino acid residues 50 to 56(GASNRYT) of SEQ ID NO: 36, wherein one or two of these amino acid residues may be substituted with a different amino acid; and/or a CDRL3 sequence that corresponds to amino acid residues 89 to 96 (GQYYTHPT) of SEQ ID NO: 36, wherein one or two of these amino acid residues may be substituted with a different amino acid.

62. The antibody according to any one of embodiments 31-61 for use as a medicament.

63. The antibody according to any one of embodiments 31-62 for use in the treatment of an inflammatory disease, 64. An antibody that is capable of specifically binding PGLYRP1 and reducing PGLYRP1-mediated TREM-1 activity for use as a medicament, 65. An antibody that is capable of specifically binding PGLYRP1 and reducing PGLYRP1-mediated TREM-1 activity for use in the treatment of an inflammatory disease.

66. Use according to embodiments 62-65, wherein the inflammatory disease is an autoimmune disease.

67. Use according to embodiment 66, wherein the autoimmune disease is rheumatoid arthritis (RA).

68. Use according to embodiment 66, wherein the autoimmune disease is inflammatory bowel disease (IBD) and/or ulcerative colitis.

69. Use according to embodiment 66, wherein the autoimmune disease is psoriatic arthritis (PA).

70. Use according to embodiment 62 or 64 in the treatment of cardiovascular disease, stroke, ischemia reperfusion injury, sepsis and/or cancer.

The present invention is further illustrated by the following examples which should not be construed as further limiting. The contents of all figures and all references, patents and published patent applications cited throughout this application are expressly incorporated herein by reference.

EXAMPLES

Example 1: Generation of a BWZ.36 humanTREM-1:DAP12 Stable Cell Line

The BWZ.36/hTREM-1:DAP12:NFAT-LacZ cell line (herein also referred to as the "BWZ/hTREM-1 reporter cell") was derived from BW5147 T cells (Mus musculus thymus lymphoma cell line, ATCC TIB-47, LGC Standards, Middelsex, UK) and contains a LacZ reporter construct regulated by four copies of the NFAT promoter element (see Karttunen, J. & Shastri, N. (1991) Proc. Natl. Acad. Sci. USA 88, 3972-3976 and Fiering, S., Northrop, J. P., Nolan, G. P., Matilla, P., Crabtree, G. R. & Herzenberg, L. A. (1990) Genes Dev. 4, 1823-1834). TREM/DAP12/pMX-IRES vector (encoding 786 bp of TREM-1 from a SmaI site to BamHI site using TREM-1 cDNA (Gene Bank Ref. ID: NM_018643.2, Sino Biological Inc., Beijing, China) as template and oligo 5' TAGTAGG-GATCCGCTGGTGCACAGGAAGG (SEQ ID NO: 51) and 5' TAGTAGGCGGCCGCTTCGTGGGCCTAGGGTAC (SEQ ID NO: 52) as primers cloned into pIREShyg vector GenBank Accession #U89672 (Cat. no. 6061-1, Clontech Laboratories, Calif., USA) was transfected in PLAT-E packaging cell line (provided by W. Yokoyama, Washington University; alternatively, Cat. no. RV-101, Cell Biolabs Inc, Bio-Mediator KY, Vantaa, Finland) using Superfect transfection reagent (Cat. no. 301305, Qiagen Nordic, Denmark), PLAT-E supernatants containing TREM/DAP12/pMX-IRES viral particles were used to infect BWZ.36 cells as follows: $2\times10^5$ BWZ.36 cells were cultured in 6 well plates and the medium was replaced with 1.5 ml of supernatant containing the viral particles +8 mg/ml of polybrene. After 6-8 hours, 1.5 ml of normal medium was added to the plate and the cells were incubated for an additional 24 hours. BWZ.36 cell lines stably expressing TREM-1 were stained with anti TREM-1 monoclonal antibody (clone 21C7; Bouchon et al, 2000, J. Immunol vol. 164 page 4991-4995) and isolated by cell sorting.

Example 2: Creation of a Bioassay for the Identification of Cells Expressing a Ligand for TREM-1

A TREM-1 reporter cell line was generated by transfecting the NFAT-lacZ bearing cell line BWZ.36 (Sanderson S, Int. Immun. 1994) with hTREM-1 and DAP12 as described in Example 1. This BWZ.36/hTREM-1:DAP12:NFAT-LacZ cell line (herein also referred to as a BWZ/hTREM-1 reporter cell) is highly responsive to antibody-mediated cross linking of TREM-1, giving ~40-fold induction of the NFAT-driven LacZ production when stimulated with 1-10

μg/ml plate bound commercially available anti-TREM-1 antibody, as compared to the isotype control. NFAT-driven LacZ production in the reporter cells may be assayed using a luminescence based kit, Beta Glow™ (Promega E4720, Madison, Wis.). Plates were coated with isotype control or aTREM-1 MAB1278 (Conc 3 ug/ml in PBS, 100 ul/well) (R&D Systems, Minneapolis, USA) at 4 C for 16 hours or for 2 hr at 37° C., 5% CO2 and the BWZ/hTREM-1 reporter cells were detached by adding 10 ml Versene (catalog number #15040, Gibco, Carlsbad Calif., USA), spun at 400 g for 5 min and washed in PBS and media (RPMI-1640 w/o phenol red; cat. number 11835, Gibco, Carlsbad Calif., USA) before adding to the coated plates ($1\times10^6$ cells/ml, $4\times10^4$ cells/well) to total volume 100 ul and incubated overnight (16-20 hours) at 37° C., 5% $CO_2$.

These TREM-1 responsive cells were used to identify cells expressing TREM-1 ligand. One such cell turned out to be neutrophils from the whole blood. The neutrophils of healthy donors were purified by means of Ficoll and dextran sedimentation and stimulated with PGN (InVivogen, tlrl-pgnsa, San Diego, Calif., USA) overnight. Briefly, the BWZ/hTREM-1 reporter cells were added to the activated neutrophil cultures in a 1:3 ratio of reporter cell:neutrophils. The assay was run in Poly-D-Lysine coated Black cell culture plates (#356640 from BD Biosciences, San Jose, Calif., USA). TREM-1 activation was read out after 24 hours of culture using the BetaGlo reagent (E4720 from Promega, Madison, Wis., USA) and luminescence measured using a TopCount Luminescence counter from Perkin Elmer.

The vitro stimulated neutrophils possessed a ligand that was able to induce TREM-1 signalling, and neutrophils from the whole blood of healthy donors were purified by Dextran sedimentation and stimulated overnight with multiple reagents. The only reagent that was able to stimulate a TREM-1 responsive signal from neutrophils was PGN-SA (Invivogen, tlrl-pgnsa, San Diego, Calif., USA) which mimic bacterial activation of the cells. These activated neutrophils were then used to stimulate the BWZ/hTREM-1 reporter cell line, by co-culturing the cells. Briefly, the BWZ/hTREM-1 reporter cells were added to the activated neutrophil cultures in a 1:3 ratio of reporter cell:neutrophils. The assay was run in Poly-D-Lysine coated black cell culture plates (cat. no. 356640 BD Biosciences, San Jose, Calif., USA), TREM-1 activation was read out after 24 hours of culture using the BetaGlo reagent (cat. no. E4720, Promega, Madison, Wis., USA) and luminescence measured using a TopCount Luminescence counter from (Perkin Elmer, Waltham Mass., USA). As shown in FIG. 1, significant induction of reporter activity was observed in BWZ/hTREM-1 cells co-cultured with the PGN-stimulated neutrophils. This induction was highly dependent on neutrophil activation. No response was seen with resting neutrophils (bar 2 neutrophils). Likewise, no response was seen when stimulating BWZ/hTREM-1 reporter cells with PGN-SA in the TLRL cocktail in the absence of neutrophils (bar 1-TLRL), demonstrating that the response is not merely a direct effect of PGN on the BWZ/hTREM-1 cells. Activating neutrophils with cytokine cocktails (bar 3+4 neutrophils+cytokines) did not provide the correct TREM-1 activation signal either.

Example 3: Binding of Soluble TREM-1 to PGN-Activated Neutrophils

PGN-stimulated neutrophils were able to induce TREM-1 activation, indicating the presence of a TREM-1 stimulating factor in the PGN-stimulated neutrophil cultures. In order to confirm the presence of a TREM-1-interacting protein on the neutrophils, PGN-stimulated neutrophils were stained with a recombinant TREM-1-tetrameric protein and analysed by flow cytometry. Briefly, granulocytes were isolated from human whole blood obtained from Astarte Biologics (Redmond, Wash., USA) via a Ficoll-dextran sedimentation method. Blood was stratified on FicollPaque (17-0840-03, GE Healthcare, Piscataway, N.J., USA) gradient with a ratio of 3 parts of Ficoll and 4 parts of blood in a 50ml tube, then centrifuged at 400×g for 30 minutes at 22° C., without brake. The intermediate PBMC band was gently removed by aspiration. The granulocytes stratified on the packed RBC were aspirated and transferred to a 50 ml polypropylene tube. The granulocytes and contaminating RBCs were diluted to 40 ml with 1x PBS and followed by addition of 10 ml 4% DEXTRAN 500 (Sigma, 31392, St Louis, Mo., USA) in PBS solution. After mixing by gentle inversion, the tubes were left at 22° C. for 20-30 min. A granulocyte rich supernatant was then transferred into a fresh tube and centrifuged at 250×g, 5 min, 22° C.; the supernatant was aspirated and discarded. Contaminating RBCs were removed with an osmotic lysis, briefly, the cell pellet was resuspended in 7.5 ml of 0.2% NaCl; gently mixed for 55-60 seconds and 17.5 ml of a 1.2% NaCl. solution was added. The volume was then brought to 50 ml with PBS and spun at 250×g for 5 min, the pellet was resuspended in 7.5 ml of 0.2% NaCl to repeat the lysis a second time. The final granulocyte pellet was resuspended in RPMI/10% FBS.

Isolated granulocytes were cultured at a density of 3.8 E6/ml in RPMI/10% FBS+10 μg/ml of PGN-SA (InvivogentIrl-pgnsa, San Diego, Calif., USA) for 7 days. Cells were pelleted by centrifugation and resuspended in PBS/2% FBS for staining. Resuspended granulocytes were then plated in a 96 well plate (round bottom) at a density of 100,000/well in the presence or absence of 2 μg/ml of probe, with or without 100 μg/ml (50×) of a specific or irrelevant competitor protein. Cells were incubated with probe/competitor for 1 hour at 4 C in a volume of 50 μl/well. At the end of the incubation, 150 μl/well of PBS/2% FBS was added and the cells were pelleted. The pelleted cells were resuspended in 50 μl/well of goat anti hFc F(ab')2/PE conjugate (Jackson ImmunoResearch 109-116-098, West Grove, Pa., USA) and incubated at 4° C. for 30 minutes. 150 μl/well of PBS/2% FBS was added and the cells pelleted. Pelleted cells were further washed in 200 μl/well PBS/2% FBS and pelleted. Washed cells were then resuspended in 100 μl/well of fixative (1:1 PBS: Cytofix. 554655, BD Biosciences, San Jose, Calif., USA) and incubated 5 minutes at room temperature, 100 μl/well of PBS/2% FBS was added to fixed cells, then the cells were pelleted. The stained/fixed cells were then resuspended in 100 μl/well of PBS/2% FBS for flow cytometric analysis on a LSR II flow cytometer. (BD Biosciences, San Jose, Calif., USA).

Probe Set:

| Fc mut | 5.36 mg/ml | SEQ ID NO: 3 |
|---|---|---|
| hTREM-1 tet/Fc mut | 1.07 mg/ml | SEQ ID NO: 2 |

Competitors for hTREM-1 tet/Fc Mut:

| 50X DCIR COMP | 0.3 mg/ml | SEQ ID NO: 4 |
|---|---|---|
| 50X TREM COMP | 1.14 mg/ml | SEQ ID NO: 5 |

Figure 2A:
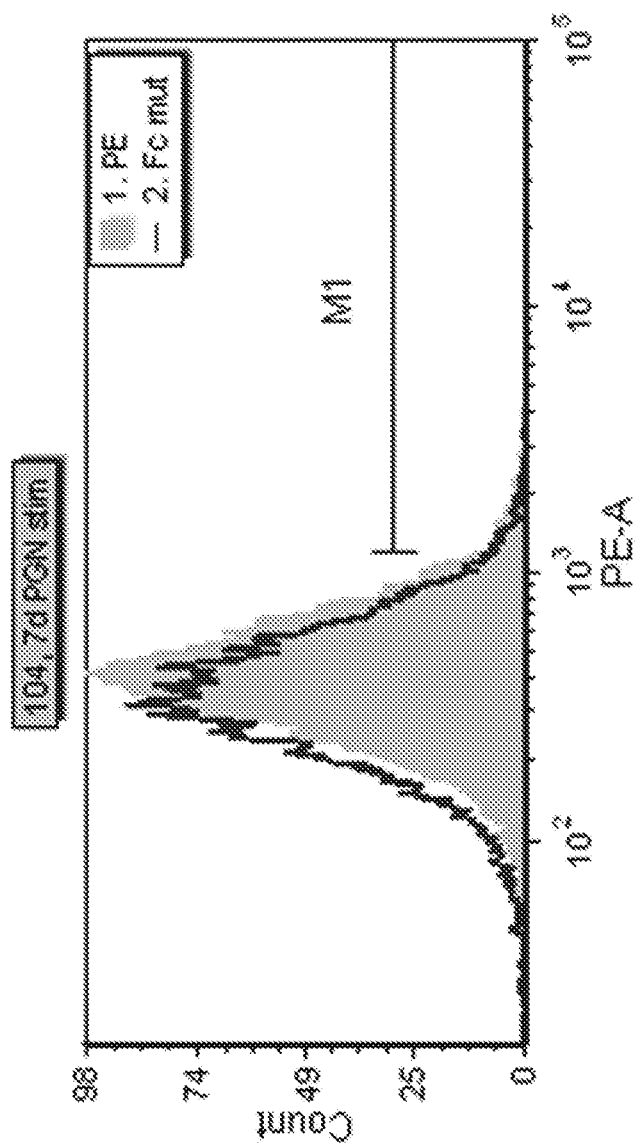
Figure 2B:
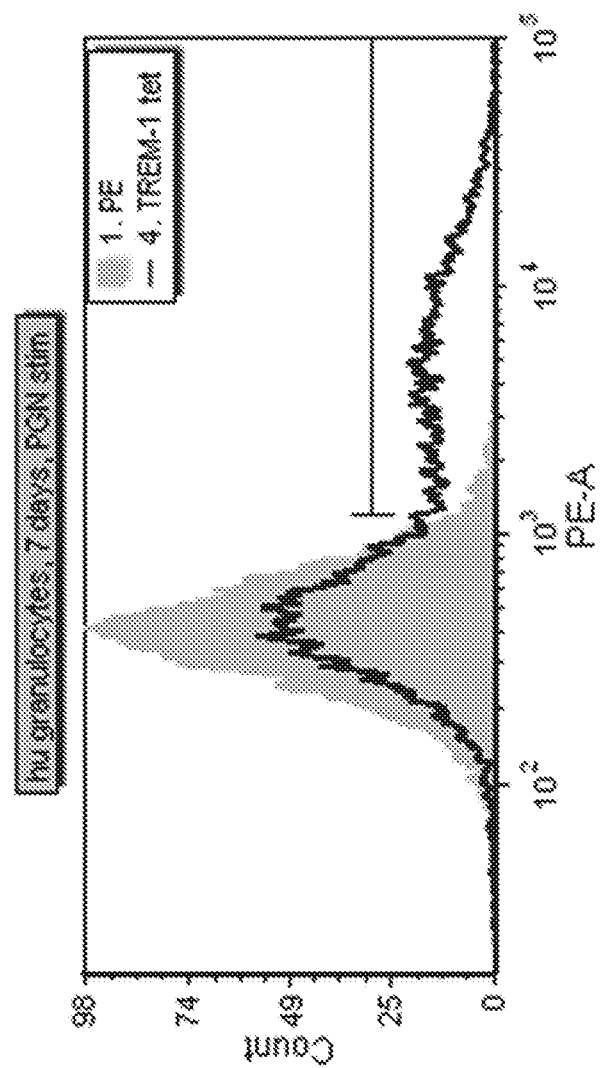
Figure 2D:
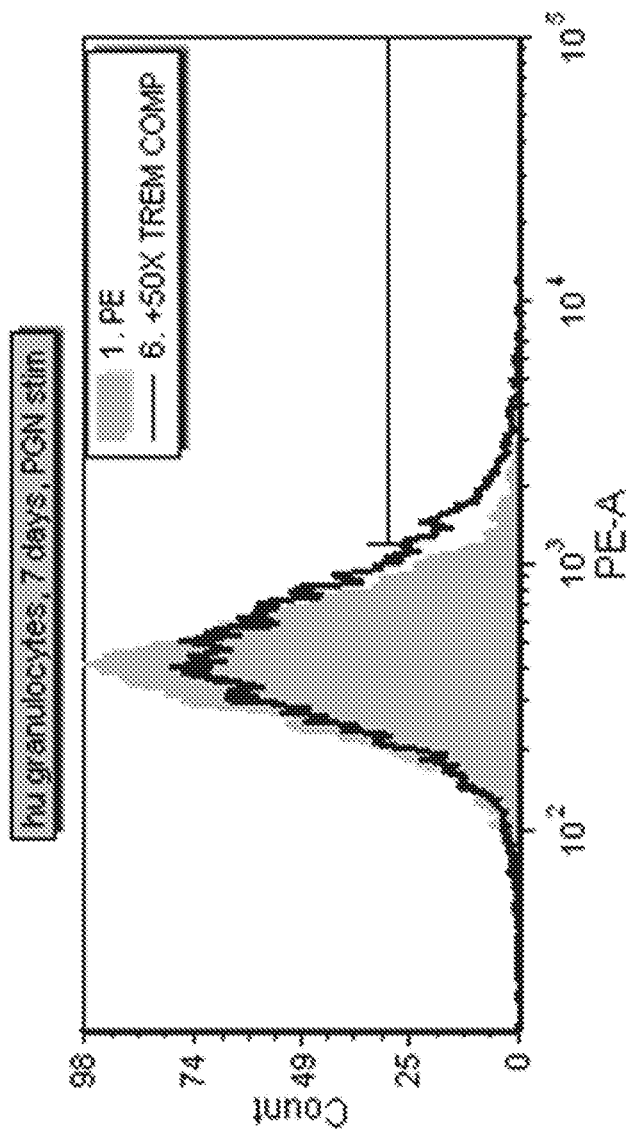

Histograms were created from the flow cytometric data. The background fluorescence from the goat anti hFc/PE conjugate was shown in each histogram as the background and was designated "PE". An identical marker was drawn on each histogram to designate the percentage of cells that bound to the secondary goat anti hFc/PE conjugated antibody. The negative control Fc mut protein showed 2% positive binding cells, which was identical to the background fluorescence seen with the goat anti hFc/PE conjugate alone (FIG. 2A). When cells were stained with 2 µg/ml hTREM-1/tetramer they were 39% positive (FIG. 2B). Men the TREM-1 tetramer binding was done in the context of 100 µg/ml DCIR COMP protein, the cells were 41% positive confirming that the DCIR COMP did not compete for binding with TREM-1 tetramer (FIG. 2C). When the TREM-1 tetramer binding was done in the presence of 100 µg/ml of TREM-1 COMP, the cells were 10% positive showing that the TREM COMP protein did compete with TREM-1 tetramer for binding to the cells (FIG. 2D).

Example 4: Identification of PGLYRP1 as a Neutrophil-Expressed TREM-1 Ligand

Figures 3A, 3B:
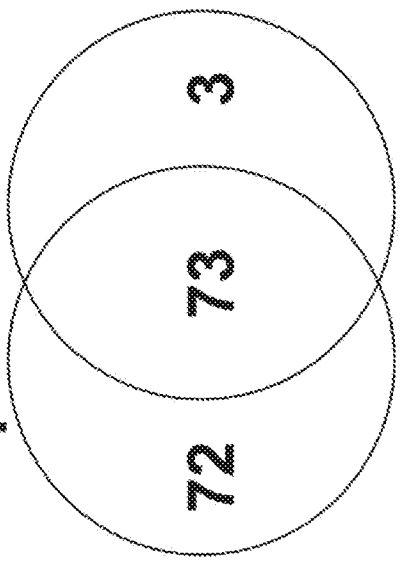
FIG. 3A and FIG. 3B: PGLYRP1 is identified by Immunoprecipitation (IP)/Mass spectroscopy (MS) with TREM-1. Soluble TREM-Fc was incubated with PGN-activated neutrophils, crosslinked, immunoprecipitated followed by cleanup, trypsin digestion and mass spectroscopy. The immunoprecipitation of the TREM-1 binding proteins resulted in 3 specific proteins, 73 proteins overlap with the control protein, and 72 were precipitated by the control protein alone (background (FIG. 3A)). The table (FIG. 3B) shows the results from the TREM-1 specific immunoprecipitation and subsequent mass spectroscopy.

PGLYRP1 was identified as a TREM-1 ligand through the use of immunoprecipitation coupled with mass spectroscopy (IP-MS). Soluble TREM-1 tetramer was used as an affinity "bait" molecule to identify a ligand. Briefly, TREM-1-tetramer-Fc (SEQ ID NO: 2) and separately CD83-Fc (SEQ ID NO: 5) were each incubated at final concentrations of 100 µg/ml with 270 million human neutrophils, purified by dextran sedimentation as described above, in 1 mL PBS at 4° C., 90 minutes with mild shaking. After pelleting, the cells were resuspended in 1 mL PBS buffer with the inclusion of the crosslinker 3,3'-Dithiobis[sulfosuccinimidylpropionate] (DTSSP) (Thermo Scientific: 21578, Rockford, Ill., USA), at a concentration of 2 mM and incubated 30 minutes at room temperature. Cells were washed 3× with 1 mL PBS followed by lysis in 1 mL RIPA buffer (Thermo Scientific, 89901, Rockford, Ill., USA). The lysate was centrifuged at 15,000×g for 10 minutes at 4° C. to remove insoluble materials. Neutrophil proteins cross-linked to Fc coupled probes were immunoprecipitated from the supernatant using Protein A Mag Sepharose™ beads (GE Healthcare Life Sciences, 28-9670-56, Piscataway, N.J., USA). Briefly, 50 µL of beads were first washed with 200 µL PBS, then resuspended in 1 mL of cell lysate, incubated 60 minutes at 4° C., magnetically captured, and sequentially washed 2× with 200 µl RIPA buffer then 3× with 200 µL PBS. Upon removing PBS from the final magnetic capture, proteins were eluted from the magnetic beads using 200 µL buffer containing 8 M Urea, 100 mM Tris (pH 8.0), and 15 mM TCEP (Thermo Scientific, 77720, Rockford, Ill., USA) and incubated at room temperature for 30 minutes, beads were captured and supernatant was transferred to a Microcon Ultracel YM-30 filter (Millipore, 42410, Billerica, Mass., USA). Samples were spun at 14,000×g, 20° C., 30-60 minutes until no liquid remained on the top of the filter membrane. The retained proteins were then alkylated with 100 µL 50 mM IAA (iodoacetamide) in 8 M Urea for 30 minutes in dark at room temperature. The filter was washed 2× with 100 µL 50 mM NH$_4$HCO$_3$ and then transferred to a new collection tube. 1 µg trypsin (cat. no. V5111, Promega, Madison Wis., USA) in 60 µL 50 mM NH$_4$HCO$_3$ was added followed by incubation at 37° C. overnight. The tryptic digest was collected by centrifugation at 14,000×g for 30 minutes followed by washing the filter with 50 µL 50 mM NH$_4$HCO$_3$. 10 µL of the digest was analyzed by LC/MS/MS using an LTQ-Orbitrap-XL mass spectrometer (Thermo Scientific, Waltham, Mass., USA). The data was searched against IPI human database (v3.81) using SEQUEST-Sorcerer engine (4.0.4 build) (SageN, Milpitas, Calif., USA) and then post processed with Scaffold 3 (Proteome Software, Portland, Oreg., USA) to filter protein IDs with a false discovery rate of 1%. After negative control subtraction, PGLYRP1 was found to be a high-confidence protein specifically associated with hTREM-1 tetramer. The immunoprecipitation in the neutrophils showed that out of the 148 identified proteins, 72 proteins were immunoprecipitated by the control construct (CD83) alone, 73 of the proteins were identical for TREM-1 and CD83, whereas only three were TREM-1 specific (FIG. 3A and FIG. 3B). The experiment was subsequently repeated using neutrophils from a different donor and PGLYRP1 was again identified as specifically interacting with hTREM-1.

Example 5: Purification of Human PGLYRP1 Expressed from HEK293 6E

A recombinant protein sequence was constructed by fusing the human CD33 signal peptide sequence (SEQ ID NO: 53) with the human mature PGLYRP1 coding sequence (SEQ ID NO: 1). The resulting open reading frame was cloned into pcDNA3.1/Zeo(+) vector (Life Technologies, Carlsbad Calif., USA) after a CMV promoter. The pcDNA3.1-hPGLYRP1 construct was then transfected into HEK293 6E cells with 293fectin™ (Life Technologies, Carlsbad Calif., USA) following the vendor's protocol. 5 days after transfection, the culture supernatant containing secreted human PGLYRP1 was harvested by centrifugation (15,000 rpm×20 min, 4□C) and then cleared by the filtration with 0.22 µm cellulose nitrate membrane. The cleared supernatant was first diluted 10 fold into 20 mM sodium citrate pH 5.0 and then applied to a Hitrap SP HP 5 ml column (17-1151-01 GE Healthcare, Uppsala, Sweden), followed by a 5 column volume wash with 20 mM sodium citrate pH5.0. The bound human PGLYRP1 was then eluted with a 0~100% linear gradient of 20 mM sodium citrate pH 5.0, 1M NaCl in 30 column volumes. The fractions containing dimer and monomer forms of human PGLYRP1 were pooled separately and concentrated to less than 4 ml by Amicon ultra 15 centrifugal units (UFC800324 3,000 kDa MWCO, Millipore, Hellerup, Denmark). Dimer and monomer pools were further polished and buffer-exchanged to Phosphate Buffered Saline (PBS) by a Hiload 26/60 Superdex 75 318 ml column (17-1070-01 GE Healthcare, Uppsala, Sweden). After concentrating, the final protein concentrations were determined by measuring 280 nm absorbance with a NANO-DROP UV spectrometer. Protein purity was assessed by sodium dodecyl sulfate polyacrylamide gel electrophoresis (SDS-PAGE).

Example 6: Refolding and Purification of Human PGLYRP1 Expressed from E. coli

Human PGLYRP1 was expressed as inclusion bodies in Escherichia coli BL21 (DE3) cells. Bacteria were harvested by centrifugation, resuspended in 50 mM Tris-HCl pH8.0, 500 mM NaCl, 5 mM EDTA, 0.5% Triton X-100 and disrupted by sonication. The insoluble pellet was washed three times with 50 mM Tris, pH 8.0, 1% TritonX-100, 2 M urea and once with 50 mM Tris pH 8.0, then solubilized in 50 mM Tris-HCl. 6M guanidine hydrochloride, pH7.4, 1 mM DTT (final protein concentration 20 mg/ml). For in vitro folding, solubilized human PGLYRP1 inclusion bodies were diluted into 50 mM Tris, pH 8.0, 2 mM EDTA, 5 mM cysteamine, 0.5 mM cystamine, 0.4 M arginine (final protein concentration 1 mg/ml), After overnight at 4° C., the folding mixture was cleared by centrifugation/filtration and then diluted 12 fold into 10 mM MES pH 3.5 to lower the conductivity and pH (final pH ~5.8, conductivity ~6 mS/cm). The diluted folding mixture was then applied to a Hitrap SP HP 5 ml column (17-1151-01 GE Healthcare, Uppsala, Sweden), followed by a 5 column volume wash with 50 mM MES pH 5.8. The bound human PGLYRP1 was then eluted with a 0~60% linear gradient of 50 mM MES pH 5.8, 1 M NaCl in 20 column volume. The fractions containing refolded human PGLYRP1 were pooled and concentrated to less than 4 ml by Amicon ultra 15 centrifugal units (UFC800324 3,000 kDa MWCO, Millipore, Hellerup, Denmark). A Hiload 26/60 Superdex 75 318 ml column ((17-1070-01 GE Healthcare, Uppsala, Sweden) was then used to polish and buffer-exchange the proteins to Phosphate Buffered Saline (PBS). Majority of refolded human PGLYRP1 proteins was in monomer form. After concentrating, the final protein concentration was determined by measuring 280 nm absorbance with a NANODROP UV spectrometer. Protein purity was assessed by sodium dodecyl sulfate polyacrylamide gel electrophoresis (SDS-PAGE).

Example 7: Immunisation of Mice and Identification of mAbs

Purified human PGLYRP1 was used to immunize mice in order to raise antibodies. Briefly, mice were immunised 3 times with 20 µg recombinant PGLYRP1 per immunisation. The first immunisation was subcutaneous using Complete Freunds Adjuvant (cat. no. 3018, Statens Serum Institut, Copenhagen, Denmark). The following two immunisations were intraperitoneal using Incomplete Freunds Adjuvant (cat. no. 3016, Statens Serum Institut, Copenhagen, Denmark). Ten days after the last immunisation, cheek blood was drawn and the sera were tested against PGLYRP1 in a direct ELISA.

Example 8: Binding of Soluble TREM-1 to PGLYRP1

One common method of validating a novel protein-protein interaction is through reconstituting the interaction using recombinant reagents. To this end recombinant human PGLYRP1 was expressed with a C-terminal epitope signalling the posttranslational addition of a glycosylphosphatidylinositol (GPI) structure. Proteins containing terminal GPI structures are targeted for display on the plasma membrane. This commonly applied technique allows otherwise soluble proteins to be displayed and tested for binding by flow cytometric techniques. In FIG. 4A, HEK-2936E cells were transfected with pCDNA 3.1/zeo(+) hPGLYRP1-GPI (SEC ID NO: 7) 3 µg of DNA was diluted into 100 µl of Optimem (Cat. no. 31985062, Life Technologies, Carlsbad, Calif., USA). 4 µl of 293fectin (Cat. no. 51-0031, Life Technologies, Carlsbad, Calif., USA) was added to 100 µl of Optimem (Cat. no. 31985062, Life Technologies, Carlsbad, Calif., USA) and incubated at 22° C. for 5 minutes. The DNA/Optimem mix and the 293fectin/Optimem mix were combined and incubated for an additional 20 minutes at room temperature. HEK-2936E cells were diluted to 3 mls at 1e6/ml in Freestyle media (Cat. no. 12338, Life Technologies, Carlsbad, Calif., USA) and plated in a 6-well dish (Cat. no. 35-3046, Biosciences San Jose, Calif., USA) and then the DNA/293fectin mix was added dropwise to the cells. Cells were incubated for 48 hours at 37° C. with shaking. 1 µg/ml of human TREM-1-G4Sx3-TREM-1/ Fc6mut (SEQ ID NO: 2) was diluted in PBS/2% FBS and 50 µl of probe was added to 80,000 transfected HEK293-6E cells in a round bottom 96-well plate (Cat. no. 3799, Costar, Lowell, Mass., USA). Cells were incubated at 4° C. for 1 hr followed by 2× washes with 200 µl PBS/2% FBS. 50 .µl of 1 µg/ml PE goat anti-human Fc (Cat. no. 109-116-098, Jackson lmmunoResearch, West Grove, Pa., USA) was added and incubated for an additional hour followed by 2× PBS/2% FBS washes. Cells were fixed for 5 min in 1:1 PBS diluted BDCytofix (Cat. no. 554655, BD Biosciences, San Jose, Calif., USA) and incubated for 5 mins followed by a 200 µl PBS/2% FBS wash. Cells were resuspended in 100 µl PBS/2% FBS before being analyzed on a FACS LSRII (BD Biosciences, San Jose, Calif.). The results of this experiment are shown in FIG. 4A where unstained cells are shown by solid black line (G03), TREM-1-G4Sx3-TREM-1/Fc6mut staining of mock transfected cells is shown dashed line, and shows no binding relative to unstained cells. Finally, cells transfected with human PGLYRP1-GPI robustly bind TREM-1-G4Sx3-TREM-1/Fc6mut shown with the dotted line. Quantitation of binding is expressed as mean florescent intensity, MFI.

In addition to flow cytometry, protein-protein interactions are also commonly assessed by measuring surface plasmon resonance (SPR). A BiacoreT200 (GE Healthcare, Piscataway, N.J., USA) instrument was used to analyze the interaction between human TREM-1 & human PGLYRP1 and also between human PGLYRP1 &sonicated, soluble E. coli peptidoglycan (Cat. no, tlrl-ksspgn, Invivogen, San Diego, Calif., USA). All assays were performed at 25° C. at flow rates of 20-30 µL/minute in 1× HBS-P running buffer (Cat. no. BR-1006-71, GE Healthcare, Piscataway, N.J., USA).

Figure 4B:
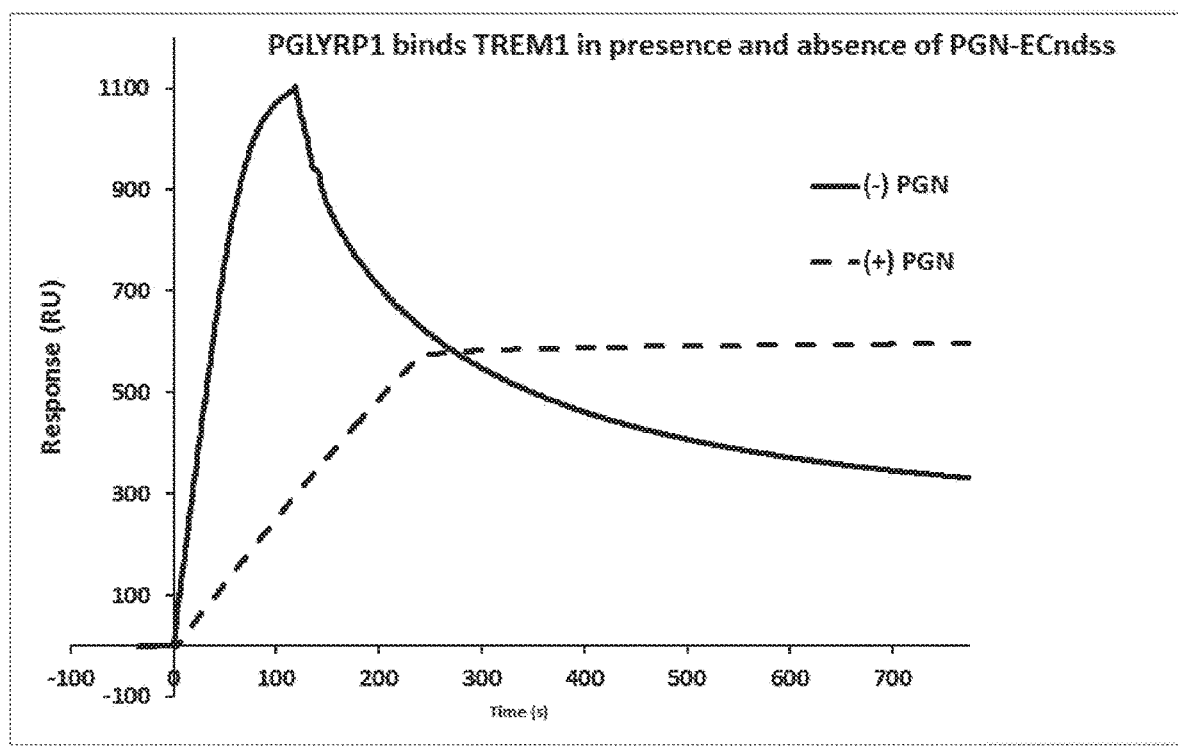
FIG. 4A and FIG. 4B show that soluble TREM-1 binds to PGLYRP1. Shown both by flow cytometric staining with TREM-1 on HEK293 transfectants expressing recombinant PGLYRP1 (FIG. 4A) and by Biacore and ForteBio analyses of the interaction between PGLYRP1 and a TREM-1 tetramer (SEQ ID NO: 2). Soluble human PGLYRP1 bound immobilized human TRENT-1 in the presence and absence of 10 µg/ml soluble E. coli peptidoglycan (a PGN) (FIG. 4B). PGN by itself also bound immobilized human PGLYRP1 (FIG. 4C), and soluble human TREM-1 bound to immobilized PGLYRP1 before and after the PGLYRP1 surface was exposed to and bound by PGN (FIG. 4D).

In FIG. 4B, 4641.1 RU of human TREM-1 tetramer (SEQ ID NO: 2) was amine coupled to a Biacore CM5 chip (Cat. no, BR-1005-30, BR-1000-50, GE Healthcare, Piscataway, N.J., USA) following the manufacturer's recommended methods. PGLYRP1 (Cat. no. 2590-PG, R&D Systems, Minneapolis, USA) was diluted to 150 nM in 1× HBS-P running buffer (Cat. no. BR-1006-71, GE Healthcare, Piscataway, N.J., USA) in the presence or absence of 10 µg/mL soluble E. coli peptidoglycan (Cat. no. tlrl-ksspgn, Invivogen, San Diego, Calif., USA) and injected over the TREM-1 surface. Data is reference subtracted vs, an activated and blocked (with ethanolamine) reference surface. Though PGLYRP1 binds TREM-1 both in presence and absence of PGN, there appears to be a significant avidity effect when PGLYRP1 is crosslinked by PGN.

Figure 4C:
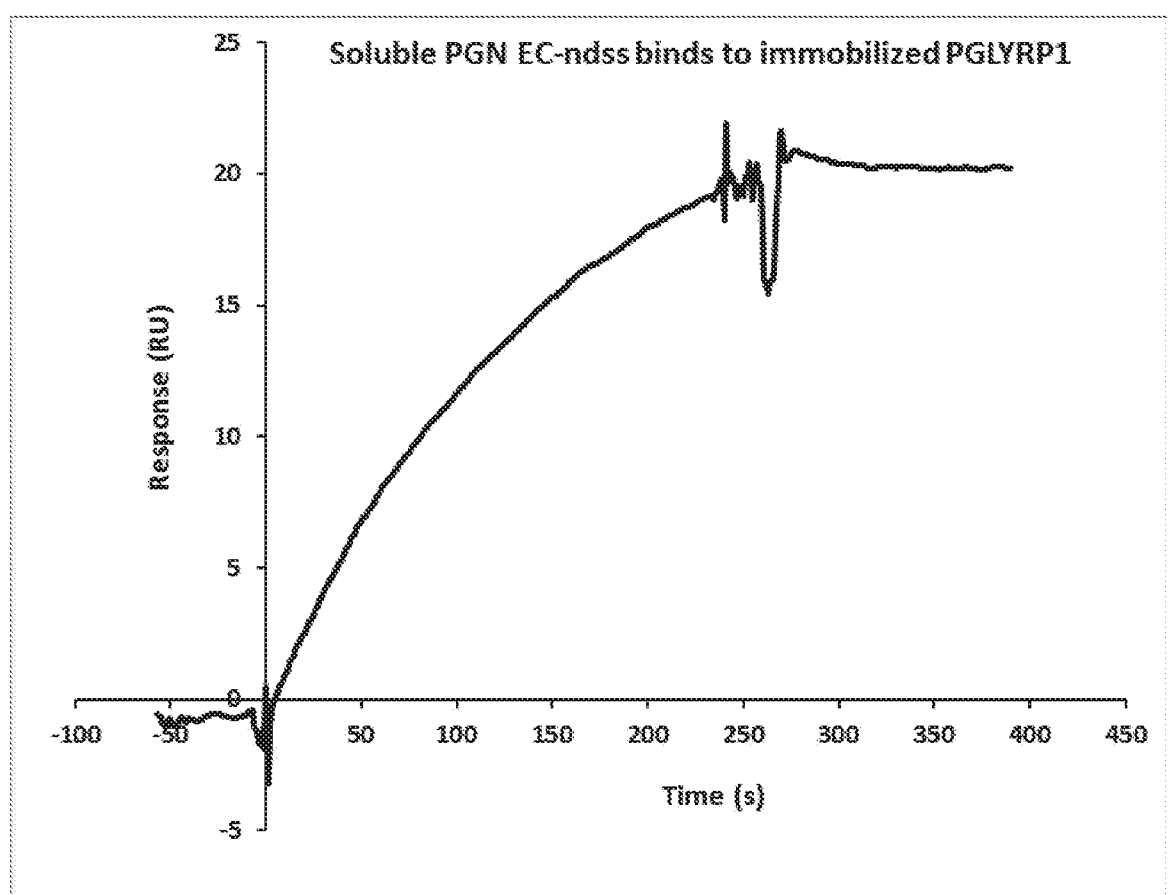

In FIG. 4C, 274.8 RU of PGLYRP1 dimer (SEQ ID NO: 1) were amine coupled to a Biacore CM5 chip (Cat. no. BR-1005-30, BR-1000-50, GE Healthcare, Piscataway, N.J.). Soluble E. coli peptidoglycan (Cat. no, tlrl-ksspgn, Invivogen, San Diego, Calif., USA) was diluted to 10 µg/mL in 1× HBS-P running buffer (Cat. no. BR-1006-71, GE Healthcare, Piscataway, N.J., USA) and injected over the PGLYRP1 surface. Data is reference subtracted vs. an activated and blocked (with ethanolamine) reference surface.

Figure 4D:
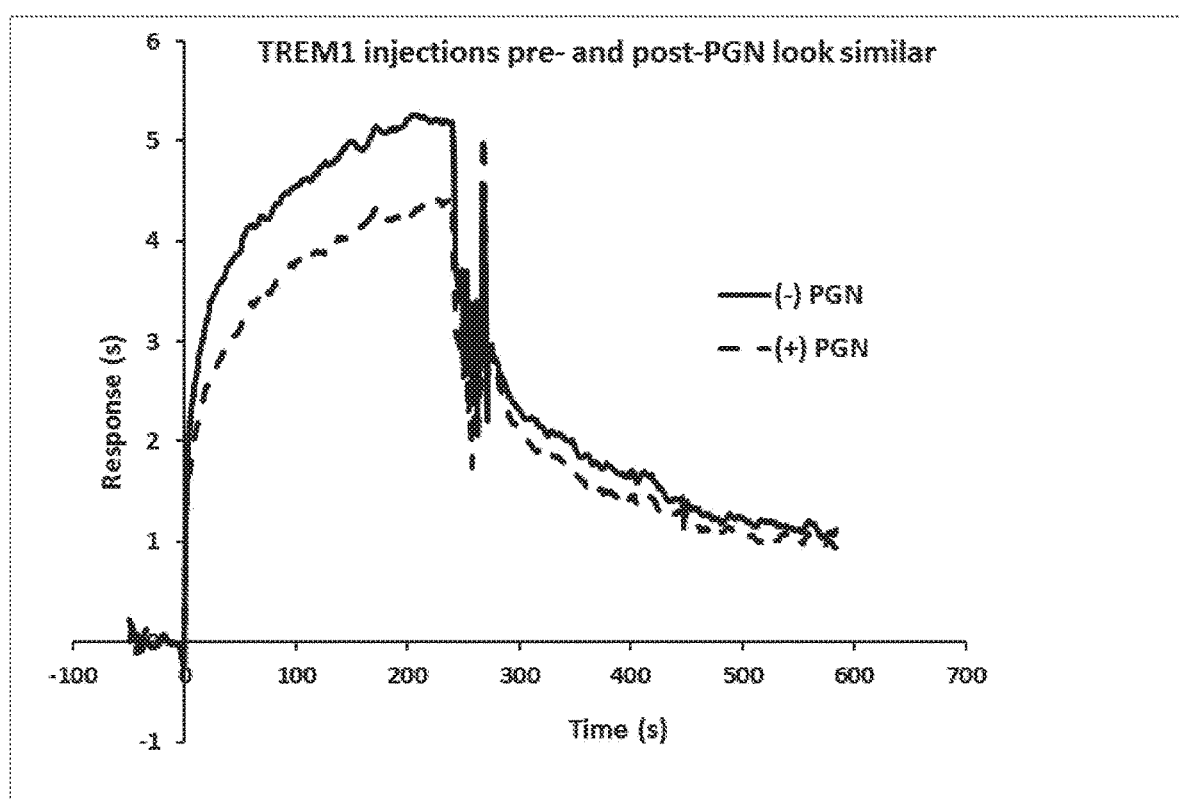

In FIG. 4D, the same chip was used as in FIG. 4C, (274.8 RU of PGLYRP1 dimer, (SEQ ID NO: 1). TREM-1 dimer (SEQ ID NO: 8) was diluted to 150 nM in 1× HBS-P running buffer (BR-1006-71, GE Healthcare, Piscataway, N.J., USA) and injected both before and after repeated injections of peptidoglycan (depicted in FIG. B). Data is reference subtracted vs. an activated and blocked (with ethanolamine) reference surface and the signal of a buffer blank injection is also subtracted. TREM-1 shows clear binding to immobilized PGLYRP1. Soluble TREM-1 dimer binds similarly to immobilized PGLYRP1 alone or to PGLYRP1 that has been loaded with PGN. Overall binding of surface immobilized TREM-1 receptor by soluble PGLYRP1 and PGN consists of a modest affinity for the PGLYRP1:TREM-1 complex enhanced by an avidity effect from the highly crosslinked PGLYRP1.

Example 9: Activation of TREM-1-Response by Recombinant PGLYRP1

Figure 5A:
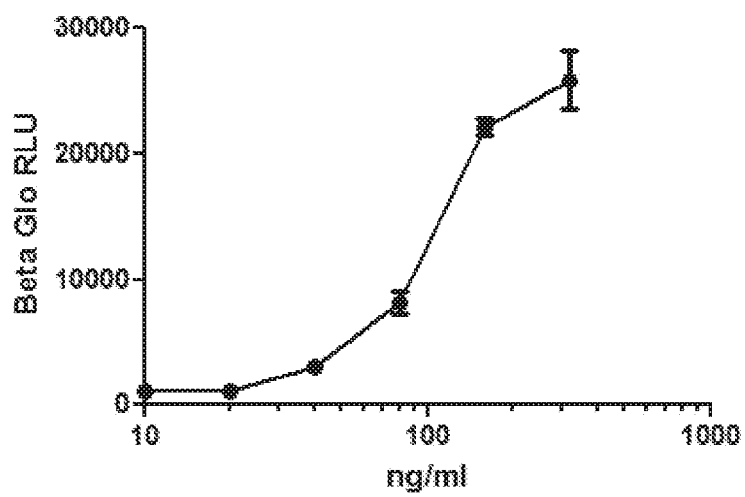
FIG. 5A and FIG. 5B show activation of a TREM-1 reporter cell line by recombinant PGLYRP1. Stimulation of a TREM-1 reporter cell line with recombinant PGLYRP1 (cat. no. 2590-PG-050 R&D Systems Minneapolis Minn., USA), as well as PGLYRP1 generated in-house (SEQ ID NO: 1) leads to a dose dependent response in the presence of PGN (FIG. 5A). This PGLYRP1-induced response can be specifically blocked by TREM-1-Fc fusion protein (FIG. 5B) validating a TREM-1 specific signal.

To test if recombinant PGLYRP1 can activate a TREM-1 response, the BWZ/hTREM-1 reporter cell line was seeded into black 96 well plates and stimulated with recombinant human PGLYRP1 (Cat, no. 2590-PG-050, R&D Systems: Minneapolis, Minn.) in the presence or absence of 10 μg/ml PGN. TREM-1 activation was read out after 24 hours of culture using the BetaGlo reagent (Cat. no. E4720, Promega Madison, Wis., USA) and luminescence measured using a TopCount Luminescence counter from Perkin Elmer. As shown in FIG. 5A, stimulation of the TREM-1 reporter cell line with PGLYRP1 induced a dose-dependent activation of TREM-1 in the presence of PGN. Several different PGN were tested, including PGN-EC (from *E. coli*), PGN-SA (from *S. aureus*) and PGN-BS (from *B. subtilis*) (Invivogen, San Diego, Calif., USA), and were all able to fascilitate the PGLYRP1-induced TREM-1 response.

Figure 5B:
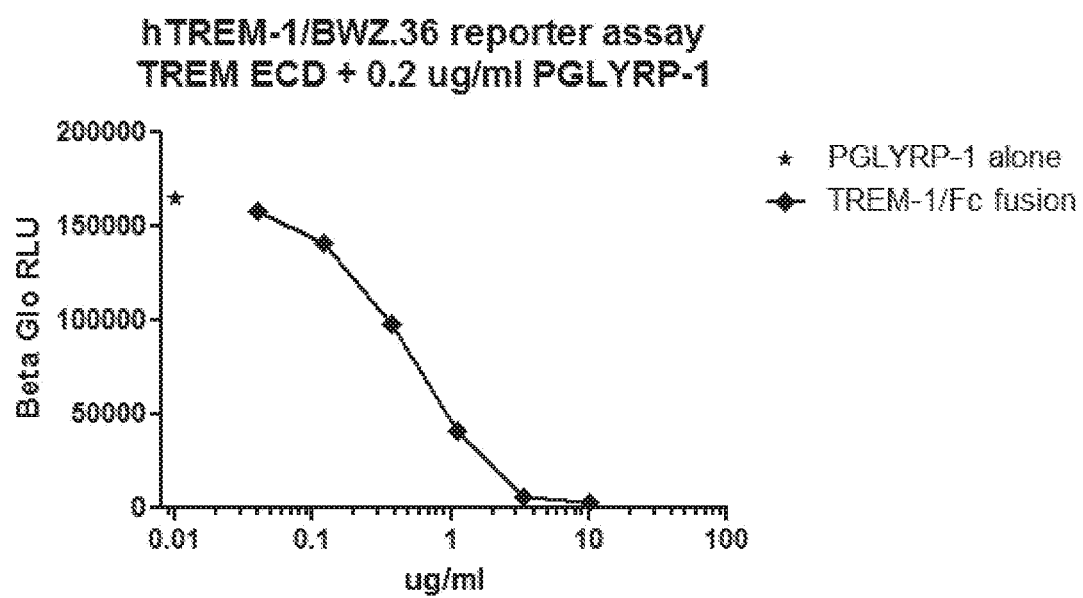

The response induced by recombinant PGLYRP1 could be inhibited by addition of a recombinant TREM-1-Fc-fusion protein (SEQ ID NO: 2) (FIG. 5B) or by addition of polyclonal anti-PGLYRP1 antibody (Cat. no. AF-2590, R&D Systems: Minneapolis, Minn., USA) confirming that PGLYRP1 is the TREM-1 ligand and that soluble TREM-1 and anti-PGLYRP1 are potentially useful as TREM-1 antagonists.

Example 10: TNFalpha Release from M1 Macrophages Stimulated by PGLYRP1

Monocytes were differentiated into M1 macrophages and stimulated with PGLYRP1 complex resulting in TNFalpha release in two different donors.

Those skilled in the art will recognize the value of establishing a freezer bank collection of primary cells from multiple donors thus providing for convenient replication of experiments. In vitro derived macrophages were produced from peripheral blood monocytes as follows. Negatively enriched monocytes were isolated from a peripheral blood "leukopak" obtained from Research Blood Components (Brighton, Mass., USA) using a Rosette Sep kit (cat. no. Cat, no. 15068 Stem Cell Technologies, Vancouver BC, Canada) following the manufacturer's instructions. Isolated monocytes were suspended in 10% DMSO/FBS aliquots of 50e6 cell/ml and gradually cooled to −80C. To produce macrophage cells, one or more frozen vials of monocytes were rapidly thawed in a 37 C water bath, diluted to 10 ml with growth media [RPMI 1640 (Cat. no. 72400-047, Life Technologies, Carlsbad Calif., USA)) with 10% FBS (Cat. no. 03-600-511, Themo Fisher, Waltham Mass., USA) and centrifuged 5 minutes at 250 g. Cells were suspended to 2e6 cells/ml in growth media supplemented with 50 ng/ml human MCSF (Cat. no. PHC9501, Life Technologies, Carlsbad Calif., USA), placed into tissue culture treated, petri style tissue culture plates and into a humidified incubator programmed to maintain a "hypoxic" atmosphere of 5% CO2, 2% O2. On the third day in culture, the cells were fed with the addition of an equal volume of growth media supplemented with 50 ng/ml human MCSF. After 6 days in culture the monocytes had differentiated into M0 macrophages. M0 cells were further differentiated by changing the media to growth media supplemented with 50 ng/ml human IFNg (Cat. no., PHC4031, Life Technologies, Carlsbad Calif., USA) for M1 macrophages or 40 ng/ml human IL-4 (Cat. no. PHC0045, Life Technologies, Carlsbad Calif., USA) for M2 macrophages and returning to the incubator for an additional 22 hours. On the seventh day, macrophages were suitably differentiated to be used in a bioassay. Briefly, macrophages were recovered from the petri plates by washing with 1× PBS, followed by 5 mM EDTA in PBS. The plates were then returned to 37 C for 30 minutes and cells were "power washed" off the plate using a 10 ml syringe and 22 G needle. Cells were then diluted into growth media, centrifuged at 250 g for 5 minutes after which the cell pellet was suspended to a final concentration of 1e6/ml.

Macrophage cells prepared as above were used in bioassays where cytokines such as TNF-alpha produced in response to stimulation of the cells with TREM-1 ligand were measured in the conditioned media by ELISA. Such a bioassay was further utilized to measure blockade of TREM-1 ligand stimulation by TREM-1 specific antibodies. TREM ligand or negative controls were prepared at 4× concentrations in growth media and 50 microliters/well were added to 96 well microtiter dishes. Final concentrations of TREM-1 ligand consisted of 7.5 ng/ml recombinant human PGLYRP1 (generated as described in example 5) and 3 μg/ml PGN-BS (Cat. no. tlrl-pgnbs, Invivogen, San Diego Calif., USA). Cells were cultured under humidified hypoxic conditions as described above for 22 hours after which conditioned media was collected and TNF-alpha levels were measured by ELISA, following manufacturer's instructions (Cat. no. DY210, R&D Systems, Minneapolis Minn., USA).

| M1 macrophage with: | Donor 1 TNF-α, pg/ml | | Donor 2 TNF-α, pg/ml | |
|---|---|---|---|---|
| | Avg | SD | Avg | SD |
| No addition | 0 | 0 | 22 | 1 |
| 0.4 μg/ml PGN-BS | 357 | 153 | 764 | 139 |
| 2.0 μg/ml PGN-BS | 3086 | 151 | 5792 | 226 |
| 5 μg/ml PGLYRP1 + 0.4 μg/ml PGN-BS | 7502 | 384 | 7819 | 945 |
| 5 μg/ml PGLYRP1 + 2 μg/ml PGN-BS | 31440 | 1030 | 40418 | 1633 |

This example shows that the TREM-1 ligand PGLYRP1 is able to further increase TNFa release from macrophages from two different donors.

Example 11: Cytokine Release from Synovial Tissue Cells from RA Patients Upon Stimulation with PGLYRP1

Synovial tissue samples were obtained from RA patients during total knee replacement. Single suspension of synovial tissue cells was isolated by a digestion via 4 mg/ml of collagenase (Cat. no. 11088793001, Roche, Mannheim, Germany) and 0.1 mg/ml of DNase (Cat. no. 11284932001, Roche, Mannheim, Germany) for 1 h at 37 degree. Synovial tissue cells at 1×10^5/well in culture medium RPMI (Cat, no, R0883, Sigma Aldrich, St Louis, Mo., USA)+10% FCS (Cat. no. S0115, BioChrom AG, Grand Island, N.Y. 14072, USA) were stimulated with 4 ug/ml of PGLYRP1 and 1 ug/ml of PGN-ECNDi (Cat. no. tlrl-kipgn, Invivogen, San Diego, Calif. 92121, USA). After 24 h incubation, cell supernatants were harvested, and cytokines were measured by either ELISA (TNFa (Cat, no, DY210, R&D Systems, Minneapolis, Minn. 55413 USA), IL-1b (Cat, no. 88-7010-88, eBioscience, San Diego Calif. USA), GM-CSF (Cat. no. 88-7339-88, eBioscience, San Diego Calif. USA) or Flowcytomix (TNFa, IL-1b, MIP-1b, MCP-1, IL-6, and IL-8 (Cat. no. BMS, eBioscience, San Diego Calif. USA). The cytokines were secreted from the synovial tissue cells upon stimulation with the TREM-1 ligand.

| Cytokine (pg/ml) | PGN | PGN + PGLYRP1 |
|---|---|---|
| TNFalpha | 623.69 | 1444.59 |
| IL-1beta | 2419.42 | 3772.74 |
| GM-CSF | 181.91 | 615.91 |
| MIP-1beta | 2457.955 | 4394.725 |
| MCP-1 | 273.055 | 471.26 |
| IL-6 | 2056.94 | 4189.355 |
| IL-8 | 2574.56 | 5509.195 |

This example shows that cells from synovial tissue from rheumatoid arthritis patients will respond to stimulation by the TREM-1 ligand PGLYRP1 by secreting numerous cytokines.

Example 12: Identification of Anti-PGLYRP1 mAbs that Inhibit TREM-1 Activation

Figure 6B:
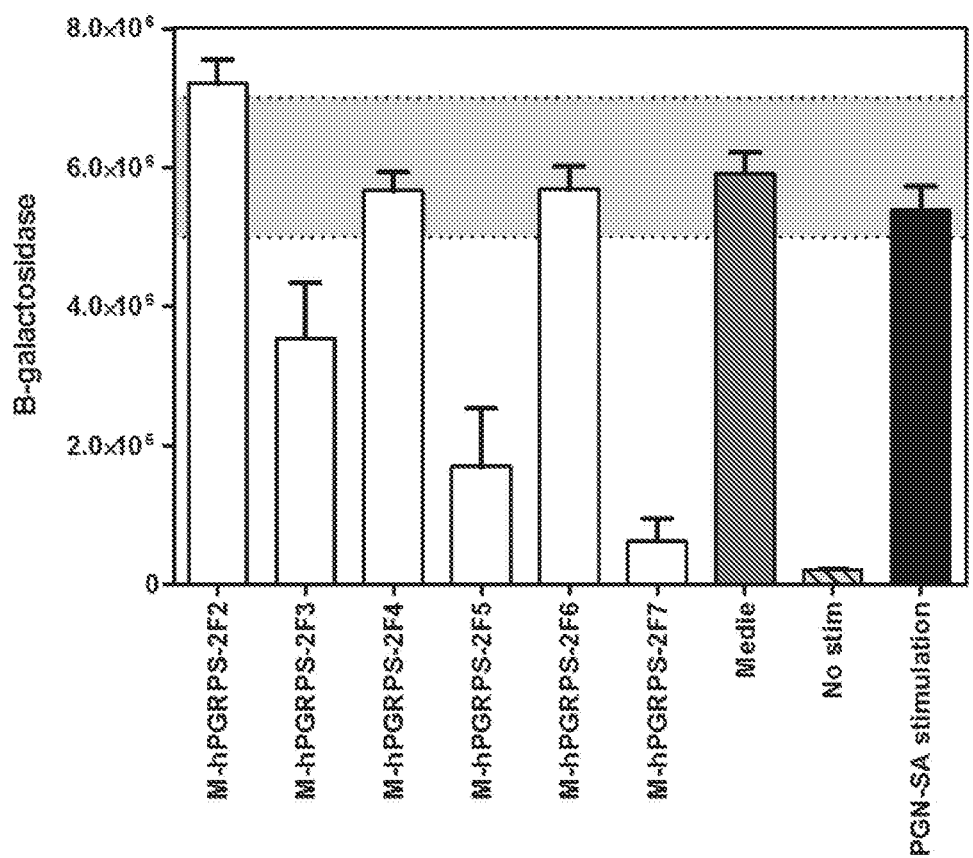
Figure 6C:
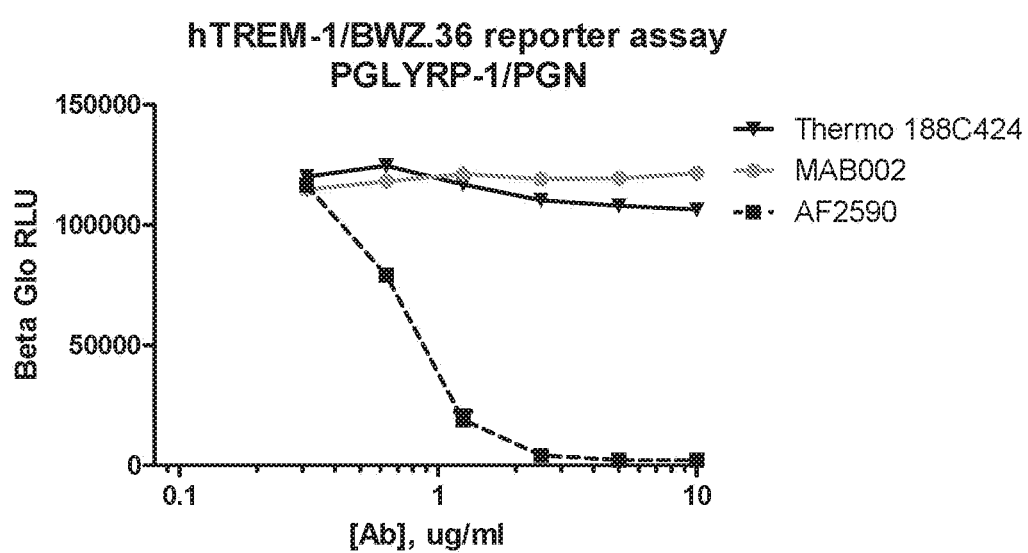
Figure 6D:
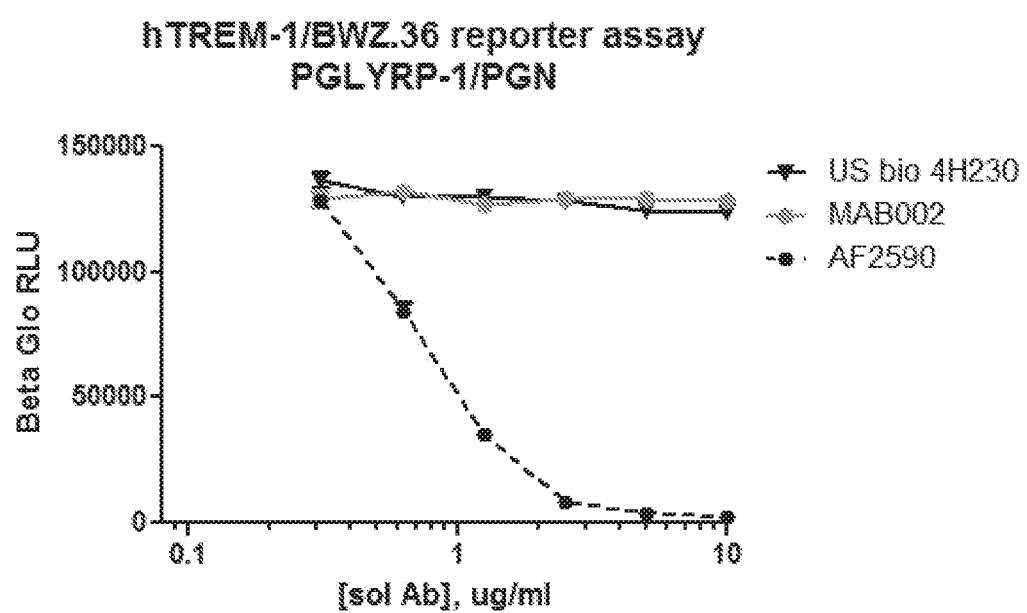
Figure 6E:
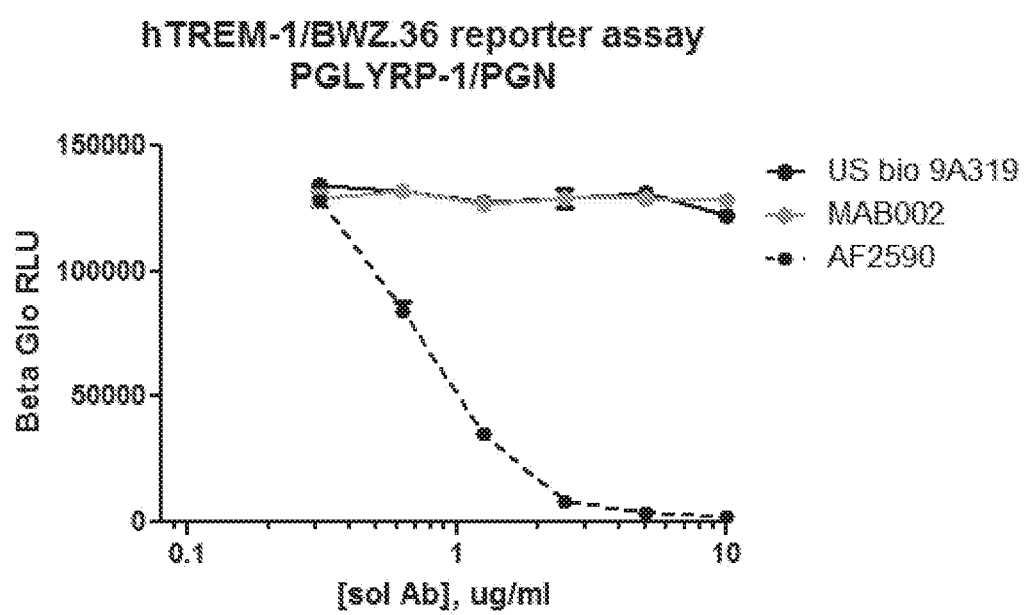
Figure 6F:
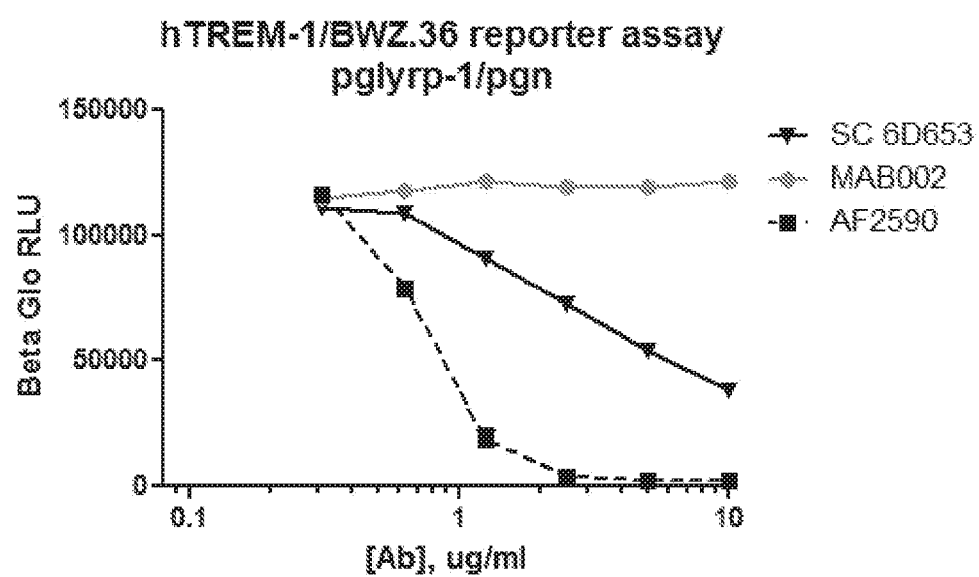
Figure 6G:
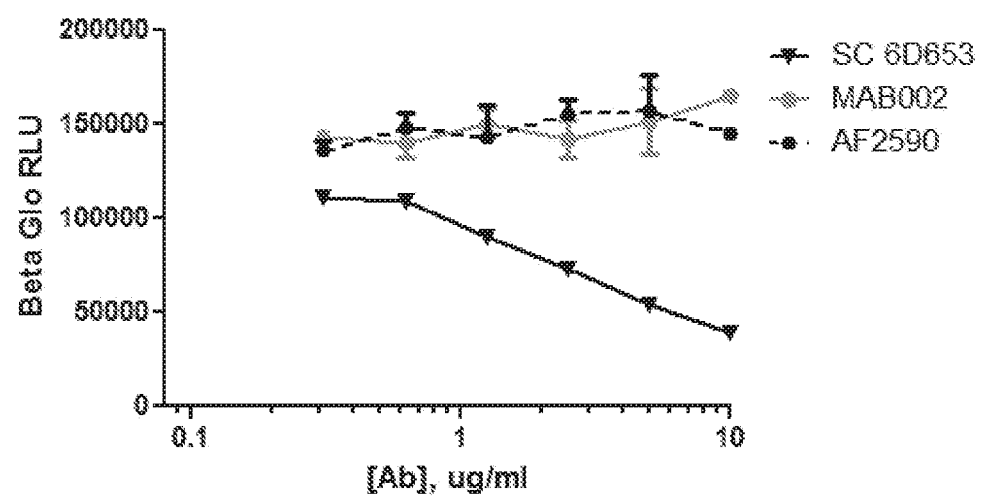
Figure 7:
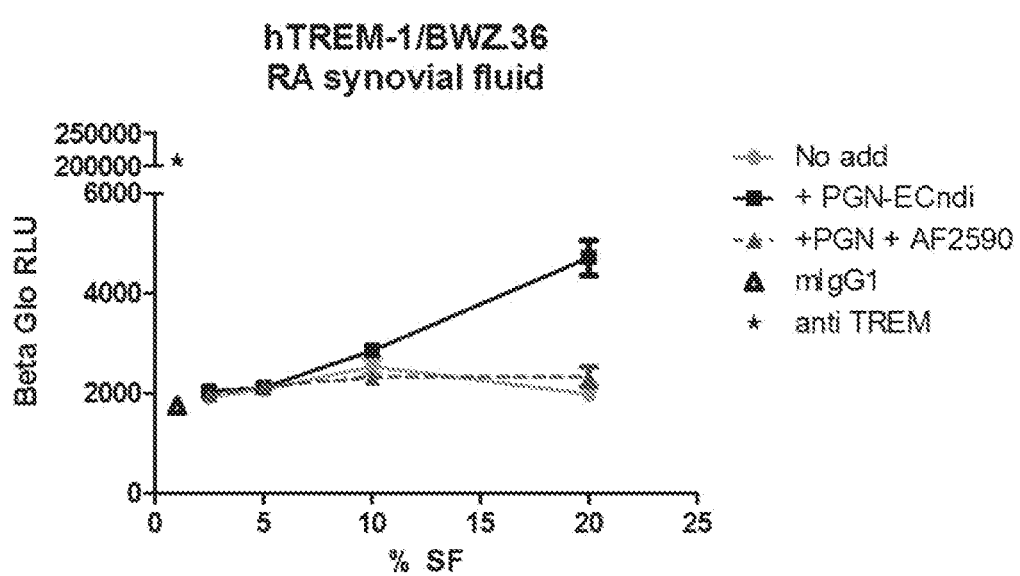
FIG. 7 shows that the TREM-1 ligand present in human RA synovial fluid is able to stimulate TREM-1.

In order to identify monoclonal anti-PGLYRP1 mAbs that can block TREM-1 responses, wtbalb/c mice were immunized with recombinant human PGLYRP1. Primary screening was done by means of direct ELISA on PGLYRP1 protein, and all PGLYRP1-specific hybridoma supernatants were subsequently tested in the BWZ/hTREM-1 reporter cell assay to identify monoclonal anti-PGLYRP1 antibodies capable of inhibiting TREM-1 activation induced by PGN-stimulated neutrophils, as described under example 1. The bioassay was run as follows: 40,000 hTREM-1/BWZ.36 cells/well were plated in a clear bottom, black 96 well plate in the presence of 75 ng/ml PGLYRP1 (SEQ ID NO: 1) with 2.5 µg/ml PGN-ECndi (Cat. no, tlrl-kipgn, Invivogen San Diego, Calif., USA) to provide a sub-maximal positive signal, or alternatively in the presence of a sub-maximal level (1 µg/ml) of plastic adsorbed anti TREM-1 monoclonal antibody (Cat. no. MAB1278 R&D Systems, Minneapolis, Minn., USA) to provide a positive signal. Test antibodies were titered into the assay starting at 10 µg/ml, with 5 serial 2-fold dilutions. The assay was incubated overnight at 37 C, and developed with Beta Glo (Cat. no. E4740,Promega Madison, Wis., USA), as per the Beta Glo protocol, and luminescence was recorded. Data was plotted showing Beta Glo relative luminescent units vs test antibody concentration. Non-neutralizing negative control mIgG1 (Cat. no. MAB002, R&D Systems Minneapolis, Minn., USA) and neutralizing positive control polyclonal goat anti hPG-LYRP1 antibody (Cat. no. AF2590, R&D Systems, Minneapolis, Minn., USA) were run on each assay plate. As shown in FIG. 6A, F10, F14, F29, F36, F38, F77, F95 and F105 were identified as being able to block the TREM-1 response to PGLYRP1. FIG. 6B shows other PGLYRP1 antibody hybridoma supernatants able to block the TREM-1 dependent signal. M-hPGRPS-2F5 (SEQ ID NOs: 31-32 and -2F7 (SEQ ID NOs: 35-36) are very efficient blockers. In contrast, testing of commercially available monoclonal anti-PG-LYRP1 antibodies in the same assay protocol alongside the antiPGLYRP1 goat polyclonal positive control (Cat, no. AF2590, R&D Systems Minneapolis, Minn., USA) showed that none of these could block TREM-1 activation (FIG. 6C). The anti PGLYRP1 antibodies tested include: 188C424 from Thermo Scientific (6D), 4H230 and 9A319 Mabs from US Biological (FIG. 6D, 6E); all failed to block PGLYRP1 stimulation of the TREM-1 bioassay. Clone 6D653 from Santa Cruz Biotechnology (FIGS. 6F and 6G) had was found to block the assay non-specifically based on the observation that the Mab blocked both PGLYRP1 (6F) and anti-TREM-1 stimulation (6G) while the positive control anti PGLYRP1 polyclonal Ab only blocked PGLYRP1 mediated activation. This non-specific blocking may be due to azide toxicity on the bioassay.

In conclusion, PGLYRP1 monoclonal antibodies have been identified that not only bind PGLYRP1 but also neutralize its TREM-1 signalling activity. The method used to identify these molecules provides a unique advantage over routine methods used to identify PGLYRP1 antibodies, evidenced by the failure of available commercial antibodies to neutralize PGLYRP1.

Example 13: PGLYRP1 Antibodies Block a TREM-1 Specific Signal

PGLYRP1 hybridoma clones were sequenced and recombinantly expressed as a hIgG4 antibody. Two of these mAb 0182 (from 1F36) (SEQ ID 15 and 16) and mAb 0184 (from 1F105) (SEQ ID 23 and 24) were retested in the BWZ/hTREM-1 reporter cell assay as described in example 13. These anti-PGLYRP1 antibodies block the TREM-1 response in the BWZ/hTREM-1 reporter cell assay in a dose-dependent manner.

| | BWZ.36/hTREM-1 response, Beta Glo RLU Antibody | | | | | |
|---|---|---|---|---|---|---|
| | Isotype | | 182 | | 184 | |
| ug/ml | Avg | SD | Avg | SD | Avg | SD |
| 0 | 74636 | 10004 | 74636 | 10004 | 74636 | 10004 |
| 0.16 | 70289 | 13018 | 81858 | 3336 | 60738 | 5449 |
| 0.31 | 68555 | 5585 | 73382 | 650 | 59830 | 2837 |
| 0.63 | 68105 | 11547 | 73831 | 7818 | 51198 | 397 |
| 1.25 | 71797 | 8545 | 63280 | 1663 | 46447 | 708 |
| 2.5 | 69207 | 5004 | 51675 | 1270 | 42062 | 1953 |
| 5 | 76951 | 901 | 33641 | 842 | 36194 | 1461 |
| 10 | 83930 | 8962 | 20655 | 1080 | 25239 | 407 |
| 20 | 74555 | 511 | 11852 | 464 | 21333 | 115 |
| 40 | 72296 | 8228 | 7696 | 306 | 15693 | 1861 |

This example shows that, in contrast to the commercial available antibodies against PGLYRP1 shown in FIG. 6C-G, the PGLYRP1 antibodies disclosed herein are able to block the TREM-1 specific signal in the BWZ/hTREM-1 reporter cell assay.

Example 14: TNF-Alpha Release from M2 Macrophages Stimulated by PGLYRP1

Monocytes were differentiated into M2 macrophages and stimulated with PGLYRP1 complex. Antibodies (10 µg/ml) mAb −0182 and −0184 directed against PGLYRP1 is able to lower the TNF-alpha release. M2 macrophages were differentiated as described in Example 10. Antibodies to be tested were prepared at 4× concentrations in growth media and 50 microliters/well were added. The final step in initiating the bioassay was the addition of 100 microliters/well of M2 macrophage cells prepared as described above. PGLYRP1 monoclonal antibodies (mAb 0182 and mAb 0184) were tested for neutralizing activity on M2 macrophages. Duplicate (unless otherwise noted) test wells were tested under the following conditions: no added stimulation, 7.5 ng/ml PGLYRP1 only, 3 µg/ml PGN-BS (Cat. no. tlrl-pgnbs, Invivogen San Diego, Calif., USA) only (sextuplicates), PGLYRP1 with PGN-BS (sextuplicates), and PGLYRP1 with PGN-BS in the presence of PGLYRP1 antibodies or hIgG4 isotype control antibody titrated in at concentrations between 40 µg/ml and 0.31 µg/ml in 2 fold dilutions.

| M2 macrophages with: | Donor 1 TNF-α, pg/ml | | Donor 2 TNF-α, pg/ml | |
|---|---|---|---|---|
| | Avg | SD | Avg | SD |
| No addition | 108 | 42 | 68 | 16 |
| PGLYRP1 | 167 | 98 | 89 | 33 |
| PGN | 424 | 105 | 635 | 156 |
| PGLYRP1 + PGN | 1660 | 198 | 2168 | 210 |
| PGLYRP1 + PGN + isotype | 1726 | 182 | 2483 | 251 |
| PGLYRP1 + PGN + mAb 0182 | 1322 | 173 | 2014 | 107 |
| PGLYRP1 + PGN + mAb 0184 | 1207 | 168 | 1948 | 173 |

This example illustrates that the TREM-1 ligand PGLYRP1 is able to further increase TNFa release from M2 macrophages from two different donors and that the antibodies disclosed herein are able to decrease such TNFa release. Therefore, these PGLYRP1 antibodies are potentially useful as TREM-1 antagonists.

Example 15: Survey of Binding Interactions Between TREM-1 and PGLYRP1 Related Molecules Confirms Specificity Having identified TREM-1 as being able to bind to PGLYRP1 and activate TREM-1 in the presence of PGN, we set out to determine whether or not TREM-1 could bind to the other PGLYRP family members. PGLYRP1 was artificially anchored in the cell-membrane through addition, at the N-terminus, of an intracellular (IC) and transmembrane domain (TM) derived from the Type II receptor MDL-1. The latter constructs were denoted Type II PGLYRP1. In Type II 1.0 (SEQ ID NO: 37), the charged amino acid of the native MDL-1 receptor TM is maintained, and efficient expression of this protein, is dependent on co-expression of DAP12. In the Type II 2.0 PGLYRP1 construct (SEQ ID NO: 38), the charged TM residue has been substituted with a neutral amino acid (Lysine to Leucine), enabling the protein to be expressed independently of eg. DAP12, and an epitope tag of DYKDDDDK (SEQ ID NO: 39) was added. Full length hPGLYRP2 (SEQ ID NO: 40), hPGLYRP3 (SEQ ID NO: 41), and hPGLYRP4 (SEQ ID NO: 42]), cDNAs were synthesised as membrane anchored proteins using N terminal fusion of the TypeII 2.0 MDL1 N terminus as utilized for PGLYRP1 above, cDNAs were subcloned into a modified pTT5 expression plasmid vector (Zhang J et al. Protein Expression and Purification, Vol. 65, Issue 1, May 2009, pp 77-8), and transfected as described in example 8 into HEK293-6E cells alongside an empty vector negative control (Mock). Cells were assayed by flow cytometry for both surface and intracellular binding of the following probes: goat anti-human PGLYRP1 (PGRPS) (Cat. no. AF2590, R&D Systems, Minneapolis, Minn., USA); Mab anti-human PGLYRP2 (PGRP-L) (Cat. no, MAB0755, Abnova, Walnut, Calif., USA); Mab anti-human PGLYRP3 (PGRP-1a) (Cat. no. MAB0068, Abnova, Walnut, Calif., USA); Mab anti-human PGLYRP3 (PGRP-1a) (Cat. no. ab13901, Abcam, Cambridge Mass., USA); rabbit anti-human PGLYRP3 (PGRP-1a) (Cat. no. 18082-1-AP, Protein Tech, Chicago Ill., USA); goat anti-human PGLYRP4-biotin (PGRP-1b) (Cat. no. BAF3018, R&D Systems, Minneapolis, Minn., USA); goat anti-mouse PGLYRP1 (PGRPS) (Cat. no. AF2696, R&D Systems, Minneapolis, Minn., USA); huTREM-1.Fc dimer (C0099), huTREML1.Fc dimer (CO246), huTREML2.Fc dimer (CO247); huTREM2,Fc dimer (C0248); The binding protocol was conducted as follows, using either cytofix/perm buffer (Cat. no. 51.2090KZ, BD Biosciences, San Jose Calif., USA) for intracellular staining or 2% FBS/PBS for surface staining: cell pellets were resuspended in a 96-well round bottom plate (to begin with: 160,000 cells/well) with 200 µl cytofix/perm buffer for 15 minutes at 22 C, washed twice with 200 µl 1× PermWash Buffer (diluted 10× in DiH20), stained with 50 µl probe diluted to 5 □g/ml in 1× PermWash buffer, incubated for 1 hour at 4 C, cells were then washed with 200 µl 1× PermWash Buffer, a secondary probe was added in 50 µl 1× PermWash buffer, cells were incubated at 4 C for 30 minutes, washed twice with 200 µl 1× PermWash Buffer, pellets were resuspended in 50 µl 1 1:1 PBS diluted CytoFix (BD:554655, San Jose, Calif.), incubated for 5 minutes at 22 C, 150 µl PBS/2% FBS was added, centrifuged for 5 minutes at 300 g, washed 1× with 200 µl PBS/2% FBS and resuspended in 100 µl PBS/2% FBS. Binding was analysed using FACS on LSRII (BD, San Jose Calif., USA).

As summarised in the table below, TREM-1 probe bound exclusively to hPGLYRP1 and no hTREM family member binding to PGLYRP2, PGLYRP3 or PGLYRP4 was detected.

| | Mock | Type II PGLYRP1 | Type II PGLYRP2 | Type II PGLYRP3 | Type II PGLYRP4 | Type II PGLYRP3 + 4 | Type II muPGLYRP1 |
|---|---|---|---|---|---|---|---|
| anti huPGLYRP1 (R&D, AF2590) | − | ++++ | − | − | ++ | + | ++++ |
| anti huPGLYRP2 (Abnova, MAB07755) | − | − | ++++ | − | − | − | n/d |
| anti huPGLYRP3 (Abnova, MAB0068) | − | − | − | − | − | − | n/d |
| anti huPGLYRP3 (Abcam, ab13901) | − | − | − | − | − | − | n/d |
| anti huPGLYRP3 (Proteintech, 18082-1-AP) | − | − | − | − | − | − | n/d |
| anti huPGLYRP4 (R&D, BAF3018) | − | ++++ | − | − | ++++ | ++++ | n/d |
| anti muPGLYRP1 (R&D, AF2696) | − | ++++ | n/d | n/d | n/d | n/d | ++++ |
| huTrem1.Fc (C0099) | − | ++++ | − | − | − | − | − |

-continued

| | Mock | Type II PGLYRP1 | Type II PGLYRP2 | Type II PGLYRP3 | Type II PGLYRP4 | Type II PGLYRP3 + 4 | Type II muPGLYRP1 |
|---|---|---|---|---|---|---|---|
| huTremL1.Fc (C0246) | − | − | − | − | − | − | − |
| huTremL2.Fc (C0247) | − | − | − | − | − | − | n/d |
| huTrem2.Fc (C0248) | − | − | − | − | − | − | n/d |

Human membrane anchored PGLYRP1, PGLYRP2, PGLYRP3 and PGLYRP4 were transiently expressed in HEK293 and probed with both in-house and commercial soluble receptors and antibodies in order to identify new interactions between family members. Binding scores were expressed as "n/d", "−", "+" or "++++". Scores are a ratio of mean florescent intensity (MFI) of probe staining over negative control staining; "−" equals a ratio of <1, "++++" represents a score of >30 and "++" represents approximately 10-15, "+" represents 2-5 with a statistically significant difference (p<0.05). Those skilled in the art may characterize this scoring as negative, bright or dim respectively.

TREM-1 only binds to PGLYRP1 and none of the other PGLYRP members, and vice versa: PGLYRP1 only interacts with TREM-1 and none of the other TREM members.

Example 16: TREM-1 Ligand is Present in RA Synovial Fluid Samples

Rheumatoid arthritis is characterized by metacarpophalageal (MCP) joint inflammation in which activated granulocytes play a significant role. PGYLRP1 was assayed by ELISA and tested in BWZ/hTREM-1 reporter cell assay from synovial fluid drawn from MCP joints of 9 RA patients. Commercially sourced synovial fluid (Asterand, Detroit Mich., USA) was thawed, vortexed and serially diluted in ELISA buffer and run in a PGLYRP1 assay following the manufacturers guidelines (Promega, Madison Wis., USA) Four of 9 patients showed elevated PGLYRP1 levels:

| RA SF donor | PGLYRP1, ng/ml | |
|---|---|---|
| | Avg | SD |
| 1 | 14 | 5 |
| 2 | 8 | 1 |
| 3 | 213 | 44 |
| 4 | 229 | 58 |
| 5 | 135 | 49 |
| 6 | 47 | 4 |
| 7 | 39 | 13 |
| 8 | 116 | 33 |
| 9 | 32 | 1 |

Figure 8:
FIG. 8 shows the overall structure of the Type II PGLYPR1 construct. IC represents the intracellular domain, TM the transmembrane domain—both of which originate from MDL-1 protein sequence, in combination with EC (extracellular) domain of hPGLYRP1.

The RA synovial fluid samples were subsequently assayed for TREM ligand activity in the BWZ reporter assay as described in example 2. Briefly synovial fluid was thawed, vortexed, and serially diluted, assayed in duplicate +/−10 μg/ml PGNECndi (Invivogen, San Diego, Calif., USA) with the addition of polyclonal PGLYRP1 antibody (Cat. no. AF2590, Promega, Madison Wis., USA) or a negative control polyclonal. Plastic adhered monoclonal TREM-1 and isotype antibodies (R&D Systems, Minneapolis Minn., USA) served as positive and negative controls respectively. FIG. 8 illustrates an example of how the synovial fluid from a rheumatoid arthritis patient is able to trigger the BWZ/hTREM-1 reporter cell assay in a PGLYRP1 dependent manner.

Example 17: Assembly of Mammalian Expression Vectors Useful in the Identification and Characterization of the PGLYRP1: TREM 1 Interaction A.) Construction of pJSV002 hTREM-1-G4S×3-hTREM-1/Fc6mut (SEQ ID NO: 9)

An Fc receptor binding deficient version of human IgG1 was built by eliminating the first 215 amino acids of human IgG1 comprising the variable and constant one (CH1) domain and making the following amino acid substitutions within the hinge, constant 2 and constant 3 domains: (E216G, C220S, L234A, L235E, G237A, A3305, P331S). This construct was given the name Fc6mut since six mutations were made to modulate binding to Fc receptors while a $7^{th}$ mutation (E216G) was incorporated to create a ApaI restriction cloning site. These mutations were built into pJSV002 (modified pTT5, Zhang J et al. Protein Expression and Purification, Vol, 65, Issue 1, May 2009, pp 77-8) allow cloning of extracellular domains of receptors 5' of Fc6mut as EcoRI/ApaI fragments. A cDNA was synthesised with a 5' EcoRI restriction site, a GCCACC Kozak sequence the CD33 leader sequence followed by the extracellular domain of human TREM-1 (aa17-200) with a interspaced KpnI restriction site and glycine-glycine-glycine-serine spacer repeated three times (G4S×3) followed by an additional copy of the extracellular domain of human TREM-1 (aa17-200) and an ApaI site to allow cloning upstream of the Fc6mut. This synthesised DNA was cut with EcoRI and ApaI and ligated into pJSV002 Fc6mut that had also been prepared with an EcoRI/ApaI digestion. This ligation was electroporated into DH10B E. coli and plated onto ampicillin agar plates. Individual clones were grown overnight in 2 mls LB+ampicillin cultures and miniprepped followed by restriction screening with EcoRI/ApaI to find clones with the appropriate 1219 base pair insert. Correct clones were sequenced, and one of the correct clones (#519) was selected for preparation of additional DNA by big prep.

B.) Construction of hTREM-1-COMP-SBP38x2-6His (SEQ ID NO: 10)

To create a pentameric TREM ECD molecule, a C terminal epitope tag was created in the pJSV002 expression vector. A synthetic cDNA encoding the 3' end of cartilage oligomeric protein (COMP) was fused to two copies of the streptavidin binding protein domain (SBP) followed by a C-terminal 6xHis domain, built into pJSV002 such that extracellular domains of receptors could be cloned 5' as of this fragment, as an EcoRI/KpnI fragment. Subsequently a hTREMcDNA was synthesised containing an EcoRI restriction site followed by GCCACC Kozak sequence and the extracellular domain of human TREM-1 with a C-terminal KpnI site. This EcoRI/KpnI fragment was ligated into pJSV002 COMP-SBP38x2-6His vector described above. This ligation was electroporated into DH10B E.coli (Life Technolohies, Carlsbad Calif., USA) and plated onto ampicillin agar plates. Individual clones were grown overnight in 2 mls LB+ampicillin cultures and miniprepped followed by restriction screening with EcoRI/KpnI to find clones with the appropriate 616 bp insert. Correct clones were sequenced, and one of the correct clones #525 was selected for preparation of additional DNA by big prep. The full length cDNA is listed as SEQ ID NO: 10.

C.) Construction of pJSV002 hCD83-G4S×3-hCD83/Fc6mut (SEQ ID NO: 11)

hCD83 tetramer has previously been shown to have low binding by FACS analysis when tested against a wide range of cell lines and therefore made an excellent negative control for the IPMS experiment outlined in example 3. To create this molecule, a cDNA was synthesised with a 5' EcoRI restriction site, a GCCACC Kozak sequence, the CD33 leader sequence followed by the extracellular domain of human CD83 with a interspaced KpnI restriction site and glycine-glycine-glycine-serine spacer repeated three times (G4S×3) followed by an additional copy of the extracellular domain of human CD83. This cDNA was then cloned upstream of the hFc6mut in the pJSV002 expression vector previously described. The resulting mature protein is listed as SEQ ID NO: 6 and the tandem CD83 extracellular domain cDNA sequence between EcoR1 and Apa1 is shown as SEQ ID NO: 11.

D.) Construction of pJSV002 NCOMP-hDCIR (SEQ ID NO: 12)

As a negative control for the hTREM-1-COMP pentamer used in example 5, hDCIR-COMP was used. A pJSV002 based expression plasmid was created with the following elements: 6xHIS tag followed by two copies of the streptavidin binding protein domain (SBP) fused to the 3' end of cartilage oligomeric protein (COMP) such that extracellular domains of type 2 receptors could be cloned 3' of this fragment as an BglIII/BamHI fragments and expressed as pentameric soluble receptors. A PCR fragment was amplified from a synthetic cDNA template to generate a DNA fragment with BglII and BamHI ends on the 5' and 3' ends respectively. This fragment was cut with BglII and BamHI restriction enzymes followed by band purification. The resulting fragment was ligated into pJSV002 NCOMP that had been previously cut with BglII and BamHI. The ligation was electroporated into DH10B E. coli and plated onto ampicillin selection agar. Clones were picked, mini-prepped and screened with EcoRI and BamHI and clones with the proper 1.137 kB insert were sequenced. The cDNA coding for the full open reading frame including NCOMP-SBP and DCIR sequence is designated SEQ ID NO: 12 and codes for the previously referred to mature peptide sequence SEQ ID NO: 4.

E.) Construction of pNNC649-hTREM1-hFc6mut Dimer

TREM1-Fc dimer was used in Example 14 to confirm binding to PGLYRP1 and test binding to other PGLYRP family members. A pTT5 based plasmid (Zhang J et al., Protein Expression and Purification, Vol. 65, Issue 1, May 2009, pp. 77-8) pNNC649 was utilized to allow cloning of extracellular domains of receptors in frame and 5' of Fc6mut. In order to express hTREM1-Fc6mut, a cDNA was synthesised with a 5' EcoRI restriction site, a GCCACC Kozak sequence and a hCD33 leader sequence followed by the extracellular domain of human TREM-1 (aa17-200) followed by a Kpn1 site. This cDNA was cloned into pNNC549 using restriction enzyme and DNA ligase techniques familiar to those skilled in the art. The cDNA coding for the full open reading frame including CD33 leader, hTREM1 ECD and Fc6mut sequence is designated SEQ ID NO: 43 and codes for the mature peptide sequence SEQ ID NO: 44.

F.) Construction of pNNC649-hTREML1-Fc6mut Dimer

A synthetic cDNA was created with a 5' EcoRI restriction site, a GCCACC Kozak sequence and a hCD33 leader sequence followed by the extracellular domain of human TREML1 (aa16-162) followed by a KpnI site. This cDNA was cloned into pNNC549 vector previously described using restriction enzyme and DNA ligase techniques familiar to those skilled in the art. The cDNA coding for the full open reading frame including CD33 leader, hTREML1 ECD and Fc6mut sequence is designated SEQ ID NO: 45 and codes for the mature peptide sequence SEQ ID NO: 46.

G.) Construction of pNNC649-hTREML2-Fc6mut Dimer

A synthetic cDNA was created with a 5' EcoRI restriction site, a GCCACC Kozak sequence and a hCD33 leader sequence followed by the extracellular domain of human TREML2 (aa19-268) followed by a KpnI site. This cDNA was cloned into pNNC549 vector previously described using restriction enzyme and DNA ligase techniques familiar to those skilled in the art. The cDNA coding for the full open reading frame including CD33 leader, hTREML2 ECD and Fc6mut sequence is designated SEQ ID NO: 47 and codes for the mature peptide sequence SEQ ID NO: 48.

H.) Construction of pNNC649-hTREM2-Fc6mut Dimer

A synthetic cDNA was created with a 5' EcoRI restriction site, a GCCACC Kozak sequence and a hCD33 leader sequence followed by the extracellular domain of human TREM2 (aa19-174) followed by a KpnI site. This cDNA was cloned into pNNC549 vector previously described using restriction enzyme and DNA ligase techniques familiar to those skilled in the art. The cDNA coding for the full open reading frame including CD33 leader, hTREM2 ECD and Fc6mut sequence is designated SEQ ID NO: 49 and codes for the mature peptide sequence SEQ ID NO: 50.

Example 18: A Multimerised PGLYRP1 Activates TREM-1

A counter-structure or ligand for TREM-1 was identified through binding analysis and IP/MS proteomics. The identity of the ligand, PGLYRP1 (or PGRP-S) was subsequently validated through specific blockage.

Interestingly, while binding of the soluble PGLYRP1 can be demonstrated to the TREM-1, activation of the TREM-1 by PGLYRP1 requires the concurrent presence of a scaffolding agent such as Neutrophil Extracellular Traps (NETs) or PGN.

To test if such alternative, and multimerised formats of PGLYRP1 might bind and/or activate TREM-1, a cell-associated PGLYRP1 protein was designed and expressed. Two conceptually distinct PGLYRP1 constructs were tested. In one, a GPI-anchoring sequence motif was added to the C-terminal end of PGLYRP1. In another, PGLYRP1 was artificially anchored in the cell-membrane through addition, at the N-terminus, of an intracellular (IC) and transmembrane domain (TM) derived from the Type II receptor MDL-1. The latter constructs were denoted Type II PGLYRP1. In Type II 1.0 (SEQ ID NO: 37), the charged amino acid of the native MDL-1 receptor TM is maintained, and efficient expression of this protein, is dependent on co-expression of DAP12. In the Type II 2.0 PGLYRP1 construct (SEQ ID NO: 38), the charged TM residue has been substituted with a neutral amino acid (Lysine to Leucine), enabeling the protein to be expressed independently of eg. DAP12. The cDNAs encoding these constructs were transiently expressed in HEK293 6E cells, cells were harvested on day two post-transfection and analyzed for their ability to stimulate the reporter cell line BWZ/hTREM1. Type II PGLYRP1 transfectants were co-incubated with BWZ/hTREM1 reporter cells in the absence of PGN. TREM1 activation was read out after 18 hours using the BetaGlo reagent (Cat. no. E4720, Promega, Madison Wis., USA). The transfectants expressing Type II PGLYRP1 induced activation of TREM-1 in the absence of PGN, to a level 24-fold higher than seen with control cells transfected with empty expression vector. In contrast, the GPI-anchored PGLYRP1, immobilized via the C-terminus of PGLYRP1, did not mediate any TREM-1 activation. Expression of the membrane-bound and immobilized PGLYRP1 protein at the cell-surface was ascertained by flow cytometry using a polyclonal anti-PGLYRP1 antibody (AF2590). Both proteins, Type II PGLYRP1 and GPI-PGLYRP1, were demonstrated to indeed be cell-surface expressed.

| Construct | Fold activity |
| --- | --- |
| C-GPI PGLYRP1 | 2.0 ± 0.4 (n = 3) |
| Type II 1.0 PGLYRP1 | 24 ± 3.3 (n = 3) |

The table above shows that PGLYRP1 bound to the cell membrane surface via a C-terminal GPI anchor is not as potent in inducing TREM-1 activity as a Type II PGLYRP1 protein bound to the cell membrane via the N-terminal part. This illustrates the importance of a free C-terminal PGLYRP1 part to be able to stimulate TREM-1.

Type II PGLYRP1 activation was further demonstrated to be inhibited specifically by anti-PGLYRP1 antibody. Addition of the polyclonal (Cat. no. AF2590, R&D Systems, Minneapolis Minn., USA) PGLYRP1 antibody at high concentration (1 µg/100 µl assay volume) was thus able to totally inhibit this PGLYRP1 induced activity.

| Condition | Activity |
| --- | --- |
| Type II 1.0 PGLYRP1 | 100% |
| Type II 1.0 PGLYRP1 + Iso Ab | 98% |
| Type II 1.0 PGLYRP1 + AF2590 | 9.7% |

Sequences at the very C-terminal domain of PGLYRP1 appear critical to the ability to activate the TREM-1 receptor. Several constructs, which share as a common feature, the modification at the extreme C-terminus of PGLYRP1, have thus been seen to not mediate activation of TREM1/BWZ reporter activity, while the corresponding constructs, which in contrast have been modified at the N-terminus, do exhibit activity.

| Construct | Activity |
| --- | --- |
| PGLYRP1 Native | +++ |
| PGLYRP1 N-Flag | +++ |
| PGLYRP1 C-Flag | – |
| PGLYRP1 N-Fc | +++ |
| PGLYRP1 C-Fc | (+) |
| Type II 1.0 PGLYRP1 | +++ |
| PGLYRP1 C-GPI | (+) |

This indicates the importance of a free C-terminal PGLYRP1 part to be able to stimulate TREM-1.

Interpretation and Biological Perspectives

The ability to activate the TREM-1 receptor using either the native PGLYRP1-ligand in the presence of PGN or alternatively, novel PGLYRP1 variants which have been demonstrated to overcome the need for PGN, clearly demonstrates that PGN is not an absolute co-factor requirement for TREM-1 activation. The common feature of the various molecular PGLYRP1 formats which were demonstrated to confer PGN-independent TREM-1 activation appear to be a high density format leading to the hypothesis that the predominant role of PGN, when acting as co-factor for the native ligand, is to provide a scaffold for multimerisation. In vivo, such a scaffold could be provided by Neutrophil Extracellular Traps (NETS) (Blood 2005, 106: 2551-58) or other naturally occurring matrix structures, such as hyaluronic acid, proteoglycan structures, such as versican, aggrecan, decorin, or fibrin, all of which may multimerise or otherwise present PGLYRP1.

These findings suggest that modification of the C-terminal part of PGLYRP1 reduces TREM-1 activation which in turn indicates that blocking the C-terminal part of PGLYRP1 with an agent, such as an antibody directed against the C-terminal part of PGLYRP1, would decrease the TREM-1 interaction and thereby TREM-1 stimulation.

Example 19: Type II PGLYRP1 is Able to Induce TNFalpha Release in Synovial Tissue Cells from Rheumatoid Arthritis Patients Synovial tissue samples were obtained from RA patients during total knee replacement. Single suspension of synovial tissue cells was isolated by a digestion via 4 mg/ml of collagenase (Cat, no. 11088793001, Roche, Mannheim, Germany) and 0.1 mg/ml of DNase (Cat. no. 11284932001, Roche, Mannheim, Germany) for 1 h at 37 degree. The synovial tissue cells ($1 \times 10^5$/well in culture medium RPMI (Cat. no. 22400105, Life Technologies, Carlsbad Calif., USA)+10% FCS (Cat. no. S0115, BioChrom AG, Berlin, Germany) were co-cultured with various doses of HEK cells transiently transfected with type II PGLYRP1 under hypoxic condition. After 24 h incubation, cell supernatants were harvested, and cytokines were measured by TNFa ELISA (Cat. no, DY210, R&D Systems, Minneapolis, Minn., USA).

| Type II PGLYRP1 (HEK transfected)/ | TNF-α (pg/ml) release | | | | | |
| --- | --- | --- | --- | --- | --- | --- |
| Control HEK | $1 \times 10^5$ | $3 \times 10^4$ | $1 \times 10^4$ | $3 \times 10^3$ | $1 \times 10^3$ | 0 |
| IgG4 + Type II | 121.17 | 114.08 | 95.02 | 54.56 | 57.87 | 33.47 |
| IgG4 + Control | 55.65 | 63.73 | 57.99 | 33.78 | 36.40 | 36.32 |

This example shows that the TREM-1 ligand can induce TNF-alpha in a dose-dependent manner in synovial tissue cells from rheumatoid arthritis patients.

Example 20: PGLYRP1 Antibodies Block the TREM-1 Mediated Signal in Neutrophils and Decrease IL-8 Release Having demonstrated that neutrophils can release PGLYRP1 and that neutrophils also express the TREM-1 receptor, we tested whether neutrophil-derived PGLYRP1 can stimulate neutrophils in an autocrine manner. Isolated neutrophils were stimulated with PGN-SA (Cat. no. tlrl-pgnsa, Invivogen, San Diego Calif., USA), and the release of IL-8 into the culture medium was measured. A PGLYRP1 antibody, mAb 0184, was able to decrease the PGN-SA-induced IL-8 release. Neutrophils were isolated from human healthy donor whole blood as described in example 3 and resuspended in RPMI/10% FBS. The cells were plated out at 1.5×10E6 cells/ml, and triplicate test wells were tested under the following conditions: no added stimulation, 10 μg/ml PGN-SA only, or 10 μg/ml PGN-SA in the presence of PGLYRP1 antibody or hIgG4 isotype control antibody at 4 μg/ml. The samples were cultured 24 hours in a 37° C., 5% $CO_2$ incubator. Supernatants were then harvested and analysed for IL-8 using the Bioplex Pro Human Cytokine IL-8 set (Cat. no. 171-B5008M, BioRad, Hercules Calif., USA).

| Neutrophils stimulated with | IL-8, pg/ml | |
|---|---|---|
| | Avg | SD |
| No addition | 52 | 3 |
| PGN-SA | 1158 | 341 |
| PGN-SA + isotype control | 1195 | 144 |
| PGN-SA + mAb 0184 | 449 | 50 |

This example illustrates that IL-8 release from neutrophils induced by stimulation with the bacterially derived PGN-SA can be reduced by anti-PGLYRP1 antibody. The TREM-1 ligand PGLYRP1 is thus an autocrine stimulant of neutrophils, and the PGLYRP1 antibody disclosed herein are potentially useful in down-regulating neutrophil responses.

While certain features of the invention have been illustrated and described herein, many modifications, substitutions, changes, and equivalents will now be apparent to those of ordinary skill in the art. It is, therefore, to be understood that the appended embodiments are intended to cover all such modifications and changes as fall within the true spirit of the invention.

The invention claimed is:

1. A method of treating an autoimmune disease or chronic inflammation in a subject in need thereof, comprising administering to the subject an antibody or antigen-binding fragment thereof that specifically binds to human Peptidoglycan Recognition Protein 1 (PGLYRP1), wherein the antibody or antigen-binding fragment thereof is capable of reducing, blocking, or interfering with the interaction of PGLYRP1 with human Triggering Receptor Expressed on Myeloid cells -1 (TREM-1), wherein the antibody or antigen-binding fragment thereof comprises:
  (i) a CDRH1 sequence as set forth in amino acid residues 31 to 35 of SEQ ID NO: 15, a CDRH2 sequence as set forth in amino acids 50 to 66 of SEQ ID NO: 15, a CDRH3 sequence as set forth in amino acid residues 99 to 108 of SEQ ID NO: 15, a CDRL1 sequence as set forth in amino acid residues 24 to 34 of SEQ ID NO: 16, a CDRL2 sequence as set forth in amino acid residues 51 to 56 of SEQ ID NO: 16, and a CDRL3 sequence as set forth in amino acid residues 89 to 97 of SEQ ID NO: 16;
  (ii) a CDRH1 sequence as set forth in amino acid residues 31 to 35 of SEQ ID NO: 19, a CDRH2 sequence as set forth in amino acids 50 to 66 of SEQ ID NO: 19, a CDRH3 sequence as set forth in amino acid residues 99 to 109 of SEQ ID NO: 19, a CDRL1 sequence as set forth in amino acid residues 24 to 33 of SEQ ID NO: 20, a CDRL2 sequence as set forth in amino acid residues 49 to 55 of SEQ ID NO: 20, and a CDRL3 sequence as set forth in amino acid residues 88 to 96 of SEQ ID NO: 20;
  (iii) a CDRH1 sequence as set forth in amino acid residues 31 to 35 of SEQ ID NO: 23, a CDRH2 sequence as set forth in amino acids 50 to 66 of SEQ ID NO: 23, a CDRH3 sequence as set forth in amino acid residues 99 to 108 of SEQ ID NO: 23, a CDRL1 sequence as set forth in amino acid residues 24 to 33 of SEQ ID NO: 24, a CDRL2 sequence as set forth in amino acid residues 49 to 55 of SEQ ID NO: 24, and a CDRL3 sequence as set forth in amino acid residues 88 to 96 of SEQ ID NO: 24;
  (iv) a CDRH1 sequence as set forth in amino acid residues 31 to 35 of SEQ ID NO: 27, a CDRH2 sequence as set forth in amino acids 50 to 66 of SEQ ID NO: 27, a CDRH3 sequence as set forth in amino acid residues 99 to 106 of SEQ ID NO: 27, a CDRL1 sequence as set forth in amino acid residues 24 to 33 of SEQ ID NO: 28, a CDRL2 sequence as set forth in amino acid residues 49 to 54 of SEQ ID NO: 28, and a CDRL3 sequence as set forth in amino acid residues 87 to 95 of SEQ ID NO: 28;
  (v) a CDRH1 sequence as set forth in amino acid residues 31 to 35 of SEQ ID NO: 31, a CDRH2 sequence as set forth in amino acids 50 to 66 of SEQ ID NO: 31, a CDRH3 sequence as set forth in amino acid residues 99 to 109 of SEQ ID NO: 31, a CDRL1 sequence as set forth in amino acid residues 24 to 35 of SEQ ID NO: 32, a CDRL2 sequence as set forth in amino acid residues 51 to 57 of SEQ ID NO: 32, and a CDRL3 sequence as set forth in amino acid residues 90 to 98 of SEQ ID NO: 32; or
  (vi) a CDRH1 sequence as set forth in amino acid residues 31 to 35 of SEQ ID NO: 35, a CDRH2 sequence as set forth in amino acids 50 to 66 of SEQ ID NO: 35, and a CDRH3 sequence as set forth in amino acid residues 99 to 109, a CDRL1 sequence as set forth in amino acid residues 24 to 34 of SEQ ID NO: 36, a CDRL2 sequence as set forth in amino acid residues 50 to 56 of SEQ ID NO: 36, and a CDRL3 sequence as set forth in amino acid residues 89 to 96 of SEQ ID NO: 36.

2. The method of claim 1, wherein the autoimmune disease is inflammatory bowel disease (IBD), rheumatoid arthritis, psoriasis, psoriatic arthritis, Crohn's disease, ulcerative colitis, or systemic lupus erythematosus.

3. The method of claim 1, wherein the antibody or antigen-binding fragment thereof is a chimeric, humanized, or human antibody.

4. The method of claim 1, wherein the antibody or antigen-binding fragment thereof has a $K_D$ for the interaction with PGLYRP1 of $1\times10^{-9}$M or less, as measured by surface plasmon resonance.

5. The method of claim 1, wherein the antibody or antigen-binding fragment thereof is capable of reducing greater than 50% TREM-1 response in a BWZ/hTREM-1 reporter cell assay.

6. The method of claim 1, wherein the antibody or antigen-binding fragment thereof is capable of blocking greater than 50% of TREM-1 mediated IL-8 release from isolated cultured neutrophils.

* * * * *